(12) United States Patent
Bairstow et al.

(10) Patent No.: US 8,304,524 B2
(45) Date of Patent: Nov. 6, 2012

(54) MANUFACTURE OF FACTOR H (FH) AND FH-DERIVATIVES FROM PLASMA

(75) Inventors: Shawn F. Bairstow, Gurnee, IL (US); Richard Johnson, Mundelein, IL (US); Sindhu Ramachandran, Lake Zurich, IL (US); Ruth Madlener, Vienna (AT); Wolfgang Teschner, Vienna (AT); Hans-Peter Schwarz, Vienna (AT)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 199 days.

(21) Appl. No.: 12/842,944

(22) Filed: Jul. 23, 2010

(65) Prior Publication Data

US 2011/0021432 A1    Jan. 27, 2011

Related U.S. Application Data

(60) Provisional application No. 61/227,968, filed on Jul. 23, 2009.

(51) Int. Cl.
*C07K 1/30* (2006.01)
*A61K 35/16* (2006.01)

(52) U.S. Cl. ........................... 530/424; 530/380

(58) Field of Classification Search ................. None
See application file for complete search history.

(56) References Cited

U.S. PATENT DOCUMENTS

| 2007/0020647 A1 | 1/2007 | Hageman et al. |
| 2008/0318841 A1 | 12/2008 | Chtourou et al. |
| 2009/0118163 A1 | 5/2009 | Gronski et al. |

FOREIGN PATENT DOCUMENTS

| EP | 0 222 611 A2 | 5/1987 |
| WO | WO 2007/038995 A1 | 4/2007 |
| WO | WO 2007/066017 A2 | 6/2007 |
| WO | WO 2007/066017 A3 | 6/2007 |
| WO | WO 2008/113589 A1 | 9/2008 |

OTHER PUBLICATIONS

Nitschmann, H., et al., "Vereinfachtes Verfahren zur Gewinnung von Humanem Albumin and Gamma-Globulin aus Blutplasma Mittels Alkoholfaellung," *Helvetica Chimica Acta*, Verlag Helvetica Chimica Acta, vol. 37, Jan. 1, 1954, pp. 866-873.
International Search Report, Appln. No. PCT/US2010/043151, Int. Filing Date: Jul. 23, 2010.

*Primary Examiner* — Suzanne M Noakes
(74) *Attorney, Agent, or Firm* — Morgan Lewis & Bockius LLP

(57) ABSTRACT

The present invention provides compositions and pharmaceutical formulations of Factor H derived from plasma. Also provided are methods for the manufacture of the Factor H compositions and formulations, as well as methods for the treatment of diseases associated with Factor H dysfunction.

17 Claims, 13 Drawing Sheets

MANUFACTURE OF FACTOR H (FH) AND FH-DERIVATIVES FROM PLASMA

CROSS-REFERENCES TO RELATED APPLICATIONS

The present application claims the benefit of U.S. Provisional Application No. 61/227,968 filed Jul. 23, 2009, which is expressly incorporated herein by reference in its entirety for all purposes.

BACKGROUND OF THE INVENTION

Unlike other biologics that are produced via recombinant expression of DNA vectors in host cell lines, plasma-derived proteins are fractionated from human blood and plasma donations. Thus, the supply of these products cannot be increased by simply increasing the volume of production. Rather the level of commercially available blood products is limited by the available supply of blood and plasma donations. This dynamic results in a shortage in the availability of raw human plasma for the manufacture of new plasma-derived blood factors that have lesser established commercial markets, including Complement Factor H (CFH).

Factor H (FH) is a member of the regulators of complement activation family and is a complement control protein. It is a large (155 kilodaltons), soluble glycoprotein that circulates in human plasma (at a concentration of 500-800 micrograms per milliliter). Its main job is to regulate the Alternative Pathway of the complement system, ensuring that the complement system is directed towards pathogens and does not damage host tissue. Factor H regulates complement activation on self cells by possessing both cofactor activity for Factor I mediated C3b cleavage, and decay accelerating activity against the alternative pathway C3 convertase, C3bBb. Thus, Factor H protects self cells, but not foreign pathogens (e.g., bacteria, protists, and viruses), from complement activation by binding to glycosaminoglycans (GAGs) that are present on the surface of human cells, but not on the pathogenic cell surfaces.

Due to its regulatory role in complement activation, Factor H has been implicated as a potential therapeutic agent for several human disease states, including age-related macular degeneration (AMD), hemolytic uremic syndrome (aHUS) and membranoproliferative glomerulonephritis (MPGN). While a causal relationship between the single nucleotide polymorphism (SNP) in complement control protein (CCP) module 7 of Factor H and age-related macular degeneration (AMD) has been characterized, medicaments based on this causal relationship have thus far not been identified.

Due in part to the increasing global demand and fluctuations in the available supply of plasma-derived blood products, such as immunoglobulin products, several countries, including Australia and England, have implemented demand management programs to protect supplies of these products for the highest demand patients during times of product shortages.

For example, it has been reported that in 2007, 26.5 million liters of plasma were fractionated, generating 75.2 metric tons of IVIG, with an average production yield of 2.8 grams per liter (Robert P., supra). This same report estimated that global IVIG yields are expected to increase to about 3.43 grams per liter by 2012. However, due to the continued growth in global demand for IVIG, projected at between about 7% and 13% annually between now and 2015, more raw plasma will need to be dedicated to immunoglobulin purification to meet the demand in spite of the expected improvement of the overall IVIG yield. This requirement will limit the availability of plasma for the manufacture of new plasma-derived blood products.

Due to the lack of plasma available for the manufacture of new plasma-derived products, their manufacture must be integrated into the existing framework of the established manufacturing processes for plasma-derived products such as immunoglobulins and albumin. Factor H, implicated as a potential therapeutic for AMD, aHUS, and MPGN, among other conditions, is one such plasma-derived blood product that is gaining the attention of physicians. However, due to the resources devoted to, for example, IgG gamma globulin manufacture, methods are needed for the manufacture of Factor H that can be introduced into the existing manufacturing schemes. Several methods have been suggested to achieve just this, however, many of these proposed solutions require modification of the existing manufacturing scheme for established products. Such changes will require new regulatory approvals for the established products and may even result in alterations of the characteristics of the established products.

For example, WO 2007/066017 describes methods for the production of Factor H preparations from the supernatant of a cryoprecipitate. The disclosed method consists of preparing a supernatant of a cryoprecipitate, submitting the supernatant to anion exchange chromatography (AEC), submitting the flow through from the AEC to heparin affinity chromatography (HAC), submitting the relevant eluate from the HAC to strong cation exchange chromatography (CEC), submitting the relevant eluate from the CEC to strong anion exchange chromatography (sAEC) and eluting the Factor H from the sAEC. Disadvantageously, cryoprecipitate supernatants are common intermediate fractions in the manufacturing processes of many commercially important plasma-derived blood products, including IgG gamma globulins (IVIG and subcutaneous) and albumin. Submitting this fraction to chromatography steps will alter the cryoprecipitate supernatant and would require that the manufacturing processes of the established downstream blood products be adapted in unknown fashions. In addition to requiring a complete revalidation and possible redesign of these manufacturing processes, regulatory re-approval of the manufacturing procedures from key regulatory agencies is needed.

Likewise, WO 2008/113589 describes methods for the production of Factor H preparations from human plasma. Specifically, this publication describes the purification of Factor H from three known plasma processing fractions, namely a Cohn-Oncley Fraction I supernatant, a Cohn-Oncley Fraction III precipitate, and a Kistler/Nitschmann Precipitate B fraction. With respect to the first method, WO 2008/113589 discloses that Factor H can be removed from a Cohn-Oncley Fraction I supernatant by the addition of a heparin affinity chromatography step. Disadvantageously, the Cohn-Oncley Fraction I supernatant is a common intermediate fraction in the manufacturing processes of many commercially important plasma-derived blood products, including IgG gamma globulins (IVIG and subcutaneous) and albumin. Similarly, many immunoglobulin (e.g., IgG, IVIG, etc.) manufacturing processes do not rely on Cohn-Oncley Fraction III precipitation or Kistler/Nitschmann Precipitate B steps, for example Gammagard® Liquid and Kiovig (Baxter International Inc.). The disadvantage of the introduction of additional steps, such as a heparin affinity chromatography, Fraction III precipitation, or Precipitate B steps, into the manufacturing schemes of established blood products, as outlined above, is that it requires revalidation of the manufacturing procedure, regulatory re-approval of the manufacturing procedures from key regulatory agencies, and may further have unforeseen consequences for the yield and/or purity of the otherwise established product.

As such, a need remains in the art for methods of manufacturing Factor H that do not require the use of additional input plasma or the redesign and regulatory re-approval of existing manufacturing processes for commercially important plasma-derived blood products, such as albumin and IgG gamma globulins for intravenous (IVIG) or subcutaneous administration. Advantageously, the present invention fulfills these and other needs by providing methods of manufacturing Factor H that rely entirely on previously unused manufacturing byproducts. Among other aspects, the present invention also provides novel Factor H compositions and methods for treating Factor H and complement-related diseases and disorders.

BRIEF SUMMARY OF THE INVENTION

Among other aspects, the present invention provides methods for preparing enriched compositions of plasma-derived Factor H. Advantageously, the methods provided herein allow for the industrial-scale preparation of Factor H compositions from materials otherwise discarded during the preparation of other commercially important blood products by plasma fractionation.

In one aspect, the present invention provides a method for preparing an enriched Factor H composition from plasma by extracting Factor H from a Fraction II+III filter cake. In one embodiment, the method involves the capture of Factor H from a Fraction II+III suspension by a solid phase and separation from the resulting Fraction II+III suspension.

In a second aspect, the present invention provides a method for preparing an enriched Factor H composition from plasma by extracting Factor H from a Fraction I precipitate.

In a third aspect, the present invention provides aqueous compositions of plasma-derived Factor H prepared from materials otherwise discarded during the preparation of other commercially important blood products by plasma fractionation, for example, IgG gamma globulins.

In a fourth aspect, the present invention provides pharmaceutical compositions of plasma-derived Factor H prepared from materials otherwise discarded during the preparation of other commercially important blood products by plasma fractionation, for example, IgG gamma globulins.

In a fifth aspect, the present invention provides methods for treating a disease or disorder associated with Factor H dysfunction in a subject in need thereof by administering a therapeutically effective dose of a Factor H composition prepared from materials otherwise discarded during the preparation of other commercially important blood products by plasma fractionation. Diseases and disorders associated with Factor H dysfunction include, but are not limited to, Complement Factor H (CFH) deficiency, atypical haemolytic uremic syndrome (aHUS), age-related macular degeneration (AMD), membranoproliferative glomulonephritis type II, myocardial infarction, coronary heart disease/coronary artery disease (CAD/CHD), and Alzheimer's disease In a sixth aspect, the present invention provides methods for treating a disease or disorder associated with abnormal alternative pathway complement activity in a subject in need thereof by administering a therapeutically effective dose of a Factor H composition prepared from materials otherwise discarded during the preparation of other commercially important blood products by plasma fractionation. Diseases and disorders associated with abnormal alternative pathway complement activity include, but are not limited to, rheumatoid arthritis, IgA nephropathy, asthma, systemic lupus erythematosus, and ischemia reperfusion injury.

In one aspect, the present invention provides a composition of Factor H prepared by extracting Factor H from a Fraction I precipitate or Fraction II+III filter cake. In one embodiment of the Factor H compositions provided herein, at least 90% of the protein content of the composition is Factor H. In another embodiment, at least 95% of the protein content of the composition is Factor H.

In one embodiment of the Factor H compositions provided herein, the composition is formulated for pharmaceutical administration. In one embodiment of the pharmaceutical compositions provided herein, at least 90% of the protein content of the composition is Factor H. In another embodiment, at least 95% of the protein content of the pharmaceutical composition is Factor H. In one embodiment of the pharmaceutical compositions provided herein, the concentration of Factor H is between about 1% and about 25%.

In one embodiment, a pharmaceutical composition of Factor H is formulated for intravenous, intravitreal, or subcutaneous administration. In one specific embodiment, the composition is formulated for intravenous administration. In one embodiment, the composition is formulated for treatment of atypical haemolytic uremic syndrome (aHUS). In another specific embodiment, the composition is formulated for intravitreal administration. In one embodiment, the composition is formulated for treatment of age-related macular degeneration (AMD).

In another aspect, the present invention provides a method for treating a disease associated with Factor H dysfunction in a subject in need thereof, the method comprising administering a therapeutically effective dose of a Factor H composition according to a method provided herein. In one embodiment, the disease or condition associated with Factor H dysfunction is selected from the group consisting of age-related macular degeneration, hemolytic uremic syndrome, and membranoproliferative glomerulonephritis.

In another aspect, the present invention provides a method for treating a disease associated with abnormal alternative pathway complement activity in a subject in need thereof, the method comprising administering a therapeutically effective dose of a Factor H composition according to a method provided herein. In one embodiment, the disease associated with abnormal alternative pathway complement activity is selected from the group consisting of an autoimmune disease, a renal disease, asthma, Alzheimer disease, adult macular degeneration, proximal nocturnal hemoglobinuria, abdominal aortic aneurism, ischemia reperfusion injury, and sepsis. In a specific embodiment, the autoimmune disease is selected from the group consisting of rheumatoid arthritis, IgA nephropathy, asthma, systemic lupus erythematosus, multiple sclerosis, Anti-Phospholipid syndrome, ANCA-associated vasculitis, pemphigus, uveitis, myathemia gravis, and Hashimoto's thyroiditis.

DETAILED DESCRIPTION OF THE INVENTION

I. Introduction

Figure 1:
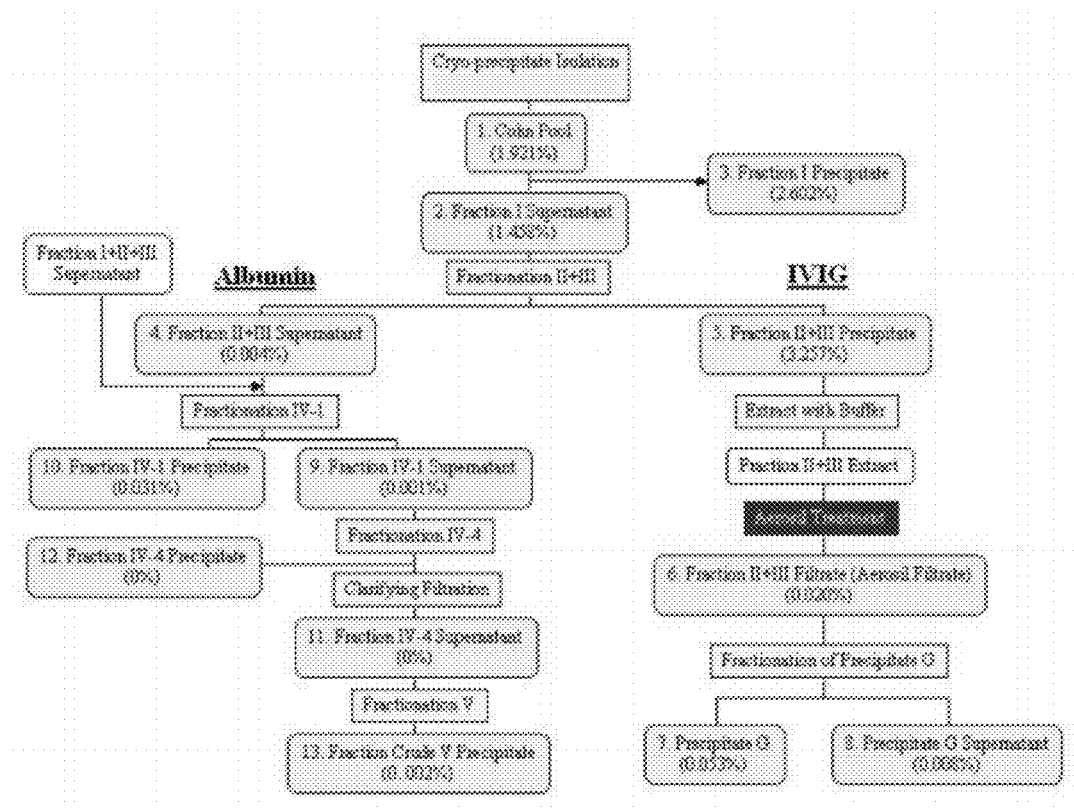
FIG. 1. Overview of an exemplary plasma fractionation scheme.

Factor H has been implicated as a potential therapeutic agent for several human disease states, including age-related macular degeneration, hemolytic uremic syndrome and membranoproliferative glomerulonephritis (MPGN). Factor H is a relatively abundant plasma protein (0.5 to 0.8 mg/mL plasma), however, this protein is currently discarded from the operations of various manufactures that specialize in the fractionation of human plasma. Among other aspects, the present invention provides methods for the isolation of Factor H from discard fractions of various fractionation processes, for example, Cohn, Oncley, Cohn-Oncley, Deutsch, Nitschmann, Kistler, and similar fractionation processes, without affecting, disrupting, or altering the normal or established processing of the plasma used for the manufacture of other plasma-derived products. Thus, in one aspect, the invention makes use of discarded plasma fractions for the production of a useful medicament for the treatment of AMD and other disorders.

Accordingly, in one aspect, it is an object of the invention to produce a purified preparation of Factor H from a pooled plasma sample. In a related aspect, the invention involves the use of such a purified fraction for the manufacture of a medicament for the treatment of AMD.

In one aspect, the present invention provides new methods for the preparation of Factor H from pooled plasma. In specific embodiments, the methods are for the preparation of Factor H from pooled human plasma and comprise the steps of: performing Cohn fractionation to obtain Fraction II+III precipitates and preparing a suspension of the combined precipitates; filtering the re-suspended Fraction II+III precipitates to obtain the Aerosil® filter cake discard left behind after filtration of the Fraction II+III suspension; extracting the filter cake according to a method comprising the steps of: (i) dissolving the filter cake in a suitable buffer of appropriate ionic strength for a time sufficient to dissolve the protein caked on said filter cake; (ii) diluting said dissolved protein with additional buffer (iii) removing debris from the diluted protein; (iv) purifying Factor H protein from said diluted protein preparation by subjecting the diluted protein to ultrafiltration on a 0.45 µm filter to produce a filtrate containing Factor H; (v) subjecting the filtrate containing Factor H to anion exchange chromatography using a NaCl gradient in the running buffer or a single step elution at a higher salt concentration to produce a pooled crude Factor H fraction; and (vi) purifying Factor H from said crude Factor H preparation by Heparin Sepharose™ chromatography using a gradient of NaCl or a single step elution at a higher salt concentration. In other embodiments, Factor H may be recovered by using step elution off of a chromatographic resin, such as an anion exchange resin or heparin affinity resin.

While in specific embodiments, the anion exchange chromatography uses DEAE Sepharose™ as the anion exchange resin, it should be understood that any anion exchange resin can be used to perform the anion exchange chromatography.

Using the method described herein the purified Factor H produced is an active Factor H preparation that is composed of a mixture of Tyr-402 and His-402 isoforms in the range 50%±20% His-402: 50%±20% Tyr-402.

In certain purification steps, the method may further comprise addition of Factor I precipitate with the filter cake in step (c)(1).

In specific embodiments the buffer used is 25 mM Tris; 5 mM EDTA; 50 mM NaCl having a pH of 8.0.

The Factor H produced by the method described may further be lyophilized.

Another aspect of the invention is a substantially purified Factor H preparation prepared according to a method described herein. More specifically, the Factor H preparation is an active Factor H preparation that is composed of a mixture of Tyr-402 and His-402 isoforms in the range 50%±20% His-402: 50%±20% Tyr-402.

The invention further contemplates a method for limiting complement activation resulting in delayed progression or onset of the development of age related macular degeneration (AMD) in a subject, comprising administering a therapeutically or prophylactically effective amount of Factor H preparation of the invention. The method of administration may be carried out on a subject who does not have any symptoms of AMD but is of an age and history that suggests that the subject is at risk of developing such symptoms. In some embodiments, the subject has drusen. The method also may be used to effectively treat subjects that display signs and/or symptoms of AMD. The subject may for example have been diagnosed with AMD.

In certain embodiments, the administration is intravenous. In other embodiments, the administration is through eye drops or other intravitreal route (e.g., intravitreal injection).

In other embodiments, the invention provides methods for limiting complement activation otherwise resulting in a disease or disorder associated with Factor H dysfunction, including without limitation, Complement Factor H (CFH) deficiency, atypical haemolytic uremic syndrome (aHUS), age-related macular degeneration (AMD), membranoproliferative glomulonephritis type II, myocardial infarction, coronary heart disease/coronary artery disease (CAD/CHD), and Alzheimer's disease, or a diseases or disorder associated with abnormal alternative pathway complement activity, including without limitation, rheumatoid arthritis, IgA nephropathy, asthma, systemic lupus erythematosus, and ischemia reperfusion injury by administering a therapeutically or prophylactically effective amount of a Factor H preparation provided herein.

Also contemplated is a method of treating a human subject judged to be at risk for the development of a disease or disorder associated with Factor H dysfunction, including without limitation, Complement Factor H (CFH) deficiency, atypical haemolytic uremic syndrome (aHUS), age-related macular degeneration (AMD), membranoproliferative glomulonephritis type II, myocardial infarction, coronary heart disease/coronary artery disease (CAD/CHD), and Alzheimer's disease, or a diseases or disorder associated with abnormal alternative pathway complement activity, including without limitation, rheumatoid arthritis, IgA nephropathy, asthma, systemic lupus erythematosus, and ischemia reperfusion injury, comprising the step of administering to the subject a prophylactically or therapeutically effective amount of a Factor H preparation of prepared according to the methods described herein, and periodically repeating said administration. In some examples, the administration is repeated for a time effective to delay the progression or onset of the development of macular degeneration in said subject. In specific embodiments, the human subject is judged to be at risk for the development of age-related macular degeneration as identified based on the presence of one or more genetic markers associated with development of age-related macular degeneration. For example, the genetic marker is a polymorphism. In one embodiment, the subject is diagnosed as at risk for the development of AMD by the detection of a specific sequence variant in the CFH gene. In some embodiments, the treatment method may be performed on a subject that has not been diagnosed with AMD. The treatment may be performed alone or in combination with other treatments for AMD. The treatment method may be administered to a subject that has not previously been treated for AMD, and as such is "treatment naïve".

Another aspect of the invention is a pharmaceutical preparation that comprises an active Factor H preparation prepared from a method described herein and a pharmaceutically acceptable carrier.

II. Definitions

As used herein, "Factor H" refers to a protein component of the alternative pathway of complement encoded by the complement factor G gene (for example, CFH; NM000186; GeneID:3075; UniProt ID P08603; Ripoche et al., *Biochem. J.* 249:593-602(1988)). Factor H is translated as a 1,213 amino acid precursor polypeptide which is processed by removal of an 18 amino acid signal peptide, resulting in the mature Factor H protein (amino acids 19-1231). As used in the present invention, Factor H encompasses any natural variants, alternative sequences, isoforms or mutant proteins that can be found in a plasma sample, for example a human plasma sample. Examples of Factor H mutations found in the human population include, without limitation, Y402H; V62I; R78G; R127L; Δ224; Q400K; C431S; T493R; C536R; I551T; R567G; C630W; C673S; C673Y; E850K; S890I; H893R; C915S; E936D; Q950H; Y951H; T956M; C959Y; W978C; N997T; V1007I; V1007L; A1010T; T1017I; Y1021F; C1043R; N1050Y; I1059T; Q1076R; R1078S; D1119G; V1134G; Y1142D; Q1143E; W1157R; C1163W; W1183L; W1183R; T1184R; L1189R; S1191L; G1194D; V1197A; E1198A; F1199S; R1210C; R1215G; R1215Q; YPTCAKR1225:1231FQS; and P1226S. Many of the these mutations have been found to be associated with a variety of diseases and disorders, including, atypical haemolytic uremic syndrome (aHUS), age-related macular degeneration (AMD), membranoproliferative glomulonephritis type II (MPGNII), CFH deficiency, and basal laminar drusen. Factor H also includes proteins containing post-translational modifications. For example, Factor H is believed to be modified by N-acetylglucosamine (GlcNAc) at residues 529, 718, 802, 822, 882, 911, 1029, and 1095.

As used herein, "cryo-poor plasma" refers to the supernatant created after the removal of cryo-precipitate formed by thawing plasma or pooled plasma at temperatures near freezing, e.g., at temperatures below about 10° C., preferably at a temperature no higher than about 6° C. In the context of the present invention, plasma may refer interchangeably to recovered plasma (i.e., plasma that has been separated from whole blood ex vivo) or source plasma (i.e., plasma collected via plasmapheresis). Cryo-precipitation is commonly performed, for example, by thawing previously frozen pooled plasma, which has already been assayed for safety and quality considerations, although fresh plasma may also be used. After complete thawing of the frozen plasma at low temperature, separation of the solid cryo-precipitates from the liquid supernatant is performed in the cold (e.g., $\leq 6°$ C.) by centrifugation of filtration.

As used herein, a "Cohn pool" refers to the starting material used for the fractionation of a plasma sample or pool of plasma samples. Cohn pools include whole plasma, cryo-poor plasma samples, and pools of cryo-poor plasma samples that may or may not have been subjected to a pre-processing step. In certain embodiments, a Cohn pool is a cryo-poor plasma sample from which one or more blood factor have been removed in a pre-processing step, for example, adsorption onto a solid phase (e.g., aluminum hydroxide, finely divided silicon dioxide, etc.), or chromatographic step (e.g., ion exchange or heparin affinity chromatography). Various blood factors, including but not limited to Factor Eight Inhibitor Bypass Activity (FEIBA), Factor IX-complex, Factor VII-concentrate, or Antithrombin III-complex, may be isolated from the cryo-poor plasma sample to form a Cohn pool.

As used herein, a "Fraction II+III filter cake" refers to a solid phase recovered after the filtration or centrifugation of a Cohn-Oncley or equivalent Fraction II+III paste suspension. In a preferred embodiment, a Fraction II+III suspension will be treated with an adsorptive material, for example, finely divided silicon dioxide, to remove impurities such as lipids, fibrinogen, amidolytic activity, prekallikren activity, and lipoproteins. In another preferred embodiment, filter aid may be added to the Fraction II+III suspension prior to centrifugation or filtration. In a most preferred embodiment, a Fraction II+III suspension will be treated with both an adsorptive material and a filter aid prior to centrifugation or filtration. Upon separation of the clarified Fraction II+III suspension supernatant, the recovered solid phase material is referred to as the Fraction II+III filter cake.

As used herein, "finely divided silicon dioxide" or "finely divided silica" refers to an oxide of silicon having the formula $SiO_2$, manufactured in a fashion that allows for the adsorption of Factor H onto its surface. Exemplary forms of finely divided silicon dioxide suitable for use in the methods of the present invention include, without limitation, fumed silica, pyrogenic silica, Aerosil®, Cab-O-Sil™, colloidal silica, diatomaceous earth, and the like. In a preferred embodiment, a commercial hydrophilic fumed silica product is used for the methods provided herein. Non-limiting examples of these products include those marketed by Evonik Industries under the trade name Aerosil® (e.g., Aerosil 90, Aerosil 130, Aerosil 150, Aerosil 200, Aerosil 300, Aerosil 380, Aerosil OX 50, Aerosil EG 50, Aerosil TT 600, Aerosil 200 SP, Aerosil 300 SP, and Aerosil 300/30).

As used herein, a "disease or disorder associated with Factor H dysfunction" refers to any disease, disorder, or condition in a subject that is caused by, characterized by, or results in a reduced level of Factor H activity in the subject. For purposes of the present invention, Factor H activity may refer to the ability of Factor H to bind a protein or ligand, for example, C3b, C3bBb, C3b2Bb, csbC3b, complement factor B (CFB), C-reactive protein, endothelial cells, glycosaminoglycans (GAGs), or alternatively, may refer to its Factor I cofactor activity or its ability to accelerate the irreversible dissociation of C3bBb and C3b2Bb. In one embodiment, a disease or disorder associated with Factor H dysfunction results in a C3 deficiency and susceptibility to bacterial infections. In some instances, diseases or disorders associated with Factor H dysfunction include conditions that are caused by or linked to mutations and polymorphism in the CFH gene encoding Factor H (for review, see, Barlow et al., *Adv Exp Med Biol.* 2008; 632:117-42, the disclosure of which is herein incorporated by reference in its entirety for all purposes). Diseases that have been linked to mutations or polymorphisms in the CFH gene include, without limitation, Factor H deficiency, atypical haemolytic uremic syndrome (aHUS), age-related macular degeneration (AMD), membranoproliferative glomulonephritis type II (MPGNII; de Cordoba and de Jorge, *Clinical and Experimental Immunology* 151, 1-13 (2008)), myocardial infarction (Kardys et al., *Journal of the American College of Cardiology* 47, 1568-1575 (2006); Mooijaart et al., *Experimental Gerontology* 42, 1116-1122 (2007); Nicaud et al., *Journal of Molecular Medicine* 85, 771-775 (2007); Pai et al., *European Heart Journal* 28, 1297-1303 (2007); Stark et al., *Clinical Science (Lond)* 113, 213-218 (2007)), coronary heart disease/coronary artery disease (CAD/CHD; (Meng et al., *BMC Medical Genetics* 8, 62 (2007); Pulido et al., *Mayo Clinic Proceedings* 82, 301-307 (2007); Topol et al., *Human Molecular Genetics* 15 Spec No 2, R117-R123 (2006)), and Alzheimer's disease (Hamilton et al., *Neuromolecular Medicine* 9, 331-334 (2007); Zetterberg et al., *American Journal of Ophthalmology* 143, 1059-1060 (2007)). The disclosures of the forgoing references describing the associations between mutations and polymorphisms in the CFH gene and diseases associated with Factor H dysfunction are herein incorporated by reference in their entireties for all purposes.

As used herein, a "disease or disorder associated with abnormal alternative pathway complement activity" refers to a disease, disorder, or condition that results from uncontrolled or aberrant activation of the alternative pathway of complement. Generally, uncontrolled or aberrant activation of the alternative pathway of complement can result in bystander damage of host cells and tissues, as well as a depletion of C3 and corresponding susceptibility to pathogenic infections (e.g., fungal, bacterial, viral, and protistal). Examples of diseases and disorders associated with abnormal alternative pathway complement activity include, without limitation, various autoimmune diseases (such as rheumatoid arthritis, IgA nephropathy, asthma, systemic lupus erythematosus, multiple sclerosis, Anti-Phospholipid syndrome, ANCA-associated vasculitis, pemphigus, uveitis, myathemia gravis, Hashimoto's thyroiditis), Renal diseases (such as IgA nephropathy, hemolytic uremic syndrome, membranoproliferative glomerulonephritis) other disease such as asthma, Alzheimer disease, adult macular degeneration, proximal nocturnal hemoglobinuria, abdominal aortic aneurism, ischemia, and sepsis.

As used herein, the term "ultrafiltration (UF)" encompasses a variety of membrane filtration methods in which hydrostatic pressure forces a liquid against a semi-permeable membrane. Suspended solids and solutes of high molecular weight are retained, while water and low molecular weight solutes pass through the membrane. This separation process is often used for purifying and concentrating macromolecular ($10^3$-$10^6$ Da) solutions, especially protein solutions. A number of ultrafiltration membranes are available depending on the size of the molecules they retain. Ultrafiltration is typically characterized by a membrane pore size between 1 and 1000 kDa and operating pressures between 0.01 and 10 bar.

As used herein, the term "diafiltration" is performed with the same or a similar membrane as ultrafiltration and is typically performed in a tangential flow filtration mode. During diafiltration, buffer is introduced into the recycle tank while filtrate is removed from the unit operation. In processes where the product is in the retentate (for example, Factor H), diafiltration is particularly useful for separating protein from small molecules like sugars and salts. In certain cases, diafiltration can be used to exchange the solution, buffer, or individual components of a buffering system.

As used herein, the term "about" denotes an approximate range of plus or minus 10% from a specified value. For instance, the language "about 20%" encompasses a range of 18-22%.

As used herein, the term "mixing" describes an act of causing equal distribution of two or more distinct compounds or substances in a solution or suspension by any form of agitation. Complete equal distribution of all ingredients in a solution or suspension is not required as a result of "mixing" as the term is used in this application.

As used herein, the term "solvent" encompasses any liquid substance capable of dissolving or dispersing one or more other substances. A solvent may be inorganic in nature, such as water, or it may be an organic liquid, such as ethanol, acetone, methyl acetate, ethyl acetate, hexane, petrol ether, etc. As used in the term "solvent detergent treatment," solvent denotes an organic solvent (e.g., tri-N-butyl phosphate), which is part of the solvent detergent mixture used to inactivate lipid-enveloped viruses in solution.

As used herein, the term "detergent" is used in this application interchangeably with the term "surfactant" or "surface acting agent." Surfactants are typically organic compounds that are amphiphilic, i.e., containing both hydrophobic groups ("tails") and hydrophilic groups ("heads"), which render surfactants soluble in both organic solvents and water. A surfactant can be classified by the presence of formally charged groups in its head. A non-ionic surfactant has no charge groups in its head, whereas an ionic surfactant carries a net charge in its head. A zwitterionic surfactant contains a head with two oppositely charged groups. Some examples of common surfactants include: Anionic (based on sulfate, sulfonate or carboxylate anions): perfluorooctanoate (PFOA or PFO), perfluorooctanesulfonate (PFOS), sodium dodecyl sulfate (SDS), ammonium lauryl sulfate, and other alkyl sulfate salts, sodium laureth sulfate (also known as sodium lauryl ether sulfate, or SLES), alkyl benzene sulfonate; cationic (based on quaternary ammonium cations): cetyl trimethylammonium bromide (CTAB) a.k.a. hexadecyl trimethyl ammonium bromide, and other alkyltrimethylammonium salts, cetylpyridinium chloride (CPC), polyethoxylated tallow amine (POEA), benzalkonium chloride (BAC), benzethonium chloride (BZT); Long chain fatty acids and their salts: including caprylate, caprylic acid, heptanoat, hexanoic acid, heptanoic acid, nanoic acid, decanoic acid, and the like; Zwitterionic (amphoteric): dodecyl betaine; cocamidopropyl betaine; coco ampho glycinate; nonionic: alkyl poly(ethylene oxide), alkylphenol poly(ethylene oxide), copolymers of poly (ethylene oxide) and polypropylene oxide) (commercially known as Poloxamers or Poloxamines), alkyl polyglucosides, including octyl glucoside, decyl maltoside, fatty alcohols (e.g., cetyl alcohol and oleyl alcohol), cocamide MEA, cocamide DEA, polysorbates (Tween 20, Tween 80, etc.), Triton detergents, and dodecyl dimethylamine oxide.

As used herein, the term "therapeutically effective amount or dose" or "sufficient/effective amount or dose," refers to a dose that produces effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins; the disclosures of which are herein incorporated by reference in their entireties for all purposes).

As used in this application, the term "spraying" refers to a means of delivering a liquid substance into a system, e.g., during an alcohol precipitation step, such as a Cohn fractionation I or II+III precipitation step, in the form of fine droplets or mist of the liquid substance. Spraying may be achieved by any pressurized device, such as a container (e.g., a spray bottle), that has a spray head or a nozzle and is operated manually or automatically to generate a fine mist from a liquid. Typically, spraying is performed while the system receiving the liquid substance is continuously stirred or otherwise mixed to ensure rapid and equal distribution of the liquid within the system.

III. Methods for the Manufacture of Plasma-Derived Factor H

Having shown that the methods described herein are suitable for the preparation and production of human Factor H that retains activity, a specific object of the present invention is to provide a production procedure for a plasma-derived version of human Factor H for therapeutic use suitable for large scale. Large scale with regard to the present invention means a production procedure based on at least 200 liters plasma, preferentially at least 500 liters, even more preferentially at least 2000 liters human plasma.

Regarding production, the claimed processes starting from human plasma shall be based on the sub-fractionation of typical industrial intermediates obtained by, e.g., the fractional precipitation by ethanol in the cold (reviewed in Schultze H E, Heremans J F; Molecular Biology of Human Proteins. Volume I: Nature and Metabolism of Extracellular Proteins 1966, Elsevier Publishing Company; p. 236-317). A preferred embodiment of such purification is the purification of functional Factor H from side fractions of industrial scale plasma fractionation in such a way that established and licensed manufacturing processes of plasma products, which are under control of pharmaceutical regulatory authorities, like immunoglobulins, are not affected. For example, the filter cake obtained after filtration of a Fraction II+III paste suspension (Teschner W et al., *Vox Sang.* 2007 January; 92(1):42-55), Precipitate III (Schultze H E, Heremans J F; Molecular Biology of Human Proteins. Volume I: Nature and Metabolism of Extracellular Proteins 1966, Elsevier Publishing Company; p. 236-317 at p. 253) and precipitate B (method of Kistler and Nitschmann; supra at p. 253) are examples of such industrial sources for Factor H. Starting from those side fractions, purification procedures known in the art can be used to purify Factor H. They may be based on precipitation with polyethylene glycol (Nagasawa S, Stroud R M; Mol Immunol 1980; 17:1365-72), affinity chromatography via immobilized heparin (citation as before), ion exchange chromatography (Crossley L G, Porter R R; Biochem J 1980; 191:173-82) and hydrophobic interaction chromatography (Ripoche J, Al Salihi A, Rousseaux J, Fontaine M; Biochem J 1984; 221, 89-96).

The starting material for the invention is prepared using Cohn fractions. This fractionation is a well known fractionation used for the preparation of immunoglobulin preparations can be prepared from donor serum or monoclonal or recombinant immunoglobulins. In a typical example, blood is collected from healthy donors. Usually, the blood is collected from the same species of animal as the subject to which the immunoglobulin preparation will be administered (typically referred to as "homologous" immunoglobulins). The immunoglobulins are isolated from the blood by suitable procedures, such as, for example, Cohn fractionation, ultracentrifugation, electrophoretic preparation, ion exchange chromatography, affinity chromatography, immunoaffinity chromatography, polyethylene glycol fractionation, or the like. (See, e.g., Cohn et al., J. Am. Chem. Soc. 68:459-75 (1946); Oncley et al., J. Am. Chem. Soc. 71:541-50 (1949); Barundern et al., Vox Sang. 7:157-74 (1962); Koblet et al., Vox Sang. 13:93-102 (1967); U.S. Pat. Nos. 5,122,373 and 5,177,194; the disclosures of which are incorporated herein by reference in their entireties for all purposes.) The present invention uses the discarded fractions from the preparation of immunoglobulins. In particular, the present invention uses the fraction that is precipitated on the filtration cake once the Fraction II+III extract is filtered through an Aerosil® filter.

Generally, Factor H preparations according to the present invention can be prepared from any suitable starting materials, for example, recovered plasma or source plasma. In a typical example, blood or plasma is collected from healthy donors. Usually, the blood is collected from the same species of animal as the subject to which the Factor H preparation will be administered (typically referred to as "homologous" Factor H). The Factor H is isolated from the blood or plasma by suitable procedures, such as, for example, precipitation (alcohol fractionation or polyethylene glycol fractionation), chromatographic methods (ion exchange chromatography, affinity chromatography, immunoaffinity chromatography, etc.) ultracentrifugation, and electrophoretic preparation, and the like. (See, e.g., Cohn et al., *J. Am. Chem. Soc.* 68:459-75 (1946); Deutsch et al., *J. Biol. Chem.* 164:109-118; Oncley et al., *J. Am. Chem. Soc.* 71:541-50 (1949); Cohn et al., *J. Am. Chem. Soc.* 72:465-474 (1950); Cohn et al., *Blood Cells and Plasma Proteins: Their State in Nature* (J. L. Tullis, ed), pp. 1-58, Academic Press, New York and London (1953); Nitschmann et al., *Helv. Chim. Acta* 37:866-873; Kistler and Nitschmann, *Vox Sang.* 7:414-424 (1962); Barundern et al., *Vox Sang.* 7:157-74 (1962); Koblet et al., *Vox Sang.* 13:93-102 (1967); U.S. Pat. Nos. 5,122,373 and 5,177,194; the disclosures of which are hereby incorporated by reference in their entireties for all purposes).

In certain embodiments, Factor H is recovered from material otherwise discarded during the manufacture of other commercially important blood products by plasma fractionation. For example, in an exemplary embodiment, Factor H is extracted from a Fraction I precipitate and/or extracted from a filter cake formed after centrifugation or filtration of a re-suspended Fraction II+III paste. Advantageously, according to the methods provided herein, industrial-scale preparation of Factor H can be achieved without the need for additional input plasma or the redesign and regulatory re-approval of existing manufacturing processes for other commercially important plasma-derived blood products, such as IgG gamma globulins for intravenous (IVIG) or subcutaneous administration.

In one aspect, the present invention provides a method for preparing an enriched Factor H composition from plasma by extracting Factor H from a Fraction II+III filter cake. In a related embodiment, the method involves the adsorption of Factor H from a suspended Fraction II+III precipitate and separation from the suspension.

In a preferred embodiment, a method is provided for preparing an enriched Factor H composition from plasma, the method comprising the steps of: (a) precipitating proteins from a cryo-poor plasma fraction, in a first precipitation step, with between about 6% and about 10% alcohol at a pH of between about 7.0 and about 7.5 to obtain a first precipitate and a first supernatant; (b) precipitating Factor H from the first supernatant, in a second precipitation step, with between about 20% and about 30% alcohol at a pH of between about 6.7 and about 7.3 to form a second precipitate; (c) re-suspending the second precipitate to form a suspension; (d) mixing finely divided silicon dioxide ($SiO_2$) with the suspension from step (c); (e) separating the suspension to form a filter cake and a supernatant; and (f) extracting Factor H from the filter cake with a Factor H extraction buffer, thereby preparing an enriched Factor H composition. In a preferred embodiment, the filter cake is separated from the supernatant by filtering the suspension through a filter press containing a suitable filter. In one embodiment, Factor H can be extracted by re-circulating an extraction buffer through a filter press containing a filter cake.

In a second aspect, the present invention provides a method for preparing an enriched Factor H composition from plasma by extracting Factor H from a Fraction I precipitate.

In a preferred embodiment, a method is provided for preparing an enriched Factor H composition from plasma, the method comprising the steps of: (a) precipitating proteins from a cryo-poor plasma fraction, in a first precipitation step, with between about 6% and about 10% alcohol at a pH of between about 7.0 and about 7.5 to obtain a first precipitate and a first supernatant; and (b) extracting Factor H from the precipitate with a Factor H extraction buffer, thereby preparing an enriched Factor H composition.

In one aspect, a method is provided for preparing an enriched Factor H composition from plasma, by extracting Factor H from a pool of two or more manufacturing byproduct fractions created by a process designed to provide a second blood protein, for example, IgG gamma globulins. In one embodiment, the method comprises pooling a Fraction I precipitate and a Fraction II+III filter cake formed during the manufacture of IgG gamma globulins (e.g., IVIG) and extracting Factor H from the pooled fractions.

In a related aspect, Factor H extracted from two or more manufacturing byproduct fractions created by a process designed to provide a second blood protein, for example, IgG gamma globulins, is pooled and further purified. In one embodiment, Factor H extracted from a Fraction I precipitate and a Fraction II+III filter cake is pooled and subsequently purified further.

In certain embodiments, an enriched Factor H composition may be further purified subsequent to extraction from a Fraction I precipitate and/or Fraction II+III filter cake. Various methods are available for further purifying Factor H, including without limitation, additional precipitation steps or fractionations, affinity chromatography, ion exchange chromatography, hydrophobic interaction chromatography, size exclusion chromatography, solvent/detergent (S/D) treatment, nanofiltration, ultrafiltration, diafiltration, and the like.

In one embodiment, the method further comprises precipitating impurities from an enriched Factor H composition. In certain embodiments, this step comprises precipitating at least one impurity, for example a lipid or protein, from the composition and then separating the precipitate from the supernatant containing Factor H. Optionally, Factor H can then be precipitated from the supernatant in a separate precipitation.

Advantageously, precipitation and subsequent re-suspension of Factor H from an enriched composition allows for the reduction of volume prior to additional purification steps, such as chromatography or nanofiltration. In one embodiment, the enriched Factor H composition may be further purified subsequent to extraction from a Fraction I precipitate or Fraction II+III filter cake by precipitating Factor H out of the enriched composition. In certain embodiments, an enriched Factor H composition may be subjected to a first precipitation step to remove at least one impurity from the composition, as described above, and then to a second precipitation step to precipitate and recover Factor H.

In one embodiment, a Factor H composition extracted from a Fraction I precipitate or Fraction II+III filter cake is further enriched by precipitating impurities from the enriched Factor H composition, in a second or third precipitation step, thereby forming a supernatant containing Factor H. Subsequently, Factor H may further be enriched by precipitating Factor H, in a third or fourth precipitation step. In one embodiment, Factor H is precipitated with between about 20% and about 25% alcohol at a pH of between about 6.0 and about 8.0.

In certain embodiments, the method for preparing an enriched Factor H composition further comprises at least one, preferably two, chromatographic steps to further enrich the purity of the composition. Generally, any suitable chromatographic method may be employed to further enrich the Factor H composition extracted from a Fraction I precipitate or Fraction II+III filter cake. In certain embodiments, prior to chromatographic enrichment, the extracted Factor H composition will be subjected one or more additional precipitation steps, as described above, to reduce the impurities present in the composition, reduce the load volume for the chromatographic step, and/or exchange the buffer of the composition.

In certain embodiments, a Factor H composition may be further enriched by a chromatographic step comprising anion exchange chromatography (AEC), cation exchange chromatography (CEC), heparin affinity chromatography, hydrophobic exchange chromatography (HIC), hydroxyapatite chromatography (HAP), immunoaffinity chromatography, size exclusion chromatography (i.e., gel filtration), or other suitable chromatographic step. Chromatographic steps may be performed in either batch or column mode.

In a preferred embodiment, the method comprises the use of anion exchange chromatography and heparin affinity chromatography.

In certain embodiments, the methods provided herein for the preparation of an enriched Factor H composition will further include at least one, preferably at least two, most preferably at least three, viral inactivation or removal steps. Non-limiting examples of viral inactivation or removal steps that may be employed with the methods provided herein include, solvent detergent treatment (Horowitz et al., *Blood Coagul Fibrinolysis* 1994 (5 Suppl 3):S21-S28 and Kreil et al., *Transfusion* 2003 (43):1023-1028, both of which are herein expressly incorporated by reference in their entirety for all purposes), nanofiltration (Hamamoto et al., *Vox Sang* 1989 (56)230-236 and Yuasa et al., *J Gen Virol.* 1991 (72 (pt 8)):2021-2024, both of which are herein expressly incorporated by reference in their entirety for all purposes), low pH incubation at high temperatures (Kempf et al., *Transfusion* 1991 (31)423-427 and Louie et al., *Biologicals* 1994 (22):13-19), and heat treatment of lyophilized Factor H compositions (Piszkiewicz et al., *Thromb Res.* 1987 Jul. 15; 47(2):235-41; Piszkiewicz et al., *Curr Stud Hematol Blood* Transfus. 1989; (56):44-54; Epstein and Fricke, *Arch Pathol Lab Med.* 1990 March; 114(3):335-40)

In a preferred embodiment, the present invention provides a method of preparing a virally safe enriched Factor H composition comprising (i) extracting Factor H from a Fraction II+III filter cake, (ii) performing a first precipitation step to precipitate at least one impurity from the Factor H composition, (iii) performing a second precipitation step to precipitate Factor H from the composition, and (iv) performing at least one viral inactivation or removal step, thereby preparing a virally safe enriched Factor H composition.

In another preferred embodiment, the invention provides a method of preparing a virally safe enriched Factor H composition comprising (i) extracting Factor H from a Fraction I precipitate, (ii) performing a first precipitation step to precipitate at least one impurity from the Factor H composition, (iii) performing a second precipitation step to precipitate Factor H from the composition, and (iv) performing at least one viral inactivation or removal step, thereby preparing a virally safe enriched Factor H composition.

In one aspect, Factor H isolated from material otherwise discarded during the manufacture of other commercially important blood products by plasma fractionation, e.g., a Fraction I precipitate or Fraction II+III filter cake, may be further enriched by chromatography with a series of step elutions that are amenable to a large scale manufacturing process. In one embodiment, DEAE Sepharose™ and Heparin Sepharose™ chromatography resins are used with a suitable buffer system, for example, one containing 25 mM Tris (pH 8.0) and 5 mM EDTA.

The chromatographic enrichment of a Factor H composition can be modified to use buffer systems other than Tris/EDTA at pH 8.0. These processes can be adapted for buffers and solutions commonly used in manufacturing of biopharmaceuticals. An example is a purification scheme using phosphate buffer at pH 7.0. The key parameter to successful purification is manipulation of conductivity or ionic strength to achieve separation of the desired compound. If pH of the buffer system is maintained at pH 8.0, the conductivity of the elution buffers must be matched to the purification process described here. If the pH of the buffer system is changed, some adjustment of the ionic strength will be needed which can be done with standard techniques used in optimization of chromatographic processes.

In one aspect, the present invention provides a method of preparing Factor H from pooled human plasma comprising (a) performing Cohn fractionation to obtain Fraction II+III precipitates and preparing a suspension of the combined precipitates, (b) filtering the re-suspended Fraction II+III precipitates to obtain the Aerosil® filter cake discard left behind after filtration of the Fraction II+III suspension; (c) extracting the filter cake according to a method comprising the steps of: (i) dissolving the filter cake in a suitable buffer of appropriate ionic strength for a time sufficient to dissolve the protein caked on said filter cake; (ii) diluting said dissolved protein with additional buffer, (iii) removing debris from the diluted protein, (iv) purifying Factor H protein from said diluted protein preparation by subjecting the diluted protein to ultrafiltration on a 0.45 µm filter to produce a filtrate containing Factor H; (v) subjecting the filtrate containing Factor H to anion exchange chromatography using a NaCl gradient (50-500 mM) in the running buffer to produce a pooled crude Factor H fraction; and (vi) purifying Factor H from said crude Factor H preparation by Heparin Sepharose™ chromatography using a gradient of NaCl (50-500 mM).

In one embodiment of the method of preparing Factor H, the anion exchange chromatography uses DEAE Sepharose™ as the anion exchange resin.

In another embodiment of the method of preparing Factor H, the purified Factor H is an active Factor H preparation that is composed of a mixture of Tyr-402 and His-402 isoforms in the range 50%±20% His-402: 50%±20% Tyr-402.

In another embodiment of the method of preparing Factor H, the method further comprises placing Factor I precipitate with the filter cake in step (c)(i).

In another embodiment of the method of preparing Factor H, the buffer in step (c)(v) and/or (c)(vi) is 25 mM TRIS/5 mM EDTA/50 mM NaCl having a pH of 8.0.

In another embodiment of the method of preparing Factor H, the method further comprises lyophilizing the Factor H produced in step (c)(vi).

In another embodiment of the method of preparing Factor H, the anion exchange chromatography uses a first buffer having an ionic strength equal to a NaCl concentration of about 50 mM to about 65 mM for binding Factor H to the resin and a second buffer having an ionic strength equal to a sodium chloride concentration of at least about 100 mM for eluting the Factor H from the resin. In a preferred embodiment, the elution buffer has an ionic strength equal to a sodium chloride concentration of between about 100 mM and about 120 mM. Optionally, a subsequent heparin affinity chromatography step may then be performed to further enrich the Factor H composition. The heparin affinity step consists of adjusting the ionic strength of the Factor H composition to an ionic strength equal to a NaCl concentration of about 50 mM or less for binding Factor H to the resin, optionally washing the column with a buffer having an ionic strength equal to a sodium chloride concentration of about 50 mM NaCl to about 75 mM NaCl, preferably about 50 mM NaCl or less, and eluting Factor H from the resin with a buffer having an ionic strength equal to a sodium chloride concentration of between about 100 mM and about 250 mM NaCl.

An alternative purification process consists of taking the Fraction I precipitate or Fraction II+III filter cake extract at pH 8 and adjusting the salt concentration to an ionic strength equal that of an NaCl concentration of between about 120 and 150 mM and then contacting the composition with an anion-exchange resin (e.g., DEAE Sepharose™) to bind unwanted proteins in the extract. The Factor H does not bind to the resin and can be recovered in a flow through fraction, which is collected for further processing. The ionic strength of the Factor H pool is then adjusted to equal that of a sodium chloride concentration of no more than about 75 mM, preferably no more than about 50 mM, to bind the Factor H to a heparin affinity resin. The resin is eluted to recover Factor H with a buffer having an ionic strength equal to a sodium chloride concentration of between about 90 mM and about 250 mM, preferably between about 100 mM and about 200 mM. Optionally, the ionic strength of the Factor H eluate may be adjusted to equal a sodium chloride concentration of no more than about 75 mM, preferably no more than about 65 mM, most preferably no more than about 50 mM to bind the Factor H to a second anion exchange resin, which can be the same or a different resin as the first anion exchange resin, to remove impurities from the pool that have low affinity for the resin. The Factor H is then eluted from the resin with a buffer having an ionic strength equal to at least about 100 mM sodium chloride, more preferably at least about 120 mM.

In one embodiment, a Factor H composition is further enriched by (i) binding impurities to a an anion exchange resin under conditions such that Factor H does bind to the resin and is collected in the flow through fraction; (ii) binding Factor H from the flow through fraction to a heparin affinity resin; (iii) eluting Factor H from the heparin affinity resin to form an eluate; (iv) binding Factor H from the eluate to an anion exchange resin; and (v) eluting Factor H from the anion exchange resin, thereby further purifying Factor H.

Purification from Fraction I or the Aerosil filter cake could be performed by several alternative methods, including immunoaffinity purification, variant resins for anion exchange chromatography (e.g. DEAE Sephacel™, etc) and inclusion of size exclusion chromatography (e.g., Sephacryl™ S-300) as an optional polishing step, if necessary. Hydrophobic interaction chromatography (e.g., Phenyl Sepharose™) may also be employed as part of the above purification scheme. These Factor H purification schemes have all been described in the prior art. Additionally, the Aerosil® filter cake may be 'washed in place' with a Factor H eluting buffer of sufficient ionic strength to dissolve Factor H from the filter cake while maintaining its functional activity (such as the 25 mM Tris; 200 mM NaCl; 5 mM EDTA; pH 8 buffer used above). This material would then be processed via downstream chromatography (such as that described above) to purify the Factor H to homogeneity.

In one aspect, a method is provided for preparing an enriched Factor H composition from plasma comprising the steps of: (a) extracting Factor H from a Fraction I precipitate and/or a Fraction II+III filter cake, to form a Factor H extract; and (b) precipitating impurities from the Factor H extract to form a supernatant containing Factor H, thereby preparing an enriched Factor H composition.

A. Alcohol Precipitation and Chromatographic Fractionation Methods

In one aspect, the present invention provides methods for the preparation of enriched compositions of Factor H from material otherwise discarded during the manufacturing process of a second blood factor. In an exemplary embodiment, Factor H can be recovered from fractions generated by the manufacturing process for plasma-derived IgG compositions, such as IgG compositions formulated for intravenous (i.e., IVIG), subcutaneous, and/or intramuscular administration.

In a preferred embodiment, a method for the preparation of an enriched composition of Factor H is provided, the method comprising (i) extracting Factor H from a Fraction I precipitate and/or Fraction II+III filter cake, (ii) optionally performing a first precipitation step to precipitate at least one impurity from the Factor H composition, (iii) optionally performing a second precipitation step to precipitate Factor H from the composition, (iv) optionally performing at least one ion exchange chromatography step, (v) optionally performing at least one heparin affinity chromatography step; and (vi) performing at least one viral inactivation or removal step.

In one embodiment, a method for the preparation of an enriched composition of Factor H from material otherwise discarded during an IgG manufacturing process comprises one or more of the following steps.

1. Preparation of Cryo-Poor Plasma

In certain embodiments, the starting material used for the preparation of Factor H and IgG compositions generally consists of either recovered plasma (i.e., plasma that has been separated from whole blood ex vivo) or source plasma (i.e., plasma collected via plasmapheresis). The purification process typically starts with thawing previously frozen pooled plasma, which has already been assayed for safety and quality considerations, although fresh plasma may also be used. In certain embodiments thawing is typically carried out at a temperature not higher than at or about 6° C. After complete thawing of the frozen plasma at low temperature, centrifugation is performed in the cold (e.g., ≦6° C.) to separate solid cryo-precipitates from the liquid supernatant. Alternatively, the separation step can be performed by filtration rather than centrifugation. The liquid supernatant (also referred to as "cryo-poor plasma," after cold-insoluble proteins removed by centrifugation from fresh thawed plasma) is then processed in the next step. Various additional steps can be taken at this juncture for the isolation of other blood coagulation factors and inhibitors, e.g., Factor Eight Inhibitor Bypass Activity (FEIBA), Factor IX-complex, Factor VII, or Antithrombin III-complex.

2. First Precipitation Step—Fraction I Precipitation

The cryo-poor plasma solution is then typically cooled to about 0±1° C. and the pH is adjusted to between at or about 7.0 and at or about 7.5. In another embodiment, the pH is adjusted to between at or about 7.1 and at or about 7.3. In one embodiment, the pH of the cryo-poor plasma is adjusted to a pH of at or about 7.2. Pre-cooled ethanol is then added while the plasma is stirred to a target concentration of between at or about 6% and at or about 10%. In a preferred embodiment, ethanol is added to a target concentration of between at or about 7% and at or about 9%. In a more preferred embodiment, ethanol is added to a target concentration of at or about 8% (v/v). At the same time the temperature is further lowered to between at or about −4° C. and at or about 0° C. In a preferred embodiment, the temperature is lowered to at or about −2° C., to precipitate components such as fibrinogen. Typically, the precipitation event will include a hold time of at least about 1 hour, although shorter or longer hold times may also be employed. Subsequently, the supernatant (Supernatant I) is then separated from the precipitate (Fraction I precipitate) by centrifugation, filtration, or another suitable method.

Typically, the Fraction I precipitation step is performed to remove fibrinogen and other impurities in the manufacturing process of plasma-derived blood factors such as IgG and albumin. Advantageously, it was found that a significant fraction of Factor H is present in this precipitate. For example, Example 1 demonstrates that more than 180 grams of Factor H, nearly 10% of the total content found in the cryo-poor plasma starting material (Cohn pool), is present in the Fraction I precipitate of an industrial-scale plasma fractionation. Accordingly, in one embodiment, Factor H is extracted from the Fraction I precipitate. Suitable buffers and methods for the extraction of Factor H from the Factor I precipitate are provided herein.

As compared to conventional methods employed as a first fractionation step for cryo-poor plasma (Cohn et al., supra; Oncley et al., supra), the present invention provides, in several embodiments, methods that result in improved yields of plasma factors (e.g., Factor H, IgG, etc.). In one embodiment, the precipitating alcohol is added in a fashion that finely disperses or that rapidly disperses the alcohol at the point of addition. In one embodiment, the alcohol is added by spraying. In a second embodiment, the alcohol is added from below or directly adjacent to a stirring apparatus, for example, a propeller. Addition of alcohol by any of these mechanisms avoids local over-concentration of alcohol which occurs, for example, at the point of fluent addition and results in the irreversible denaturation of proteins and/or precipitation of proteins that would otherwise be recovered in the supernatant.

In another embodiment, one or more pH modifying agent is added in a fashion that finely disperses or that rapidly disperses the pH modifying agent at the point of addition. In one embodiment, the pH modifying agent is added by spraying. In a second embodiment, the pH modifying agent is added from below or directly adjacent to a stirring apparatus, for example, a propeller. In a third embodiment, the pH modifying agent is added by sprinkling a solid pH modifying agent over a delocalized area.

In yet another embodiment, the pH of the solution is adjusted after addition of the alcohol. In a related embodiment, the pH of the solution is adjusted during the addition of the alcohol. In one embodiment, the pH of the solution is maintained at the desired pH during the precipitation hold or incubation time by continuously adjusting the pH of the solution. In a preferred embodiment, the alcohol is ethanol.

In certain embodiments, the pH of the solution is adjusted to between at or about 7.0 and about at or 7.5 after the addition of the precipitating alcohol. In other embodiments, the pH of the solution is adjusted to between at or about 7.1 and at or about 7.3 after addition of the precipitating alcohol. In yet other embodiments, the pH of the solution is adjusted to at or about 7.0 or at or about 7.1, 7.2, 7,3, 7.4, or 7.5 after addition of the precipitating alcohol. In a particular embodiment, the pH of the solution is adjusted to at or about 7.2 after addition of the precipitating alcohol. As such, in certain embodiments, a reduced amount of blood factor is irreversibly lost during the first precipitation step due to protein denaturation, as compared to an analogous precipitation step in which the pH of the solution is adjusted prior to but not after addition of the precipitating alcohol.

In other certain embodiments, the precipitating alcohol and/or the solution used to adjust the pH is added by spraying, rather than by fluent addition. As such, in certain embodiments, a reduced amount of blood factor is irreversibly lost during the first precipitation step due to protein denaturation, as compared to an analogous precipitation step in which the alcohol and/or solution used to adjust the pH is introduced by fluent addition.

In yet other embodiments, the pH of the solution is adjusted after addition of the precipitating alcohol and by adding the precipitating alcohol and/or a solution used to adjust the pH by spraying, rather than by fluent addition. In a particular embodiment, the pH of the solution is adjusted to at or about 7.2 after addition of the precipitating alcohol and by adding the precipitating alcohol and/or the solution used to adjust the pH by spraying, rather than by fluent addition.

3. Second Precipitation Step—Fraction II+III Precipitation

In order to enrich the content and purity of the relevant blood factors present in the Fraction I supernatant (e.g., Factor H, IgG), the Fraction Supernatant I is subjected to a second precipitation step, which is a Cohn-Oncley Fraction II+III type fractionation. Generally, the pH of the solution is adjusted to a pH of between at or about 6.6 and at or about 7.2. In a preferred embodiment, the pH of the solution is adjusted to between at or about 6.6 and at or about 6.8. In a more preferred embodiment, the pH of the solution is adjusted to a pH of at or about 6.7. Alcohol, preferably ethanol, is then added to the solution while being stirred to a final concentration of between at or about 20% and at or about 30% (v/v) to precipitate Factor H and IgG present in the fraction. In a preferred embodiment, alcohol is added to a final concentration of at or about 25% (v/v) to precipitate the IgG in the fraction.

Prior to or concomitant with alcohol addition, the solution is further cooled to between at or about −5° C. and at or about −9° C. In a preferred embodiment, the solution is cooled to a temperature at or about −7° C. After completion of the alcohol addition, the pH of the solution is immediately adjusted to between at or about 6.6 and at or about 7.2. In a preferred embodiment, the pH of the solution is adjusted to between at or about 6.6 and at or about 6.8. In a particular embodiment, the pH of the solution is adjusted to at or about 6.9. Typically, the precipitation event will include a hold time of at least at or about 10 hours, although shorter or longer hold times may also be employed. Subsequently, the precipitate (Fraction II+III), which contains the majority of the Factor H and IgG content of the cryo-poor plasma, is separated from the supernatant by centrifugation, filtration, or another suitable method and collected. As compared to conventional methods employed as a second fractionation step for cryo-poor plasma (Cohn et al., supra; Oncley et al., supra), the present invention provides, in several embodiments, methods that result in improved blood factor yields in the Fraction II+III precipitate. In a related embodiment, the present invention provides methods that result in a reduced loss of Factor H and IgG in the Fraction II+III supernatant.

As compared to conventional methods employed as a second fractionation step for cryo-poor plasma (Cohn et al., supra; Oncley et al., supra), the present invention provides, in several embodiments, methods that result in improved blood factor yields in the Fraction II+III precipitate. In one embodiment, the precipitating alcohol is added in a fashion that finely disperses the alcohol or that rapidly disperses the alcohol at the point of addition. In one embodiment, the alcohol is added by spraying. In a second embodiment, the alcohol is added from below or directly adjacent to a stirring apparatus, for example, a propeller.

In another embodiment, one or more pH modifying agent is added in a fashion that finely disperses or that rapidly disperses the pH modifying agent at the point of addition. In one embodiment, the pH modifying agent is added by spraying. In a second embodiment, the pH modifying agent is added from below or directly adjacent to a stirring apparatus, for example, a propeller. In a third embodiment, the pH modifying agent is added by sprinkling a solid pH modifying agent over a delocalized area.

In yet another embodiment, the pH of the solution is adjusted after addition of the alcohol. In a related embodiment, the pH of the solution is adjusted during addition of the alcohol. In one embodiment, the pH of the solution is maintained at the desired pH during the precipitation hold or incubation time by continuously adjusting the pH of the solution. In a preferred embodiment, the alcohol is ethanol.

In one embodiment, the temperature of the Fraction II+III precipitation step is between at or about −7° C. and at or about −9° C. In a related embodiment, the concentration of alcohol (e.g., ethanol) used in the Fraction II+III precipitation step is at or about 25% (v/v) and the temperature is between at or about −7° C. and at or about −9° C. In comparison, both Cohn et al. and Oncley et al. perform precipitation at −5° C. and Oncley et al. use 20% alcohol, in order to reduce the level of contaminants in the precipitate. Advantageously, the methods provided herein allow for maximal Factor H and IgG yield without high levels of contamination in the final product.

In another embodiment, the precipitation step is performed at a temperature between at or about −7° C. and at or about −9° C. In one embodiment, the precipitation step is performed at a temperature of at or about −7° C. In another embodiment, the precipitation step is performed at a temperature of at or about −8° C. In another embodiment, the precipitation step is performed at a temperature of at or about −9° C.

In certain embodiments, the alcohol concentration of the precipitation step is between at or about 20% and at or about 30%, preferably between at or about 23% and at or about 27%. In a preferred embodiment, the alcohol concentration is between at or about 24% and at or about 26%. In another preferred embodiment, the alcohol concentration is at or about 25%. In other embodiments, the alcohol concentration may be at or about 20%, 21%, 22%, 23%, 24%, 25%, 26%, 27%, 28%, 29% or 30%. In a particular embodiment, the second precipitation step is performed at a temperature of at or about −7° C. with an alcohol concentration of at or about 25%. In one embodiment, the alcohol is ethanol.

It has been discovered that when the pH of the solution is adjusted to a pH of about 6.9 prior to addition of the precipitating alcohol, the pH of the solution shifts from 6.9 to between about 7.4 and about 7.7, due in part to protein precipitation. As the pH of the solution shifts away from 6.9, precipitation of IgG becomes less favorable and the precipitation of certain contaminants becomes more favorable. Advantageously, the inventors have found that by adjusting the pH of the solution after addition of the precipitating alcohol, that higher percentages of IgG is recovered in the Fraction II+III precipitate. In one embodiment, the pH of the solution is maintained at the desired pH during the precipitation hold or incubation time by continuously adjusting the pH of the solution. In a preferred embodiment, the alcohol is ethanol.

Accordingly, in one aspect, reduced amounts of Factor H and/or IgG are lost in the supernatant fraction of the Fraction II+III precipitation step. In other words, increased percentages of the starting Factor H and/or IgG are present in the Fraction II+III precipitate. In certain embodiments, the pH of the solution is adjusted to between at or about 6.6 and at or about 7.2 immediately after or during the addition of the precipitating alcohol. In another embodiment, the pH of the solution is maintained between at or about 6.6 and at or about 7.2 continuously during the precipitation incubation period. In other embodiments, the pH of the solution is adjusted to between at or about 6.8 and at or about 7.0 immediately after or during the addition of the precipitating alcohol, or to a pH of at or about 6.7, 6.8, 6.9, 7.0, or 7.1 immediately after or during the addition of the precipitating alcohol. In a particular embodiment, the pH of the solution is adjusted to at or about 6.9 immediately after or during the addition of the precipitating alcohol. In certain embodiments, the pH of the solution is maintained at between at or about 6.8 and at or about 7.0 continuously during the precipitation incubation period, or at a pH of at or about 6.9 continuously during the precipitation incubation period. As such, in certain embodiments, a reduced amount of Factor H and/or IgG is lost in the supernatant fraction of the second precipitation step as compared to an analogous precipitation step in which the pH of the solution is adjusted prior to but not after addition of the precipitating alcohol or to an analogous precipitation step in which the pH of the solution is not maintained during the entirety of the precipitation incubation period.

In another embodiment, both the precipitating alcohol and the solution used to adjust the pH are added by spraying, rather than by fluent addition. As such, in certain embodiments, a reduced amount of Factor H and/or IgG is lost in the supernatant fraction of the second precipitation step as compared to an analogous precipitation step in which the alcohol and/or solution used to adjust the pH is introduced by fluent addition.

In another embodiment, the pH of the solution is adjusted to between at or about 6.7 and at or about 7.1 immediately after or during the addition of the precipitating alcohol by spray addition of either or both the alcohol and pH modifying agent. In another embodiment, the pH of the solution is adjusted to at or about 6.9 immediately after or during the addition of the precipitating alcohol by spray addition of either or both the alcohol and pH modifying agent. In one embodiment, the pH of the solution is maintained at or about between 6.7 and 7.1 by continuously adjusting the pH during the precipitation incubation period by adding the precipitating alcohol and/or the solution used to adjust the pH by spraying, rather than by fluent addition. In another embodiment, the pH of the solution is maintained at or about 6.9 by continuously adjusting the pH during the precipitation incubation period by adding the precipitating alcohol and/or the solution used to adjust the pH by spraying, rather than by fluent addition.

In another particular embodiment, the precipitation step is performed at or about a temperature between −7° C. and −9° C., or at or about −7° C. with an alcohol concentration of at or about between 23% and 27%, or at or about 25%. In one embodiment, Factor H and IgG are precipitated at a temperature of at or about −7° C. with at or about 25% ethanol added by spraying, wherein the pH of the solution is adjusted to at or about 6.9 after addition of the precipitating alcohol. In yet another embodiment, the pH of the solution is maintained at or about 6.9 for the entirety of the precipitation incubation or hold time.

4. Extraction of the Fraction II+III Precipitate

In order to solubilize the Factor H and IgG content of the Fraction II+III precipitate, a cold extraction buffer is used to re-suspend the Fractionation II+III precipitate at a typical ratio of at or about 1 part precipitate to 15 parts of extraction buffer. In another aspect, a cold extraction buffer is used to re-suspend the Fractionation II+III precipitate at a typical ratio of at or about 1 part precipitate to 20 parts of extraction buffer. Other suitable re-suspension ratios may be used, for example at a range of at or about between 1:4 and 1:40, or at or about between 1:8 and 1:30, or at or about between 1:10 and 1:20, or at or about between 1:12 and 1:18, or at or about between 1:13 and 1:17, or at or about between 1:14 and 1:16. In certain embodiments, the re-suspension ratio may be at or about 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, or higher. In a preferred embodiment, the Fraction II+III paste is re-suspended at or about a ratio of 1 part precipitate to 15 parts extraction buffer. In another preferred embodiment, the Fraction II+III paste is re-suspended at or about a ratio of 1 part precipitate to 20 parts extraction buffer.

Suitable solutions for the extraction of the II+III precipitate will generally have a pH at or about between 4.0 and 5.5. In certain embodiments, the solution will have a pH at or about between 4.3 and 4.7, in other embodiments, the extraction solution will have a pH of at or about 4.0, 4.1, 4.2, 4.3, 4.4, 4.5, 4.6, 4.7, 4.8, 4.9, 5.0, 5.1, 5.2, 5.3, 5.4, or 5.5. In a preferred embodiment, the pH of the extraction buffer will be at or about 4.3. In another preferred embodiment, the pH of the extraction buffer will be at or about 4.5. In another preferred embodiment, the pH of the extraction buffer will be at or about 4.7. Generally, these pH requirements can be met using a buffering agent selected from, for example, acetate, citrate, monobasic phosphate, dibasic phosphate, mixtures thereof, and the like. Suitable buffer concentrations typically range from about 2.5 to about 100 mM, or from about 5 to about 50 mM, or about 2.5, 5, 10, 15, 20, 25, 30, 35, 40, 45, 50, 55, 60, 65, 70, 75, 80, 85, 90, 95, or 100 mM buffering agent.

The extraction buffer will preferably have a conductivity of at or about between 0.5 mS·cm$^{-1}$ and 2.0 mS·cm$^{-1}$. For example, in certain embodiments, the conductivity of the extraction buffer will be at or about 0.5 mS·cm$^{-1}$, or at or about 0.6, 0.7, 0.8, 0.9, 1.0, 1.1, 1.2, 1.3, 1.4, 1.5, 1.6, 1.7, 1.8, 1.9, or at or about 2.0 mS·cm$^{-1}$. One of ordinary skill in the art will know how to generate extraction buffers having an appropriate conductivity.

In one particular embodiment, an exemplary extraction buffer may contain at or about 5 mM monobasic sodium phosphate and at or about 5 mM acetate at a pH of at or about 4.5±0.2 and conductivity of at or about 0.7 to 0.9 mS/cm.

Generally, the extraction is performed at or about between 0° C. and 20° C., preferably at or about between 2° C. and 8° C. In certain embodiments, the extraction may be performed at or about 0° C., 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., or 20° C. In a particular embodiment, the extraction is performed at or about between 2° C. and 10° C. Typically, the extraction process is performed under continuous stirring until all soluble components of the II+III paste are brought into solution. In certain embodiments, the extraction will proceed for at or about between 60 and 300 minutes, or for at or between 120 and 240 min, or for at or about between 150 and 210 minutes, while the suspension is continuously stirred. In certain embodiments, the extraction process will proceed for at or about 60, 70, 80, 90, 100, 110, 120, 130, 140, 150, 160, 170, 180, 190, 200, 210, 220, 230, 240, 250, 260, 270, 280, 290, or at or about 300 minutes. In a preferred embodiment, the extraction process will proceed for at least 60 minutes with continuous stirring.

In one embodiment, the extraction buffer will contain at or about 5 mM monobasic sodium phosphate, 5 mM acetate, and 0.051% to 0.06% glacial acetic acid (v/v). In a preferred embodiment, the Fraction II+III precipitate is extracted with a paste to buffer ratio of at or about 1:15 at a pH of at or about 4.5±0.2.

In one embodiment, the pH of the solution is maintained for the duration of the extraction process. In one embodiment, the pH of the solution is maintained at or about between 4.1 and 4.9 for the duration of the extraction process. In a preferred embodiment, the pH of the solution is maintained at or about between 4.2 and 4.8 for the duration of the extraction process. In a more preferred embodiment, the pH of the solution is maintained at or about between 4.3 and 4.7 for the duration of the extraction process. In another preferred embodiment, the pH of the solution is maintained at or about between 4.4 and 4.6 for the duration of the extraction process. In yet another preferred embodiment, the pH of the solution is maintained at or about 4.5 for the duration of the extraction process.

5. Pretreatment and Extraction of Factor H from the Fraction II+III Suspension

Advantageously, it has been found that pretreatment of solubilized Fraction II+III precipitate with finely divided silicon dioxide ($SiO_2$) significantly reduces impurities, such as lipids, fibrinogen, amidolytic activity, prekallikren activity, and lipoproteins, from the IgG manufacturing process. Unexpectedly, the inventors have found that the majority of Factor H found in the Cohn pool staring material is drawn into the Fraction II+III filter cake after treatment with silicon dioxide and filter aid. For example, Example 1 demonstrates that more than 1.74 kilograms of Factor H, more than 80% of the total Factor H content of the cryo-poor plasma starting material (Cohn pool), is present in the Fraction II+III precipitate of an industrial-scale plasma fractionation (about 3000 L), yet is absent completely in the filtrate after the Fraction II+III suspension is treated with silicon dioxide and filter aid addition. Furthermore, Example 2 demonstrates that Factor H is not irreversibly lost and can be extracted from the Fraction II+III filter cake. Even more importantly, as demonstrated in Example 4, Factor H extracted from the filter cake maintains equivalent Factor I cofactor and C3/C5 convertase inhibition activities as compared to a commercial preparation of Factor H (CompTech).

Accordingly, in one embodiment, Factor H is extracted from a filter cake after filtration or centrifugation of a Fraction II+III paste suspension in the presence of finely divided silicon dioxide (e.g., Aerosil®) and/or filter aid.

In certain embodiments, Fraction II+III precipitate that has been extracted with a suitable dissolution buffer will be treated with at or about between 5 mg and 100 mg finely divided silicon dioxide per gram of suspended Fraction II+III precipitate. In a preferred embodiment, the Fraction II+III suspension will be treated with at or about between 20 mg and 80 mg finely divided silicon dioxide per gram of suspended Fraction II+III precipitate. In a more preferred embodiment, the Fraction II+III suspension will be treated with at or about between 40 mg and 60 mg finely divided silicon dioxide per gram of suspended Fraction II+III precipitate. In another preferred embodiment, the Fraction II+III suspension will be treated with at or about 50 mg finely divided silicon dioxide per gram of suspended Fraction II+III precipitate. In certain embodiments, finely divided silicon dioxide is added at a concentration of at or about between 20 g/kg II+III paste and 100 g/kg II+III paste (i.e., for a Fraction II+III precipitate that is extracted at a ratio of 1:15, finely divided silicon dioxide should be added at a concentration at or about between 20 g/16 kg II+III suspension and 100 g/16 kg II+III suspension, or at a final concentration at or about between 0.125% (w/w) and 0.625% (w/w)). In certain embodiments, the finely divided silicon dioxide may be added at a concentration of at or about 5 g/kg II+III paste, or at or about 10, 15, 20, 25, 30, 35, 40, 45, 50, 55, 60, 65, 70, 75, 80, 85, 90, 95, or 100 g/kg II+III paste. In one specific embodiment, finely divided silicon dioxide is added to the Fraction II+III suspension to a final concentration of at or about 40 g/16 kg II+III suspension. In a preferred embodiment, the finely divided silicon dioxide used is Aerosil® 380 or an equivalent thereof.

Generally, the finely divided silicon dioxide treatment will be performed at a temperature at or about between 0° C. and 20° C., preferably at or about between 2° C. and 8° C. In certain embodiments, the treatment may be performed at or about 0° C., 1° C., 2° C., 3° C., 4° C., 5° C. 6° C., 7° C., 8° C., 9° C., 10° C., 11° C., 12° C., 13° C. 14° C., 15° C., 16° C., 17° C., 18° C., 19° C., or 20° C. Typically, the Fraction II+III suspension will be stirred with finely divided silicon dioxide for at least 15 minutes. In certain embodiments, the Fraction II+III suspension will be stirred with finely divided silicon dioxide for at least 10, 15, 20, 30, 40, 50, 60, 70, 80, 90, 100, 110 minutes, or at least 1, 2, 3, 4, 5, 6, or more hours. In a preferred embodiment, the Fraction II+III suspension will be stirred with finely divided silicon dioxide for at or about between 30 and 60 minutes. In another preferred embodiment, the Fraction II+III suspension will be stirred with finely divided silicon dioxide for at least 30 minutes.

In certain embodiments, filter aid, for example Celpure C300 (Celpure) or Hyflo-Supper-Cel (World Minerals), will be added to facilitate depth filtration. Filter aid can be added at a final concentration of from about 0.1 kg/kg Fraction II+III precipitate to about 0.7 kg/kg Fraction II+III precipitate, or from about 0.2 kg/kg Fraction II+III precipitate to about 0.6 kg/kg Fraction II+III precipitate, or from about 0.3 kg/kg Fraction II+III precipitate to about 0.5 kg/kg Fraction II+III precipitate. In certain embodiments, the filter aid will be added at a final concentration of about 0.1 kg/kg Fraction II+III precipitate, or about 0.2, 0.3, 0.4, 0.5, 0.6, or 0.7 kg/kg Fraction II+III precipitate.

In order to remove the non-solubilized and adsorbed fraction of the Fraction II+III precipitate (i.e., the Fraction II+III filter cake) after silicon dioxide treatment, the suspension is filtered, typically using depth filtration. Depth filters that may be employed in the methods provided herein include, metallic, glass, ceramic, organic (such as diatomaceous earth) depth filters, and the like. Example of suitable filters include, without limitation, Cuno 50SA, Cuno 90SA, and Cuno VR06 filters (Cuno). Alternatively, the separation step can be performed by centrifugation rather than filtration. In a preferred embodiment, the finely divided silicon dioxide treated Fraction II+III paste suspension is filtered through a depth filter situated in a filter press.

6. Extraction of Factor H from Fraction I Precipitate and Fraction II+III Filter Cake After separation of a Fraction I precipitate from a Fraction I supernatant by centrifugation or filtration, Factor H can be extracted from the Fraction I precipitate by the addition of a Factor H extraction buffer, which can be used to re-suspend the Fraction I precipitate at a ratio of 1 part precipitate to at or about between 25 and 30 parts of extraction buffer. Other suitable re-suspension ratios may be used, for example at or about between 1:4 and 1:40, or at or about between 1:8 and 1:30, or at or about between 1:10 and 1:20, or at or about between 1:12 and 1:18, or at or about between 1:13 and 1:17, or at or about between 1:14 and 1:16. In certain embodiments, the ratio may be at or about 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, or higher.

In a related embodiment, Factor H can be extracted from a Fraction I precipitate by re-circulating a Factor H extraction buffer through a Fraction I precipitate cake or pellet. In one embodiment, a Factor H extraction buffer may be re-circulated through a Fraction I precipitate (e.g., a Fraction I filter cake) at a ratio of 1 part precipitate to at or about between 25 and 30 parts of extraction buffer. Other suitable re-suspension ratios may be used, for example at or about between 1:4 and 1:40, or at or about between 1:8 and 1:30, or at or about between 1:10 and 1:20, or at or about between 1:12 and 1:18, or at or about between 1:13 and 1:17, or at or about between 1:14 and 1:16. In certain embodiments, the ratio may be at or about 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, or higher. In a preferred embodiment, the Fraction I filter cake will remain in the filter press used to filter the precipitate from the supernatant during the extraction process.

After separation of a Fraction II+III filter cake from a Fraction II+III suspension by centrifugation or filtration, Factor H can be extracted from the Fraction II+III filter cake by the addition of a Factor H extraction buffer, which can be used to re-suspend the Fraction II+III filter cake at a ratio of 1 part precipitate to at or about between 25 and 30 parts of extraction buffer. Other suitable re-suspension ratios may be used, for example at or about between 1:4 and 1:40, or at or about between 1:8 and 1:30, or at or about between 1:10 and 1:20, or at or about between 1:12 and 1:18, or at or about between 1:13 and 1:17, or at or about between 1:14 and 1:16. In certain embodiments, the ratio may be at or about 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, or higher.

In a related embodiment, Factor H can be extracted from a Fraction II+III filter cake by re-circulating a Factor H extraction buffer through a Fraction II+III filter cake or pellet. In one embodiment, a Factor H extraction buffer may be re-circulated through a Fraction II+III filter cake at a ratio of 1 part precipitate to at or about between 25 and 30 parts of extraction buffer. Other suitable re-suspension ratios may be used, for example at or about between 1:4 and 1:40, or at or about between 1:8 and 1:30, or at or about between 1:10 and 1:20, or at or about between 1:12 and 1:18, or at or about between 1:13 and 1:17, or at or about between 1:14 and 1:16. In certain embodiments, the ratio may be at or about 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, or higher. In a preferred embodiment, the Fraction I filter cake will remain in the filter press used to filter the precipitate from the supernatant during the extraction process.

In a preferred embodiment, the step of extracting Factor H from a filter cake or precipitate comprises recirculation of a Factor H extraction buffer through a filter press containing the Factor H filter cake for at least 10 minutes. In other embodiments, the step of extracting Factor H from a filter cake or precipitate comprises recirculation of a Factor H extraction buffer through a filter press containing the Factor H filter cake for at or about between 10 and 60 minutes. In a preferred embodiment, the step of extracting Factor H from a filter cake or precipitate comprises recirculation of a Factor H extraction buffer through a filter press containing the Factor H filter cake for at or about between 20 and 40 minutes. In yet other embodiments, the step of extracting Factor H from a filter cake or precipitate comprises recirculation of a Factor H extraction buffer through a filter press containing the Factor H filter cake for at least 10 minutes or at least 15, 20, 25, 30, 35, 40, 45, 50, 55, 60, 65, 70, 75, 80, 85, or 90 minutes, or longer (e.g., at least about 2, 3, 4, 5, or 6 hours).

Generally, the extraction is performed at or about between 0° C. and 20° C., preferably at or about between 2° C. and 8° C. In certain embodiments, the extraction may be performed at or about 0° C., 1° C., 2° C., 3° C., 4° C., 5° C., 6° C., 7° C., 8° C., 9° C., or 10° C., 11° C., 12° C., 13° C., 14° C., 15° C., 16° C., 17° C., 18° C., 19° C., or 20° C. In a particular embodiment, the extraction is performed at or about between 2° C. and 10° C.

Any suitable buffer may be used for the extraction of Factor H from a Fraction I precipitate or Fraction II+III filter cake. Typical extractions buffers will contain at least a buffering agent and a salt. In certain embodiments, the extraction buffer will contain at or about between 10 and 250 mM of a buffering agent. In certain embodiments, the buffering agent will be present at a concentration of at or about 10 mM, or 20, 30, 40, 50, 60, 70, 80, 90, 100, 110, 120, 130, 140, 150, 160, 170, 180, 190, 200, 210, 220, 230, 240, 250 mM or more buffering agent. In certain embodiments, the extraction buffer will have an ionic strength of at or about between 5 and 100 mS/cm. In specific embodiments the extraction buffer will contain at or about between 50 and 500 mM salt. In certain embodiments, the salt will be present at a concentration of at or about 50 mM or at or about 75, 100, 125, 150, 175, 200, 225, 250, 300, 350, 400, 450, 500 mM or more salt.

Factor H extraction buffers will generally have a pH of at or about between 6.0 and 9.0. In certain embodiments, a Factor H extraction buffer will have a pH of at or about 6.0, or at or about 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, or 9.0. In a preferred embodiment, the Factor H buffer will have a pH at or about between 7.0 and 8.0. In a specific embodiment, the extraction buffer will have a pH of at or about 7.0. In another specific embodiment, the extraction buffer will have a pH of at or about 7.5. In another specific embodiment, the extraction buffer will have a pH of at or about 8.0. Non-limiting examples of buffering agents that may be used for the formulation of a Factor H extraction buffer include potassium phosphate, sodium phosphate, sodium acetate, sodium citrate, ammonium acetate, cacodylic acid, imidazole, boric acid, bicine, ACES, BES, BIS-Tris, BIS-Tris-propane, CAPS, CHES, glycine amide, glycylglycine, MES, MOPS, PIPES, HEPES, TAPS, TES, tricine, triethanolamine, and Tris.

In one embodiment, the Factor H extraction buffer will include or consist of 25 mM Tris; 5 mM EDTA; 200 mM NaCl; pH 8.0. In another embodiment, the Factor H extraction buffer will include or consist of 100 mM sodium phosphate; 150 mM sodium chloride; pH 7.5.

7. Third Precipitation Step—Removal of Impurities

In one embodiment, the method further comprises precipitating impurities from an enriched Factor H composition to form a precipitate (herein referred to as "Precipitate 3") and a supernatant (herein referred to as "Supernatant 3"). In certain embodiments, this step comprises precipitating at least one impurity, for example a lipid or protein, from the composition and then separating the precipitate from the supernatant containing Factor H. Precipitants suitable for precipitating impurities from a plasma-derived fraction are well known in the art and include, without limitation, alcohol (e.g., ethanol, methanol, etc.), water soluble polymers (e.g., PEG, dextrans, etc.), salts (e.g., ammonium phosphate, ammonium sulfate, sodium citrate, etc.), short chain fatty acids (e.g., hexanoic acid, heptanoic acid, caprylic acid, nanoic acid, decanoic acid, etc.), and the like. In certain embodiments, precipitation may be facilitated by matching the pH of the solution to the isoelectric point of a component of interest, i.e., isoelectric point precipitation.

In a preferred embodiment, the method comprises the step of precipitating at least one impurity from an enriched Factor H composition with at or about between 10% and 20% ethanol at a pH at or about between 7.0 and 9.0. In a preferred embodiment, the method comprises the step of precipitating at least one impurity from an enriched Factor H composition with at or about between 12% and 18% ethanol at a pH at or about between 7.3 and 8.7. In a more preferred embodiment, the method comprises the step of precipitating at least one impurity from an enriched Factor H composition with at or about between 14% and 16% ethanol at a pH at or about between 7.5 and 8.5. In a more preferred embodiment, the method comprises the step of precipitating at least one impurity from an enriched Factor H composition with at or about between 14% and 16% ethanol at a pH at or about between 7.8 and 8.2. In a most preferred embodiment, the method comprises the step of precipitating at least one impurity from an enriched Factor H composition with at or about 15% ethanol and at or about a pH of 8.0.

The concentration of the precipitant, e.g., ethanol, may be adjusted to maximize the precipitation of one or more impurities and/or minimize the precipitation of Factor H. In certain embodiments, the precipitation may be performed by the addition of at or about 10%, 11%, 12%, 13%, 14%, 15%, 16%, 17%, 18%, 19% or 20% ethanol. In a preferred embodiment, the precipitation is performed by the addition of at or about between 12% and 18% ethanol. In a more preferred embodiment, the precipitation is performed with at or about between 13% and 17% ethanol. In a more preferred embodiment, the precipitation is performed with at or about between 14% and 16% ethanol. In a most preferred embodiment, the precipitation is performed with at or about 15% ethanol.

The pH of the solution may be adjusted to maximize the precipitation of one or more impurities and/or to minimize the precipitation of Factor H. In certain embodiments, the pH of the solution is adjusted to at or about 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, or 9.0. In a preferred embodiment, the pH of the solution is adjusted to at or about between 7.2 and 8.8. In another preferred embodiment, the pH of the solution is adjusted to at or about between 7.3 and 8.7. In another preferred embodiment, the pH of the solution is adjusted to at or about between 7.4 and 8.6. In a more preferred embodiment, the pH of the solution is adjusted to at or about between 7.5 and 8.5. In a more preferred embodiment, the pH of the solution is adjusted to at or about between 7.6 and 8.4. In a more preferred embodiment, the pH of the solution is adjusted to at or about between 7.7 and 8.3. In a more preferred embodiment, the pH of the solution is adjusted to at or about between 7.8 and 8.2. In a more preferred embodiment, the pH of the solution is adjusted to at or about between 7.9 and 8.1. In a most preferred embodiment, the pH of the solution is adjusted to at or about 8.0.

8. Fourth Precipitation Step—Factor H Precipitation

In one embodiment, the enriched Factor H composition may be further purified subsequent to extraction from a Fraction I precipitate, Fraction II+III suspension, or Fraction II+III filter cake by precipitating Factor H out of the enriched composition to form a precipitate (herein referred to as "Precipitate 4") and a supernatant (herein referred to as "Supernatant 4"). In certain embodiments, an enriched Factor H composition may be subjected to a third precipitation step, as described above, to remove at least one impurity from the composition, as described above, and then to a fourth precipitation step to precipitate and recover Factor H.

In a preferred embodiment, precipitating Factor H from an enriched composition comprises the addition of between about 20% and about 30% ethanol at a pH between about 5.0 and about 7.0. In a preferred embodiment, the method comprises the step of precipitating Factor H with between about 22% to about 28% ethanol at a pH between about 5.5 and about 6.5. In a more preferred embodiment, the method comprises the step of precipitating Factor H with between about 24% to about 26% ethanol at a pH between about 5.8 and about 6.2. In a most preferred embodiment, the method comprises the step of precipitating Factor H with at or about 25% ethanol and at or about a pH of 6.0.

The concentration of the precipitant, e.g., ethanol, may be adjusted to maximize the precipitation Factor H and/or minimize the precipitation of one or more impurities. In certain embodiments, the precipitation may be performed by the addition of at or about 20%, 21%, 22%, 23%, 24%, 25%, 26%, 27%, 28%, 29% or 30% ethanol. In a preferred embodiment, the precipitation is performed by the addition at or about between 22% and 28% ethanol. In a more preferred embodiment, the precipitation is performed with at or about between 23% and 27% ethanol. With a more preferred embodiment, the precipitation is performed with at or about between 24% and 26% ethanol. In a most preferred embodiment, the precipitation is performed with at or about 25% ethanol.

The pH of the solution may be adjusted to maximize the precipitation Factor H and/or minimize the precipitation of one or more impurities. In certain embodiments, the pH of the solution is adjusted to at or about 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, or 7.0. In a preferred embodiment, the pH of the solution is adjusted to at or about between 5.2 and 6.8. In another preferred embodiment, the pH of the solution is adjusted to at or about between 5.3 and 6.7. In another preferred embodiment, the pH of the solution is adjusted to at or about between 5.4 and 6.6. In a more preferred embodiment, the pH of the solution is adjusted to at or about between 5.5 and 6.5. In a more preferred embodiment, the pH of the solution is adjusted to at or about between 5.6 and 6.4. In a more preferred embodiment, the pH of the solution is adjusted to at or about between 5.7 and 6.3. In a more preferred embodiment, the pH of the solution is adjusted to at or about between 5.8 and 6.2. In a more preferred embodiment, the pH of the solution is adjusted to at or about between 5.9 and 6.1. In a most preferred embodiment, the pH of the solution is adjusted to at or about 6.0.

9. Chromatographic Methods

In certain embodiments, the method for preparing an enriched Factor H composition further comprises at least one, preferably two or more, chromatographic steps to further enrich the purity of the composition. Generally, any suitable chromatographic method may be employed to further enrich the Factor H composition extracted from a Fraction I precipitate or Fraction II+III filter cake.

In certain embodiments, the chromatographic step may comprise anion exchange chromatography (AEC), cation exchange chromatography (CEC), heparin affinity chromatography, hydrophobic exchange chromatography (HIC), hydroxyapatite chromatography (HAP), immuno-affinity chromatography, size exclusion chromatography (i.e., gel filtration), or other suitable chromatographic step. Chromatographic steps may be performed in either batch or column mode.

In a preferred embodiment, the method comprises the steps of: binding Factor H to an anion exchange resin; eluting Factor H from the anion exchange resin with an elution buffer, thereby forming a first eluate containing Factor H. In a more preferred embodiment, the method further comprises the steps of binding Factor H from the anion exchange eluate to a heparin affinity resin; and eluting the Factor H from the heparin affinity resin with an elution buffer, thereby forming a second eluate containing Factor H. In certain embodiments, the chromatographic methods may further comprise wash steps to remove loosely bound impurities from the chromatographic resin prior to the elution of Factor H. In certain embodiments, Factor H may be eluted from a chromatography resin by gradient elution, e.g., with a salt gradient, or by step elution, e.g., with buffers having increasing ionic strength.

Generally, the conductivity of the Factor H solution is adjusted to an appropriate ionic strength prior to binding Factor H onto a chromatographic resin. The ionic strength should be low enough to promote the interaction between Factor H and the resin, yet high enough to maintain the stability of the protein in solution. The requirements for the ionic strength of the solution will vary dependent upon factors such as the identity of the resin used (e.g., strong vs. weak anion exchange resin) and the starting purity of the solution. Various methods may be employed for reducing the ionic strength of a Factor H composition, including without limitation, dilution of the composition with a solution having a low ionic strength, precipitating Factor H from the starting composition and re-suspending in a buffer having lower ionic strength, ultrafiltration/diafiltration, desalting and/or buffer exchange chromatography, dialysis, and the like.

Any suitable anion exchange resin may be used in the methods provided herein. Non-limiting examples of anion exchange resins suitable for use include, diethylaminoethyl (DEAE), quaternary aminoethyl (QAE), and quaternary ammonium (Q) resins. In a preferred embodiment, the anion exchange resin used is DEAE Sepharose™ (diethylaminoethyl-sepharose). In certain embodiments, the Factor H composition recovered from a Fraction I precipitate or a filter cake formed after the filtration or centrifugation of a Fraction II+III paste suspension in the presence of finely divided silicon dioxide and/or filter aid, as described above.

In a preferred embodiment, Factor H is bound to a DEAE Sepharose™ resin in the presence of a low ionic strength loading buffer. Typically, the column will be equilibrated with the same loading buffer or a compatible buffer with an ionic strength similar to the loading buffer. In certain embodiments, the loading and/or equilibration buffer will have an ionic strength of less than at or about 12 mS/cm. In a preferred embodiment, the loading and/or equilibration buffer will have an ionic strength of less than at or about 10 mS/cm. In a most preferred embodiment, the loading and/or equilibration buffer will have an ionic strength of at or about 9 mS/cm. In a preferred embodiment, the loading and/or equilibration buffer will have a salt concentration of less than at or about 100 mM NaCl, or ionic strength corresponding to less than that of a 100 mM NaCl solution. In a more preferred embodiment, the loading and/or equilibration buffer will have a salt concentration, or corresponding ionic strength, of less than at or about 75 mM NaCl. In a more preferred embodiment, the salt concentration, or corresponding ionic strength, will be at or about between 30 and 70 mM NaCl. In a most preferred embodiment, the salt concentration, or corresponding ionic strength, will be at or about 50 mM NaCl.

Optionally, after binding Factor H, the anion exchange resin may be washed with one or more buffers having ionic strengths intermediate of the loading buffer and the elution buffer. In certain embodiments, a wash buffer may have an ionic strength at or about between 9 mS/cm and 12.5 mS/cm. In a preferred embodiment, the wash buffer may have an ionic strength at or about between 5 mS/cm and 10 mS/cm. In certain embodiments, the wash buffer will have a salt concentration, or ionic strength corresponding to, at or about between 30 and 100 mM NaCl. In a preferred embodiment, the wash buffer will have a salt concentration, or ionic strength corresponding to, at or about between 40 and about 70 mM NaCl. In certain embodiments, the wash buffer will have a salt concentration, or ionic strength corresponding to, at or about 30, 35, 40, 45, 50, 55, 60, 65, 70, 75, 80, 85, 90, 95, or 100 mM NaCl.

In certain embodiments, Factor H is eluted from the anion exchange resin (e.g., DEAE Sepharose™) with an elution buffer having suitable ionic strength to disrupt the interaction between the resin and Factor H. In some embodiments, the elution buffer will not have a suitable ionic strength to disrupt the interaction between the resin and a contaminant that binds the resin with higher affinity than does Factor H. In certain embodiments, the elution buffer will have an ionic strength of at least at or about 12 mS/cm. In a preferred embodiment, the elution buffer will have an ionic strength of at or about 13 mS/cm. In another preferred embodiment, the elution buffer will have an ionic strength of at or about 14 mS/cm. In certain embodiments, the elution buffer will have a salt concentration, or ionic strength corresponding to, at least at or about 100 mM NaCl, preferably at least at or about 120 mM. In certain embodiments, the elution buffer will have a salt concentration, or ionic strength corresponding to, at least at or about 90 mM NaCl or at least at or about 95, 100, 105, 110, 115, 120, 125, 130, 140, 150 mM NaCl, or more.

Any suitable heparin affinity resin may be used in the methods provided herein, for example, resins conjugated to a heparin ligand, derivative or mimetic of a heparin ligand, or heparin-like ligand (e.g., a sulfated glycosaminoglycan). In a preferred embodiment, the heparin affinity resin used is Heparin Sepharose™.

In one embodiment, Factor H is further purified by heparin affinity chromatography. In a preferred embodiment, Factor H from the eluate of an anion exchange chromatography step is further purified by heparin affinity chromatography, e.g., a Heparin Sepharose™ resin. In one embodiment, the ionic strength of the Factor H eluate is reduced by a suitable method, e.g., dilution, buffer exchange, dialysis, etc., and Factor H is bound to a heparin affinity resin. In certain embodiments, the ionic strength of the anion exchange eluate is reduced to less than at or about 12 mS/cm. In a preferred embodiment, the ionic strength is reduced to less than at or about 10 mS/cm. In a more preferred embodiment, the ionic strength is reduced to less than at or about 8 mS/cm. In certain embodiments, the ionic strength may be reduced to less than at or about 4 mS/cm, or less than at or about 5, 6, 7, 8, 9, 10, 11, or 12 mS/cm. In certain embodiments, the salt concentration of the anion exchange eluate, or ionic strength corresponding to, is reduced less than at or about 100 mM NaCl. In a preferred embodiment, the salt concentration, or ionic strength corresponding to, is reduced less than at or about 75 mM NaCl. In a more preferred embodiment, the salt concentration, or ionic strength corresponding to, is reduced less than at or about 50 mM NaCl. In certain embodiments, the salt concentration, or ionic strength corresponding to, is reduced less than at or about 20 mM NaCl, or less than at or about 25, 30, 40, 50, 60, 70, 80, 90, or 100 mM NaCl.

Optionally, after binding Factor H, the heparin affinity resin may be washed with one or more buffers having ionic strengths intermediate of the loading buffer and the elution buffer. In certain embodiments, a wash buffer may have an ionic strength at or about between 3 mS/cm and 12.5 mS/cm. In a preferred embodiment, the wash buffer may have an ionic strength at or about between 5 mS/cm and 10 mS/cm. In certain embodiments, the wash buffer will have a salt concentration, or ionic strength corresponding to, at or about between 30 and 100 mM NaCl. In a preferred embodiment, the wash buffer will have a salt concentration, or ionic strength corresponding to, at or about between 30 and 80 mM NaCl. In certain embodiments, the wash buffer will have a salt concentration, or ionic strength corresponding to, at or about 30, 35, 40, 45, 50, 55, 60, 65, 70, 75, 80, 85, 90, 95, or 100 mM NaCl.

In certain embodiments, Factor H is eluted from the heparin affinity resin (e.g., DEAE Sepharose™) with an elution buffer having suitable ionic strength to disrupt the interaction between the resin and Factor H. In some embodiments, the elution buffer will not have a suitable ionic strength to disrupt the interaction between the resin and a contaminant that binds the resin with higher affinity than does Factor H. In certain embodiments, the elution buffer will have an ionic strength of at least at or about 12 mS/cm. In certain embodiments, the elution buffer will have a salt concentration, or ionic strength corresponding to, at least at or about 100 mM NaCl. In another embodiment, the elution buffer will have a salt concentration, or ionic strength corresponding to, at least at or about 150 mM NaCl. In yet another embodiment, the elution buffer will have a salt concentration, or ionic strength corresponding to, at least at or about 200 mM NaCl. In certain embodiments, the elution buffer will have a salt concentration, or ionic strength corresponding to, at least at or about 90 mM NaCl or at least at or about 95, 100, 105, 110, 115, 120, 125, 130, 140, 150, 160, 170, 180, 190, 200, 210, 220 mM NaCl, or more.

An alternative purification process consists of taking an enriched Factor H composition (e.g., extracted from a Fraction I precipitate or Fraction II+III filter cake) at a pH at or about between 7.0 and 9.0, preferably at or about 8.0, and adjusting the ionic strength such that Factor H will not bind to an anion exchange resin, for example to an ionic strength equal to at or about between 120 and 150 mM NaCl, and then contacting the solution with an anion exchange resin (e.g., a DEAE sepharose column) to bind unwanted proteins in the extract. The Factor H will not bind to the column and can be collected as a flow through fraction for further processing. The Factor H pool is then adjusted to an ionic strength equivalent to no more than at or about 65 mM NaCl, preferably no more than at or about 50 mM NaCl and bound to a heparin affinity resin (e.g., a Heparin Sepharose™ column). A buffer having an ionic strength suitable to elute the Factor H from the resin is then added to recover the Factor H. In a preferred embodiment, the elution buffer will have an ionic strength equivalent to a sodium chloride concentration of at or about between 90 and 250 mM NaCl, preferably at or about between 100 and 200 mM NaCl. The ionic strength of the Factor H eluate can then be lowered to a level suitable for binding Factor H to an anion exchange resin, for example to an ionic strength equivalent to no more than at or about 65 mM NaCl, preferably no more than about 50 mM NaCl. Factor H is then bound to the anion exchange resin (e.g., a DEAE Sepharose™ column) to remove impurities from the pool that do not bind the resin under these conditions. The Factor H is eluted with a buffer having a suitable ionic strength, for example an ionic strength equivalent to at least at or about 100 mM NaCl, preferably at least at or about 120 mM NaCl.

Any suitable cation exchange resin may be used in the methods provided herein. Non-limiting examples of cation exchange resins suitable for use include, carboxymethyl (CM), sulfopropyl (SP), methyl sulfonate (S) resins.

Any suitable hydroxyapatite or other calcium-based resin may be used in the methods provided herein. Non-limiting examples of suitable resins include hydroxyapatite resins, fluorapatite resins, fluorhydroxyapatite resins, and the like.

Any suitable hydrophobic interaction chromatography resin may be used in the methods provided herein. Non-limiting examples of suitable resins include phenyl-resins, methyl-resins, butyl-resins, octyl-resins, and the like.

In certain embodiments, Factor H may be further enriched by immuno-affinity chromatography, for example with resins conjugated to an antibody, aptamer, or other binding molecule highly specific for Factor H.

In certain embodiments, individual or all chromatographic steps will rely on a common buffer system, in which only the salt concentration varies between the equilibration, wash, and elution buffers. Any suitable buffer may be used, e.g., a Tris buffer, a phosphate buffer, a citrate buffer, etc. The pH of the loading buffer will range at or about between 6.0 and 9.0. In a preferred embodiment, the pH of the buffer system is at or about between 7.0 and 9.0. In a more preferred embodiment, the pH of the buffer system is at or about between 7.5 and 8.5. In a most preferred embodiment, the pH of the buffer system will be at or about 8.0.

10. Virus Inactivation and Removal

In certain embodiments, the methods provided herein for the preparation of an enriched Factor H composition will further include at least one, preferably at least two, most preferably at least three, viral inactivation or removal steps. Non-limiting examples of viral inactivation or removal steps that may be employed with the methods provided herein include, solvent detergent treatment (Horowitz et al., *Blood Coagul Fibrinolysis* 1994 (5 Suppl 3):S21-S28 and Kreil et al., *Transfusion* 2003 (43):1023-1028, the disclosures of which are expressly incorporated by reference herein in their entireties for all purposes), nanofiltration (Hamamoto et al., *Vox Sang* 1989 (56)230-236 and Yuasa et al., *J Gen Virol.* 1991 (72 (pt 8)):2021-2024, the disclosures of which are expressly incorporated by reference herein in their entireties for all purposes), and low pH incubation at high temperatures (Kempf et al., *Transfusion* 1991 (31)423-427 and Louie et al., *Biologicals* 1994 (22):13-19, the disclosure of which is expressly incorporated by reference herein in its entirety for all purposes).

Viral inactivation or removal steps may be performed on any intermediate Factor H fractions generated during the manufacturing process. For example, in one embodiment, a viral inactivation or removal step may be performed on a Fraction I supernatant, Fraction II+III suspension, Fraction II+III filter cake extract, Supernatant 3, Precipitate 4 suspension, anion exchange eluate, heparin affinity eluate, and the like.

In one embodiment, a viral inactivation or removal step is performed on the Fraction II+III filter cake extract. In a preferred embodiment the Fraction II+III filter cake extract is subjected to solvent and detergent (S/D) treatment.

In a second embodiment, a viral inactivation or removal step is performed on the Precipitation 3 supernatant (Supernatant 3). In a preferred embodiment the Precipitation 3 supernatant is subjected to solvent and detergent (S/D) treatment.

In a third embodiment, a viral inactivation or removal step is performed on the Precipitate 4 suspension. In a preferred embodiment the Precipitate 4 suspension is subjected to solvent and detergent (S/D) treatment.

In a fourth embodiment, a viral inactivation or removal step is performed on the anion exchange eluate. In a preferred embodiment the anion exchange eluate is subjected to solvent and detergent (S/D) treatment. In another preferred embodiment, the anion exchange eluate is subjected to nanofiltration.

In a fifth embodiment, a viral inactivation or removal step is performed on the heparin affinity eluate. In a preferred embodiment the heparin affinity eluate is subjected to solvent and detergent (S/D) treatment. In another preferred embodiment, the heparin affinity eluate is subjected to nanofiltration.

In a sixth embodiment, a viral inactivation or removal step is performed on an enriched Factor H bulk solution. In a preferred embodiment, the enriched Factor H bulk solution is subjected to nanofiltration. In another preferred embodiment, the enriched Factor H bulk solution is subjected to incubation at low pH and/or high temperatures.

In a seventh embodiment, a lyophilized Factor H composition is heat treated to inactivate viruses.

In one embodiment, a manufacturing process for plasma-derived Factor H is provided that contains two viral inactivation or removal steps. In a preferred embodiment, the process contains both solvent and detergent treatment and nanofiltration steps for the inactivation and removal of viral particles. In one preferred embodiment, the manufacturing process comprises subjecting the Precipitate 3 supernatant to S/D treatment and the heparin eluate to nanofiltration. In another preferred embodiment, the manufacturing process comprises subjecting the Precipitate 4 suspension or a clarified filtrate thereof to S/D treatment and the heparin eluate to nanofiltration. In another preferred embodiment, the manufacturing process further comprises a viral inactivation step comprising incubating a final bulk Factor H composition at low pH for an extended period of time.

a) Solvent and Detergent (S/D) Treatment

In order to inactivate various viral contaminants which may be present in plasma-derived products, one or more Factor H intermediate solutions may be subjected to a solvent detergent (S/D) treatment. Methods for the detergent treatment of plasma-derived fractions are well known in the art (for review see, Pelletier J P et al., *Best Pract Res Clin Haematol.* 2006; 19(1):205-42, the disclosure of which is expressly incorporated by reference herein in its entirety for all purposes). Generally, any standard S/D treatment may be used in conjunction with the methods provided herein. For example, an exemplary protocol for an S/D treatment is provided below.

In one embodiment, Triton X-100, Tween-20, and tri(n-butyl)phosphate (TNBP) are added to a Factor H intermediate solution at final concentrations of at or about 1.0%, 0.3%, and 0.3%, respectively. The mixture is then stirred at a temperature at or about between 18° C. and 25° C. for at least about an hour.

In one embodiment, the S/D reagents (e.g., Triton X-100, Tween-20, and TNBP) are added by spraying rather than by fluent addition. In other embodiments, the detergent reagents may be added as solids to the Factor H intermediate solution, which is being mixed to ensure rapid distribution of the S/D components. In certain embodiments, it is preferable to add solid reagents by sprinkling the solids over a delocalized surface area of the filtrate such that local overconcentration does not occur, such as in fluent addition. In another embodiment, the Factor H containing solution is pumped into a tank where the SD-reagents are already present either in concentrated or diluted form.

b) Nanofiltration and Ultra/Diafiltration

In order to further reduce the viral load of the Factor H composition provided herein, a Factor H fraction, for example the heparin affinity eluate, may be nanofiltered using a suitable nanofiltration device. In certain embodiments, the nanofiltration device will have a mean pore size of at or about between 15 nm and 200 nm. Examples of nanofilters suitable for this use include, without limitation, DVD, DV 50, DV 20 (Pall), Viresolve NFP, Viresolve NFR (Millipore), Planova 15N, 20N, 35N, and 75N (Planova). In a specific embodiment, the nanofilter may have a mean pore size of at or about between 15 and 72 nm, or at or about between 19 and 35 nm, or of at or about 15 nm, 19 nm, 35 nm, or 72 nm. In a preferred embodiment, the nanofilter will have a mean pore size of at or about 35 nm, such as an Asahi PLANOVA 35N filter or equivalent thereof.

Optionally, ultrafiltration/diafiltration may performed to further concentrate the nanofiltrate. In one embodiment, an open channel membrane is used with a specifically designed post-wash and formulation near the end the production process resulting in a Factor H composition of high concentration.

Subsequent to nanofiltration, the filtrate may be further concentrated by ultrafiltration and/or the buffer composition adjusted by diafiltration. In one embodiment, the nanofiltrate may be concentrated by ultrafiltration to a protein concentration of at or about between 0.5% and 10% (w/v). In certain embodiments, the ultrafiltration is carried out in a cassette with an open channel screen and the ultrafiltration membrane has a nominal molecular weight cut off (NMWCO) of less than at or about 150 kDa or less than at or about 140, 130, 120, 100, 90, 80, 70, 60, 50, 40, 30, or fewer kDa. In a preferred embodiment, the ultrafiltration membrane has a NMWCO of no more than 50 kDa.

Upon completion of the ultrafiltration step, buffer exchange may be performed by diafiltration against a solution suitable for intravenous, intramuscular, intraocular, subcutaneous, or other appropriate administration. In certain embodiments, the diafiltration solution may comprise a stabilizing and/or buffering agent, for example, salts, sugars, and/or a non-ionic detergent (e.g., Polysorbate 80).

Typically, the minimum exchange volume is at least at or about 3 times the original concentrate volume or at least at or about 4, 5, 6, 7, 8, 9, or more times the original concentrate volume. The Factor H solution may be concentrated to a final protein concentration of at or about between 0.5% and 25% (w/v), or at or about between 1% and 25% (w/v), or at or about between 2% and 20% (w/v), or at or about between 3% and 15% (w/v), or at or about between 5% and 10% (w/v), or at or about between 9% and 12%, or at or about between 3% and 7% (w/v), or at or about between 8% and 14% (w/v), or at or about between 4% and 6%, or to a final concentration of at or about 0.1%, 0.25%, 0.5%, 1%, 2%, 3%, 4%, 5%, or 6%, 7%, 8%, 9%, 10%, 11%, 12%, 13%, 14%, 15%, 16%, 17%, 18%, 19%, 20%, 21%, 22%, 23%, 24%, 25% or higher.

c) Incubation at Low pH

In certain embodiments, a Factor H containing solution may be treated to reduce or inactivate the viral load of the composition. In one embodiment, this is achieved by adjusting the pH of the of the composition to low pH, for example, less than at or about 6.0, and incubating for at least about a week prior to releasing the composition. In a preferred embodiment, the pH of the bulk solution is adjusted to less than at or about 5.5 prior to incubation. In a more preferred embodiment, the pH of the solution is lowered to less than at or about 5.0 prior to incubation. In certain embodiments, the pH of the solution is lowered to less than at or about 6.0 or less than at or about 5.9, 5.8, 5.7, 5.6, 5.5, 5.4, 5.3, 5.2, 5.1, 5.0, 4.9, 4.8, 4.7, 4.6, 4.5, 4.4, 4.3, 4.2, 4.1, 4.0, or lower prior to incubation.

In certain embodiments, the solution is then incubated for at least at or about one week, or at least at or about 2, 3, 4, or more weeks, or for at least at or about 1, 2, 3, or more months. In preferred embodiments, the composition is incubated at a temperature at or about above 20° C., or at or about above 25° C., or at or about above 30° C. In particular embodiments, the composition is incubated at a temperature of at or about 20° C., or at or about 21° C., 22° C., 23° C. 24° C., 25° C., 26° C., 27° C., 28° C., 29° C., 30° C., 31° C., 32° C., 33° C., 34° C., 35° C., 36° C., 37° C., 38° C., 39° C., 40° C., or higher.

d) Lyophilization and Heat Treatment

In yet other embodiments, the present invention provided lyophilized Factor H compositions. The viral activity of these lyophilized composition, which may have previously been subjected to other viral inactivation or removal steps such as S/D treatment or nanofiltration, may be further reduced by heat treatment of the lyophilized composition (i.e., Factor H lyo cake). Heat treatments for the inactivation of viral loads in blood factors are well known in the art (for example, see, Piszkiewicz et al., *Thromb Res.* 1987 Jul. 15; 47(2):235-41; Piszkiewicz et al., *Curr Stud Hematol Blood Transfus.* 1989; (56):44-54; Epstein and Fricke, *Arch Pathol Lab Med.* 1990 March; 114(3):335-40).

11. Formulation

Upon completion of the Factor H enrichment process, e.g., after a final diafiltration step, the protein concentration of the solution is adjusted to with a buffer, e.g., the diafiltration buffer, to a final concentration of at or about between 0.5% and 20% (w/v), or at or about between 1% and 25% (w/v), or at or about between 2% and 20% (w/v), or at or about between 3% and 15% (w/v), or at or about between 5% and 10% (w/v), or at or about between 9% and 12%, or at or about between 3% and 7% (w/v), or at or about between 8% and 14% (w/v), or at or about between 4% and 6%, or to a final concentration of at or about 0.1%, 0.25%, 0.5%, 1%, 2%, 3%, 4%, 5%, 6%, 7%, 8%, 9%, 10%, 11%, 12%, 13%, 14%, 15%, 16%, 17%, 18%, 19%, 20%, or higher.

In certain embodiments, the formulated bulk solution may be further sterilized by filtering through a membrane filter with an absolute pore size of no more than about 0.22 micron, for example about 0.1 or 0.2 micron. In certain embodiments, the solution may be aseptically dispensed into final containers for proper sealing, with samples taken for testing.

B. Alcohol Addition

Advantageously, it has been found that, for purposes of fractionating blood products (e.g., Factor H, IgG, Albumin) from plasma, addition of alcohol by a method that finely disperses or that rapidly disperses the alcohol at the point of addition results in reduced loss of blood product yields. Without being bound by theory, during fluent addition to a plasma fraction, transient local overconcentration of alcohol at the fluid ingress may lead to protein denaturation and irreversible loss and/or precipitation of a blood factor during steps in which the blood factor should remain in the supernatant. Furthermore, these effects may by amplified when large volumes of alcohol need to be added, such as in industrial scale purifications involving the fractionation of at least 100 L of pooled plasma.

In one embodiment, alcohol is added in one or more precipitation steps by a method that finely disperses the alcohol over a delocalized area. For example, alcohol can be added to a fractionation step by spraying onto the surface of the vessel or tank containing the plasma fraction. Accordingly, in one aspect of the methods provided herein, one or more precipitation steps are performed by the spray addition of alcohol. In certain embodiments, spray addition may be performed by using any pressurized device, such as a container (e.g., a spray bottle), that has a spray head or a nozzle and is operated manually or automatically to generate a fine mist from a liquid. In certain embodiments, spray addition is performed while the system is continuously stirred or otherwise mixed to ensure rapid and equal distribution of the liquid within the system.

In another embodiment, alcohol is added in one or more precipitation steps by a method that rapidly disperses the alcohol at the point of addition. For example, alcohol can be added from below the vessel or tank containing the plasma fraction, directly adjacent to a stirring apparatus (e.g., a propeller). In certain embodiments, fluent addition at a ingress directly adjacent to a stirring apparatus is performed while the system is continuously stirred or otherwise mixed to ensure rapid and equal distribution of the liquid within the system.

C. Adjustment of the pH

The protein precipitation profiles of plasma fractions is highly dependent upon the pH of the solution from which the plasma proteins are being precipitated. This fact has been exploited by scientists fractionating plasma proteins since the introduction of the Cohn and Oncley methods in 1946 and 1949, respectively. Traditionally, the pH of a plasma fraction is adjusted prior to alcohol addition to facilitate the highest recovery yields for the component(s) of interest. Advantageously, it has now been found that by adjusting the pH of the solution directly after addition of alcohol or concomitant with alcohol addition results in a more defined and reproducible precipitation. It was found that ethanol addition to plasma fractions results in fluctuations in the pH of the solution, generally by raising the pH of the solution. As such, by adjusting the pH of a plasma fraction to a predetermined pH before but not after alcohol addition, the precipitation reaction will occur at a non-optimal pH.

Likewise, precipitation of proteins from a plasma fraction will effect the electrostatic environment and will thus alter the pH of the solution. Accordingly, as a precipitation event is allowed to progress, the pH of the solution will begin to diverge from the predetermined pH value that allows for maximal recovery of the protein species of interest. This is especially true for precipitation events in which a large fraction of the protein is being precipitated, precipitation events in which a high alcohol content is used, and precipitation events that require a long incubation period.

Accordingly, in one aspect of the methods provided herein, the pH of a plasma fraction is adjusted directly after the addition of alcohol. In related embodiments, the pH may be adjusted before and after alcohol addition, or during and after alcohol addition, or before, during, and after alcohol addition. In a related embodiment, the pH of a solution is continuously adjusted during one or more alcohol precipitation events or incubations. In certain embodiments, the pH of a solution is continuously adjusted or maintained while the system is continuously stirred or otherwise mixed to ensure rapid and equal distribution of the pH modifying agent within the system.

Similar to the case of fluent alcohol addition, it has now been found that the fluent addition of large volumes of a pH modifying agent may cause transient local pH variations, resulting in unwanted protein denaturation or precipitation. Accordingly, in one embodiment of the methods provided herein, pH modifying agents may be introduced into one or more plasma fractionation steps by a method that finely disperses or that rapidly disperses the alcohol at the point of addition.

In one embodiment, a pH modifying agent is added in one or more steps by a method that finely disperses the pH modifying agent over a delocalized area. For example, the pH modifying agent can be added to a step by spraying onto the surface of the plasma fraction contained within a vessel or tank. In another embodiment of the methods provided herein, the pH of a plasma fraction or precipitation step may be adjusted by spray addition of a pH modifying agent. In certain embodiments, spray addition may be performed by using any pressurized device, such as a container (e.g., a spray bottle), that has a spray head or a nozzle and is operated manually or automatically to generate a fine mist from a liquid. In certain embodiments, spray addition is performed while the system is continuously stirred or otherwise mixed to ensure rapid and equal distribution of the liquid within the system.

In another embodiment, a pH modifying agent is added in one or more steps by a method that rapidly disperses the pH modifying agent at the point of addition. For example, a pH modifying agent can be added from below the vessel or tank containing the plasma fraction, directly adjacent to a stirring apparatus (e.g., a propeller). In certain embodiments, fluent addition at a ingress directly adjacent to a stirring apparatus is performed while the system is continuously stirred or otherwise mixed to ensure rapid and equal distribution of the liquid within the system.

In yet another embodiment, a pH modifying agent is added in one or more steps by sprinkling a solid pH modifying agent over a delocalized area on the surface of the plasma fraction. In certain embodiments, addition by this means is performed while the system is continuously stirred or otherwise mixed to ensure rapid and equal distribution of the pH modifying agent within the system.

IV. Factor H Compositions

Factor H compositions have been described for the treatment of certain complement related disorders. (See, for example, U.S. Patent Publication No. US 2009/0118163 and European Patent Application No. EP 0 222 611 A2, the disclosures of which are herein incorporated by reference in their entireties for all purposes.)

In one aspect, the present invention provides Factor H compositions prepared according to a method described herein. In one embodiment, Factor H is prepared from materials otherwise discarded during the manufacture of a commercial plasma-derived blood product, for example IgG or Albumin. In one embodiment, a Factor H composition is provided, wherein Factor H is extracted from a Fraction I precipitate and/or a Fraction II+III filter cake.

Factor H as described in this invention can be formulated into pharmaceutical preparations for therapeutic use. The purified protein may be dissolved in conventional physiologically compatible aqueous buffer solutions to which there may be added, optionally, pharmaceutical excipients to provide pharmaceutical preparations.

Such pharmaceutical carriers and excipients as well as suitable pharmaceutical formulations are well known in the art (see for example "Pharmaceutical Formulation Development of Peptides and Proteins", Frokjaer et al., Taylor & Francis (2000) or "Handbook of Pharmaceutical Excipients", $3^{rd}$ edition, Kibbe et al., Pharmaceutical Press (2000)). In particular, the pharmaceutical composition comprising the polypeptide variant of the invention may be formulated in lyophilized or stable soluble form. The polypeptide variant may be lyophilized by a variety of procedures known in the art. Lyophilized formulations are reconstituted prior to use by the addition of one or more pharmaceutically acceptable diluents such as sterile water for injection or sterile physiological saline solution.

Formulations of the composition are delivered to the individual by any pharmaceutically suitable means of administration. Various delivery systems are known and can be used to administer the composition by any convenient route. Preferentially the compositions of the invention are administered systemically. For systemic use, Factor H of the invention is formulated for parenteral (e.g. intravenous, subcutaneous, intramuscular, intraperitoneal, intracerebral, intrapulmonar, intranasal, intravitreal, or transdermal) or enteral (e.g., oral, vaginal or rectal) delivery according to conventional methods. The formulations can be administered continuously by infusion or by bolus injection. Some formulations encompass slow release systems. Preferred routes of administration will depend upon the indication being treated, managed, or prevented. For example, in one embodiment, wherein Factor H is administered for the treatment of AMD, the preferred route of administration will be intravitreal. In a second embodiment, wherein Factor H is being administered for the treatment or management of aHUS, the preferred route of administration will be intravenous. A skilled physician will readily be able to determine the preferred route of administration for the particular affliction being treated, managed, or prevented.

In another aspect, the present invention provides a substantially purified Factor H preparation prepared according to a method provided herein. In one embodiment, the method comprises (a) performing Cohn fractionation to obtain a Fraction II+III precipitate and preparing a suspension of the combined precipitates, (b) filtering the re-suspended Fraction II+III precipitate to obtain a filter cake discard left behind after filtration of the Fraction II+III suspension; (c) extracting the filter cake according to a method comprising the steps of: (i) dissolving the filter cake in a suitable buffer of appropriate ionic strength for a time sufficient to dissolve the protein caked on said filter cake; (ii) diluting said dissolved protein with additional buffer, (iii) removing debris from the diluted protein, (iv) purifying Factor H protein from said diluted protein preparation by subjecting the diluted protein to ultrafiltration on a 0.45 µm filter to produce a filtrate containing Factor H; (v) subjecting the filtrate containing Factor H to anion exchange chromatography using a NaCl gradient (50-500 mM) in the running buffer to produce a pooled crude Factor H fraction; and (vi) purifying Factor H from said crude Factor H preparation by Heparin Sepharose™ chromatography using a gradient of NaCl (50-500 mM).

In one aspect of the substantially purified Factor H preparation, the Factor H preparation is an active Factor H preparation that is composed of a mixture of Tyr-402 and His-402 isoforms in the range 50%±20% His-402: 50%±20% Tyr-402.

A. Aqueous Compositions

In one aspect, the present invention provides aqueous compositions of plasma-derived Factor H prepared from materials otherwise discarded during the preparation of other commercially important blood products by plasma fractionation. Aqueous Factor H compositions prepared by the methods provided herein will have high Factor H content and purity. For example, Factor compositions provided herein may have a protein concentration of at least at or about 3% (w/v) and a Factor H content of greater than at or about 90% purity.

In one embodiment, aqueous compositions of Factor H are provided that are prepared from a Fraction II+III filter cake. In one embodiment, an aqueous composition of Factor H is provided that is prepared by a method comprising the steps of: (i) extracting Factor H from a Fraction II+III filter cake, (ii) optionally performing a first precipitation step to precipitate at least one impurity from the Factor H composition, (iii) optionally performing a second precipitation step to precipitate Factor H from the composition, (iv) optionally performing at least one ion exchange chromatography step, (v) optionally performing at least one heparin affinity chromatography step; and (vi) optionally performing at least one viral inactivation or removal step, thereby preparing an aqueous Factor H composition.

In a preferred embodiment, a Factor H composition is provided that is prepared by a method comprising the steps of: (a) precipitating proteins from a cryo-poor plasma fraction, in a first precipitation step, with between about 6% and about 10% alcohol at a pH of between about 7.0 and about 7.5 to obtain a first precipitate and a first supernatant; (b) precipitating Factor H from the first supernatant, in a second precipitation step, with between about 20% and about 25% alcohol at a pH of between about 6.7 and about 7.3 to form a second precipitate; (c) re-suspending the second precipitate to form a suspension; (d) mixing finely divided silicon dioxide (SiO2) with the suspension from step (c); (e) filtering the suspension with a filter press, thereby forming a filter cake and a supernatant; and (f) extracting Factor H from the filter cake with a Factor H extraction buffer, thereby preparing an aqueous composition of Factor H.

In certain embodiments, Factor H is extracted from the filter cake by re-circulation of an extraction buffer through a filter press containing the filter cake. Generally, the extraction buffer will be re-circulated through the filter cake for at or about between 5 minutes and 2 hours. In a preferred embodiment, the extraction buffer will be re-circulated through the filter cake for at or about between 10 and 60 minutes. In another preferred embodiment, the extraction buffer will be re-circulated through the filter cake for at or about between 20 and 40 minutes. In another preferred embodiment, the extraction buffer will be re-circulated through the filter cake for at or about 30 minutes. In other embodiments, the extraction buffer will be re-circulated through the filter cake for at least at or about 5, 10, 15, 20, 25, 30, 35, 40, 45, 50, 55, 60, 65, 70, 75, 80, 85, 90, 95, 100, 105, 110, 115, 120, or more minutes.

In another embodiment, aqueous compositions of Factor H are provided that are prepared from a Fraction I precipitate. In one embodiment, an aqueous composition of Factor H is provided that is prepared by a method comprising the steps of: (i) extracting Factor H from a Fraction I precipitate, (ii) optionally performing a first precipitation step to precipitate at least one impurity from the Factor H composition, (iii) optionally performing a second precipitation step to precipitate Factor H from the composition, (iv) optionally performing at least one ion exchange chromatography step, (v) optionally performing at least one heparin affinity chromatography step; and (vi) performing at least one viral inactivation or removal step, thereby preparing an aqueous Factor H composition.

In a preferred embodiment, aqueous compositions of Factor H are provided that are prepared from a Fraction I precipitate. In a particularly preferred embodiment, a Factor H composition is provided that is prepared by a method comprising the steps of: (a) precipitating proteins from a cryo-poor plasma fraction, in a first precipitation step, with between about 6% and about 10% alcohol at a pH of between about 7.0 and about 7.5 to obtain a first precipitate and a first supernatant; and (b) extracting Factor H from the precipitate with a Factor H extraction buffer, thereby preparing an aqueous composition of Factor H.

In certain embodiments, Factor H is extracted from the Fraction I precipitate by re-circulation of an extraction buffer through a filter press containing the Fraction I precipitate. Generally, the extraction buffer will be re-circulated through the precipitate for at or about between 5 minutes and 2 hours. In a preferred embodiment, the extraction buffer will be re-circulated through the precipitate for at or about between 10 and 60 minutes. In another preferred embodiment, the extraction buffer will be re-circulated through the precipitate for at or about between 20 and 40 minutes. In another preferred embodiment, the extraction buffer will be re-circulated through the precipitate for at or about 30 minutes. In other embodiments, the extraction buffer will be re-circulated through the precipitate for at least at or about 5, 10, 15, 20, 25, 30, 35, 40, 45, 50, 55, 60, 65, 70, 75, 80, 85, 90, 95, 100, 105, 110, 115, 120, or more minutes.

In certain embodiments, Factor H is extracted from the Fraction I precipitate or Fraction II+III filter cake by the addition of a Factor H extraction buffer, which can be used to re-suspend the Fraction I precipitate at a ratio of 1 part precipitate to at or about between 25 and 30 parts of extraction buffer. In other embodiments, the re-suspension ratio is at or about between 1:4 and 1:40, or at or about between 1:8 and 1:30, or at or about between 1:10 and 1:20, or at or about between 1:20 and 1:30, or at or about between 1:12 and 1:18, or at or about between 1:13 and 1:17, or at or about between 1:14 and 1:16. In one embodiment, the re-suspension ratio is at or about 1:25. In another embodiment, the re-suspension ratio is at or about 1:30. In certain embodiments, the ratio may be at or about 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, or higher. In a preferred embodiment, Factor H is extracted by re-circulation of the extraction buffer through a filter or filter press containing the Fraction I precipitate or Fraction II+III filter cake.

In certain embodiments, an aqueous composition of Factor H is provided, wherein the Factor H composition is prepared using a purification method described herein, wherein the method comprises the addition of one or more solutions, that would otherwise be introduced into a plasma fraction by fluent addition, by a method that finely disperses or that rapidly disperses the solution at the point of addition. For example, in certain embodiments the method will comprise the introduction of alcohol (e.g., ethanol) into a plasma fraction by spraying. In other embodiments, solutions that may be added to a plasma fraction by spraying include, without limitation, a pH modifying solution, a solvent solution, a detergent solution, a dilution buffer, a conductivity modifying solution, and the like. In one embodiment, one or more alcohol precipitation steps is performed by the addition of alcohol to a plasma fraction by spraying. In a second preferred embodiment, one or more pH adjustment steps is performed by the addition of a pH modifying solution to a plasma fraction by spraying.

In certain embodiments, an aqueous Factor H composition is provided that is prepared by a purification method described herein, wherein the method comprises adjusting the pH of a plasma fraction being precipitated after and/or concomitant with the addition of the precipitating agent (e.g., alcohol or polyethylene glycol). In some embodiments, a process improvement is provided in which the pH of a plasma fraction being actively precipitated is maintained throughout the entire precipitation incubation or hold step by continuous monitoring and adjustment of the pH. In preferred embodiments the adjustment of the pH is performed by the spray addition of a pH modifying solution.

In one embodiment, the present invention provides aqueous Factor H compositions comprising a protein concentration of at or about between 10 g/L and 250 g/L. In certain embodiments, the protein concentration of the Factor H composition is at or about between 50 g/L and 200 g/L, or at or about between 70 g/L and 150 g/L, or at or about between 90 g/L and 120 g/L, or at or about between 30 g/L and 70 g/L, or at or about between 40 g/L and 60 g/L or any suitable concentration within these ranges, for example at or about 10 g/L, or at or about 15 g/L, 20 g/L, 25 g/L, 30 g/L, 35 g/L, 40 g/L, 45 g/L, 50 g/L, 55 g/L, 60 g/L, 65 g/L, 70 g/L, 75 g/L, 80 g/L, 85 g/L, 90 g/L, 95 g/L, 100 g/L, 105 g/L, 110 g/L, 115 g/L, 120 g/L, 125 g/L, 130 g/L, 135 g/L, 140 g/L, 145 g/L, 150 g/L, 155 g/L, 160 g/L, 165 g/L, 170 g/L, 175 g/L, 180 g/L, 185 g/L, 190 g/L, 195 g/L, 200 g/L, 205 g/L, 210 g/L, 215 g/L, 220 g/L, 225 g/L, 230 g/L, 235 g/L, 240 g/L, 245 g/L, 250 g/L, or higher. In a preferred embodiment, Factor H compositions having high protein concentrations will also high levels of purity. In one embodiment, at least 90% of the protein in the composition will be Factor H. In a preferred embodiment, at least 95% of the protein in the composition will be Factor H.

The methods provided herein allow for the preparation of Factor H compositions having very high levels of purity. In one embodiment, at least 90% of the total protein in a composition provided herein will be Factor H. In a preferred embodiment, at least 95% of the total protein in a composition provided herein will be Factor H. In other embodiments, at least 90%, 91%, 92%, 93%, 94%, 95%, 96%, 97%, 98%, 99%, 99.5%, or more of the total protein of the composition will be Factor H. In one preferred embodiment, at least 96% of the total protein of the composition will be Factor H. In a preferred embodiment, at least 97% of the total protein of the composition will be Factor H. In another preferred embodiment, at least 98% of the total protein of the composition will be Factor H. In another preferred embodiment, at least 99% of the total protein of the composition will be Factor H.

B. Pharmaceutical Compositions

In one aspect, the present invention provides pharmaceutical compositions of plasma-derived Factor H prepared from materials otherwise discarded during the preparation of other commercially important blood products by plasma fractionation. Pharmaceutical Factor H compositions prepared by the methods provided herein will have high Factor H content and purity. For example, Factor H compositions provided herein may have a protein concentration of at least at or about 1% (w/v) and a Factor H content of greater than at or about 90% purity. These high purity Factor H pharmaceutical compositions and formulations are suitable for therapeutic administration. In certain embodiments, the pharmaceutical compositions provided herein will consist of aqueous formulations of Factor H formulated for therapeutic administration. In other embodiments, the pharmaceutical compositions provided herein will consist of lyophilized formulations of Factor H formulated for therapeutic administration after reconstitution with water for injection (WFI) or a biologically compatible liquid, e.g., a saline or buffered solution.

In one embodiment, the pharmaceutical compositions provided herein are prepared by formulating an aqueous Factor H composition isolated using a method provided herein. Generally, the manufacturing pathway to the formulated composition will include at least one, preferably at least two, most preferably at least three, viral inactivation or removal steps. Non-limiting examples of viral inactivation or removal steps that may be employed with the methods provided herein include, solvent detergent treatment (Horowitz et al., *Blood Coagul Fibrinolysis* 1994 (5 Suppl 3):S21-S28 and Kreil et al., *Transfusion* 2003 (43):1023-1028, the disclosures of which are incorporated by reference herein in their entireties for all purposes), nanofiltration (Hamamoto et al., *Vox Sang* 1989 (56)230-236 and Yuasa et al., *J Gen Virol.* 1991 (72 (pt 8)):2021-2024, the disclosures of which are incorporated by reference herein in their entireties for all purposes), and low pH incubation at high temperatures (Kempf et al., *Transfusion* 1991 (31)423-427 and Louie et al., *Biologicals* 1994 (22):13-19, the disclosure of which is incorporated herein by reference in its entirety for all purposes).

In one embodiment, pharmaceutical compositions of Factor H are provided that are prepared from a Fraction II+III filter cake. In one embodiment, an aqueous composition of Factor H is provided that is prepared by a method comprising the steps of: (i) extracting Factor H from a Fraction II+III filter cake, (ii) optionally performing a first precipitation step to precipitate at least one impurity from the Factor H composition, (iii) optionally performing a second precipitation step to precipitate Factor H from the composition, (iv) optionally performing at least one ion exchange chromatography step, (v) optionally performing at least one heparin affinity chromatography step; (vi) performing at least one viral inactivation or removal step; and (vii) optionally lyophilizing the Factor H composition, thereby preparing a pharmaceutical Factor H composition.

In a preferred embodiment, a pharmaceutical Factor H composition is provided that is prepared by a method comprising the steps of: (a) precipitating proteins from a cryo-poor plasma fraction, in a first precipitation step, with between about 6% and about 10% alcohol at a pH of between about 7.0 and about 7.5 to obtain a first precipitate and a first supernatant; (b) precipitating Factor H from the first supernatant, in a second precipitation step, with between about 20% and about 25% alcohol at a pH of between about 6.7 and about 7.3 to form a second precipitate; (c) re-suspending the second precipitate to form a suspension; (d) mixing finely divided silicon dioxide (SiO2) with the suspension from step (c); (e) filtering the suspension with a filter press, thereby forming a filter cake and a supernatant; (f) extracting Factor H from the filter cake with a Factor H extraction buffer; (g) performing at least one viral inactivation or removal step; and (h) optionally lyophilizing the composition, thereby preparing an aqueous composition of Factor H.

In certain embodiments, Factor H is extracted from the filter cake by re-circulation of an extraction buffer through a filter press containing the filter cake. Generally, the extraction buffer will be re-circulated through the filter cake for at or about between 5 minutes and 2 hours. In a preferred embodiment, the extraction buffer will be re-circulated through the filter cake for at or about between 10 and 60 minutes. In a more preferred embodiment, the extraction buffer will be re-circulated through the filter cake for at or about between 20 and 40 minutes. In another preferred embodiment, the extraction buffer will be re-circulated through the filter cake for at or about 30 minutes. In other embodiments, the extraction buffer will be re-circulated through the filter cake for at least at or about 5, 10, 15, 20, 25, 30, 35, 40, 45, 50, 55, 60, 65, 70, 75, 80, 85, 90, 95, 100, 105, 110, 115, 120, or more minutes.

In another embodiment, pharmaceutical compositions of Factor H are provided that are prepared from a Fraction I precipitate. In one embodiment, an aqueous composition of Factor H is provided that is prepared by a method comprising the steps of: (i) extracting Factor H from a Fraction I precipitate, (ii) optionally performing a first precipitation step to precipitate at least one impurity from the Factor H composition, (iii) optionally performing a second precipitation step to precipitate Factor H from the composition, (iv) optionally performing at least one ion exchange chromatography step, (v) optionally performing at least one heparin affinity chromatography step; (vi) performing at least one viral inactivation or removal step; and (vii) optionally lyophilizing the Factor H composition, thereby preparing a pharmaceutical Factor H composition.

In a preferred embodiment, pharmaceutical compositions of Factor H are provided that are prepared from a Fraction I precipitate. In a particularly preferred embodiment, a Factor H composition is provided that is prepared by a method comprising the steps of: (a) precipitating proteins from a cryo-poor plasma fraction, in a first precipitation step, with between about 6% and about 10% alcohol at a pH of between about 7.0 and about 7.5 to obtain a first precipitate and a first supernatant; and (b) extracting Factor H from the precipitate with a Factor H extraction buffer; and (c) performing at least one viral inactivation or removal step, thereby preparing a pharmaceutical composition of Factor H.

In certain embodiments, Factor H is extracted from the Fraction I precipitate by re-circulation of an extraction buffer through a filter press containing the Fraction I precipitate. Generally, the extraction buffer will be re-circulated through the precipitate for at or about between 5 minutes and 2 hours. In a preferred embodiment, the extraction buffer will be re-circulated through the precipitate for at or about between 10 and 60 minutes. In another preferred embodiment, the extraction buffer will be re-circulated through the precipitate for at or about between 20 and 40 minutes. In another preferred embodiment, the extraction buffer will be re-circulated through the precipitate for at or about 30 minutes. In other embodiments, the extraction buffer will be re-circulated through the precipitate for at least at or about 5, 10, 15, 20, 25, 30, 35, 40, 45, 50, 55, 60, 65, 70, 75, 80, 85, 90, 95, 100, 105, 110, 115, 120, or more minutes.

In certain embodiments, Factor H is extracted from a Fraction I precipitate or Fraction II+III filter cake by the addition of a Factor H extraction buffer, which can be used to re-suspend the Fraction I precipitate or Fraction II+III filter cake at a typical ratio of 1 part precipitate to at or about between 25 and 30 parts of extraction buffer. In other embodiments, the re-suspension ratio is at or about between 1:4 and 1:40, or at or about between 1:8 and 1:30, or at or about between 1:10 and 1:20, or at or about between 1:12 and 1:18, or at or about between 1:13 and 1:17, or at or about between 1:14 and 1:16. In one embodiment, the re-suspension ratio is at or about 1:25. In another embodiment, the re-suspension ratio is at or about 1:30. In certain embodiments, the ratio may be at or about 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, or higher. In a preferred embodiment, Factor H is extracted by re-circulation of the extraction buffer through a filter or filter press containing the Fraction I precipitate or Fraction II+III filter cake.

In certain embodiments, a pharmaceutical composition of Factor H is provided, wherein the Factor H composition is prepared using a purification method described herein, wherein the method comprises the addition of one or more solutions that would otherwise be introduced into a plasma fraction by fluent addition, by a method that finely disperses or that rapidly disperses the solution at the point of addition. For example, in certain embodiments the method will comprise the introduction of alcohol (e.g., ethanol) into a plasma fraction by spraying. In other embodiments, solutions that may be added to a plasma fraction by spraying include, without limitation, a pH modifying solution, a solvent solution, a detergent solution, a dilution buffer, a conductivity modifying solution, and the like. In a preferred embodiment, one or more alcohol precipitation steps is performed by the addition of alcohol to a plasma fraction by spraying. In a second preferred embodiment, one or more pH adjustment steps is performed by the addition of a pH modifying solution to a plasma fraction by spraying.

In certain embodiments, an aqueous Factor H composition is provided that is prepared by a purification method described herein, wherein the method comprises adjusting the pH of a plasma fraction being precipitated after and/or concomitant with the addition of the precipitating agent (e.g., alcohol or polyethylene glycol). In some embodiments, a process improvement is provided in which the pH of a plasma fraction being actively precipitated is maintained throughout the entire precipitation incubation or hold step by continuous monitoring and adjustment of the pH. In preferred embodiments the adjustment of the pH is performed by the spray addition of a pH modifying solution.

In one embodiment, the present invention provides pharmaceutical Factor H compositions comprising a protein concentration of between about 10 g/L and about 250 g/L. In certain embodiments, the protein concentration of the Factor H composition is at or about between 50 g/L and 200 g/L, or at or about between 70 g/L and 150 g/L, or at or about between 90 g/L and 120 g/L, or at or about between 30 g/L and 70 g/L, or at or about between 40 g/L and 60 g/L or any suitable concentration within these ranges, for example at or about 10 g/L, or at or about 15 g/L, 20 g/L, 25 g/L, 30 g/L, 35 g/L, 40 g/L, 45 g/L, 50 g/L, 55 g/L, 60 g/L, 65 g/L, 70 g/L, 75 g/L, 80 g/L, 85 g/L, 90 g/L, 95 g/L, 100 g/L, 105 g/L, 110 g/L, 115 g/L, 120 g/L, 125 g/L, 130 g/L, 135 g/L, 140 g/L, 145 g/L, 150 g/L, 155 g/L, 160 g/L, 165 g/L, 170 g/L, 175 g/L, 180 g/L, 185 g/L, 190 g/L, 195 g/L, 200 g/L, 205 g/L, 210 g/L, 215 g/L, 220 g/L, 225 g/L, 230 g/L, 235 g/L, 240 g/L, 245 g/L, 250 g/L, or higher. In a preferred embodiment, Factor H compositions having high protein concentrations will also high levels of purity. In one embodiment, at least 90% of the protein in the composition will be Factor H. In a preferred embodiment, at least 95% of the protein in the composition will be Factor H.

In one embodiment, at least 90% of the total protein in a composition provided herein will be Factor H. In a preferred embodiment, at least 95% of the total protein in a composition provided herein will be Factor H. In other embodiments, at least 90%, 91%, 92%, 93%, 94%, 95%, 96%, 97%, 98%, 99%, 99.5%, or more of the total protein of the composition will be Factor H. In one preferred embodiment, at least 96% of the total protein of the composition will be Factor H. In a preferred embodiment, at least 97% of the total protein of the composition will be Factor H. In another preferred embodiment, at least 98% of the total protein of the composition will be Factor H. In another preferred embodiment, at least 99% of the total protein of the composition will be Factor H.

In one embodiment, the present invention provides a pharmaceutical preparation comprising as active ingredient a preparation of Factor H as provided herein and a pharmaceutically acceptable carrier. In one embodiment, the Factor H preparation is prepared by a method comprising (a) performing Cohn fractionation to obtain Fraction II+III precipitate and preparing a suspension of the combined precipitates, (b) filtering the re-suspended Fraction II+III precipitates to obtain the filter cake discard left behind after filtration of the Fraction II+III suspension; (c) extracting the filter cake according to a method comprising the steps of: (i) dissolving the filter cake in a suitable buffer of appropriate ionic strength for a time sufficient to dissolve the protein caked on said filter cake; (ii) diluting said dissolved protein with additional buffer, (iii) removing debris from the diluted protein, (iv) purifying Factor H protein from said diluted protein preparation by subjecting the diluted protein to ultrafiltration on a 0.45 µm filter to produce a filtrate containing Factor H; (v) subjecting the filtrate containing Factor H to anion exchange chromatography using a NaCl gradient (50-500 mM) in the running buffer to produce a pooled crude Factor H fraction; and (vi) purifying Factor H from said crude Factor H preparation by Heparin Sepharose™ chromatography using a gradient of NaCl (50-500 mM).

The pharmaceutical compositions provided herein will typically comprise one or more buffering agents or pH stabilizing agents suitable for intravenous, intravitreal, subcutaneous, and/or intramuscular administration. Non-limiting examples of buffering agents suitable for formulating a Factor H composition provided herein include glycine, histidine, or other amino acids, salts like citrate, phosphate, acetate, glutamate, tartrate, benzoate, lactate, gluconate, malate, succinate, formate, propionate, carbonate, or any combination thereof adjusted to an appropriate pH. Generally, the buffering agent will be sufficient to maintain a suitable pH in the formulation for an extended period of time.

In some embodiments, the concentration of buffering agent in the formulation will be at or about between 5 mM and 500 mM. In certain embodiments, the concentration of the buffering agent in the formulation will be at or about 5 mM, 10 mM, 15 mM, 20 mM, 25 mM, 50 mM, 75 mM, 100 mM, 125 mM, 150 mM, 175 mM, 200 mM, 225 mM, 250 mM, 275 mM, 300 mM, 325 mM, 350 mM, 375 mM, 400 mM, 425 mM, 450 mM, 475 mM, 500 mM or higher.

In certain embodiments, the pH of the formulation will be at or about between about pH 4.0 and pH 8.0.

In some embodiments, the pharmaceutical compositions provided herein may optionally further comprise an agent for adjusting the osmolarity of the composition. Non-limiting examples of osmolarity agents include mannitol, sorbitol, glycerol, sucrose, glucose, dextrose, levulose, fructose, lactose, polyethylene glycols, phosphates, sodium chloride, potassium chloride, calcium chloride, calcium gluconoglucoheptonate, dimethyl sulfone, and the like.

In some embodiments, the formulations provided herein will have osmolarities that are comparable to physiologic osmolarity, about 285 to 295 mOsmol/kg (Lacy et al., *Drug Information Handbook—Lexi-Comp* 1999:1254). In certain embodiments, the osmolarity of the formulation will be at or about between 200 and 350 mOsmol/kg, preferably at or about between 240 and 300 mOsmol/kg. In particular embodiments, the osmolarity of the formulation will be at or about 200 mOsmol/kg, or 210 mOsmol/kg, 220 mOsmol/kg, 230 mOsmol/kg, 240 mOsmol/kg, 245 mOsmol/kg, 250 mOsmol/kg, 255 mOsmol/kg, 260 mOsmol/kg, 265 mOsmol/kg, 270 mOsmol/kg, 275 mOsmol/kg, 280 mOsmol/kg, 285 mOsmol/kg, 290 mOsmol/kg, 295 mOsmol/kg, 300 mOsmol/kg, 310 mOsmol/kg, 320 mOsmol/kg, 330 mOsmol/kg, 340 mOsmol/kg, 340 mOsmol/kg, or 350 mOsmol/kg. In yet other embodiments, the osmolarity of the formulation will be higher, for example at or about between 200 and 1000 mOsmol/kg, or at or about 400 mOsmol/kg, 450 mOsmol/kg, 500 mOsmol/kg, 550 mOsmol/kg, 600 mOsmol/kg, 650 mOsmol/kg, 700 mOsmol/kg, 750 mOsmol/kg, 800 mOsmol/kg, 850 mOsmol/kg, 900 mOsmol/kg, 950 mOsmol/kg, 1000 mOsmol/kg, or higher.

The Factor H formulations provided herein are generally stable in liquid form for an extended period of time. In certain embodiments, the formulations are stable for at least at or about 3 months at room temperature, or at least at or about 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 months or more at room temperature. The formulation will also generally be stable for at least at or about 18 months under refrigerated conditions (typically between about 2° C. and about 8° C.), or for at least at or about 21, 24, 27, 30, 33, 36, 39, 42, 45, 48, 51, 54, 57, 60 months or more under refrigerated conditions.

In other embodiments, the Factor H formulations provided herein are generally stable in lyophilized form for an extended period of time. In certain embodiments, the formulations are stable for at least at or about 3 months at room temperature, or at least at or about 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, or 48 months at room temperature. The formulation will also generally be stable for at least at or about 18 months under refrigerated conditions (typically between about 2° C. and about 8° C.), or for at least at or about 21, 24, 27, 30, 33, 36, 39, 42, 45, 48, 51, 54, 57, or 60 months under refrigerated conditions.

In one aspect, the present invention is also directed to compositions containing Factor H purified according to the present invention and a pharmaceutically acceptable carrier for systemic or local ocular administration is administered to a mammal in need thereof. The compositions may further comprise additional therapeutic compounds that may be useful in the treatment of AMD, such as for example VEGF inhibitors, complement factor D inhibitor, such as BCX-1470 and the like. The therapeutic compositions are formulated in accordance with methods known in the art for the particular route of administration desired.

According to the methods of the present invention, a composition comprising a Factor H purified according to the methods described herein and a pharmaceutically acceptable carrier for systemic or local administration is administered to a mammal in need thereof.

The compositions administered according to the present invention comprise a pharmaceutically effective amount, or therapeutically effective amount, of Factor H either alone or in combination with another therapeutic agent. As used herein, a "pharmaceutically effective amount" or "therapeutically effective amount" is an amount of active agent that is sufficient to reduce complement activation and limit the progression of pathology in various settings such as AMD, HUS, MPGN and others. In some aspects, the therapeutically effective amount is reduces or prevents AMD and/or loss of visual acuity associated with AMD. Generally, for compositions intended to be administered systemically for the treatment of AMD, the total amount of Factor H will be about 0.01-100 mg/kg. For local administration, the preferred concentration of Factor H in the composition will be from about 0.01% to about 10% (w/v).

V. Methods of Treatment

In one aspect, the present invention provides methods for treating a disease or disorder associated with a Factor H dysfunction or abnormal alternative pathway complement activity in a subject in need thereof by administering a therapeutically effective dose of a Factor H composition prepared from materials otherwise discarded during the preparation of other commercially important blood products by plasma fractionation.

In one embodiment, a method is provided for treating a disease or disorder associated with a Factor H dysfunction or abnormal alternative pathway complement activity in a subject in need thereof by administering a therapeutically effective dose of a Factor H composition prepared from a Fraction II+III filter cake or a Fraction I precipitate.

In one embodiment, a method is provided for treating a disease or disorder associated with a Factor H dysfunction or abnormal alternative pathway complement activity in a subject in need thereof by administering to the subject a therapeutically effective dose of a Factor H composition prepared by a method comprising the steps of: (i) extracting Factor H from a Fraction II+III filter cake, (ii) optionally performing a first precipitation step to precipitate at least one impurity from the Factor H composition, (iii) optionally performing a second precipitation step to precipitate Factor H from the composition, (iv) optionally performing at least one ion exchange chromatography step, (v) optionally performing at least one heparin affinity chromatography step; (vi) performing at least one viral inactivation or removal step; and (vii) optionally lyophilizing the Factor H composition, thereby preparing a composition of Factor H suitable for use in treating a disease or disorder associated with a Factor H dysfunction or abnormal alternative pathway complement activity.

In a preferred embodiment, a method is provided for treating a disease or disorder associated with a Factor H dysfunction or abnormal alternative pathway complement activity in a subject in need thereof by administering to the subject a therapeutically effective dose of a Factor H composition prepared by a method comprising the steps of: (a) precipitating proteins from a cryo-poor plasma fraction, in a first precipitation step, with between about 6% and about 10% alcohol at a pH of between about 7.0 and about 7.5 to obtain a first precipitate and a first supernatant; (b) precipitating Factor H from the first supernatant, in a second precipitation step, with between about 20% and about 25% alcohol at a pH of between about 6.7 and about 7.3 to form a second precipitate; (c) re-suspending the second precipitate to form a suspension; (d) mixing finely divided silicon dioxide ($SiO_2$) with the suspension from step (c); (e) filtering the suspension with a filter press, thereby forming a filter cake and a supernatant; and (f) extracting Factor H from the filter cake with a Factor H extraction buffer; (g) performing at least one viral inactivation or removal step; and (h) optionally lyophilizing the composition, thereby preparing a composition of Factor H suitable for use in treating a disease or disorder associated with a Factor H dysfunction or abnormal alternative pathway complement activity.

In another embodiment, a method is provided for treating a disease or disorder associated with a Factor H dysfunction or abnormal alternative pathway complement activity in a subject in need thereof by administering to the subject a therapeutically effective dose of a Factor H composition prepared by a method comprising the steps of: (i) extracting Factor H from a Fraction I precipitate, (ii) optionally performing a first precipitation step to precipitate at least one impurity from the Factor H composition, (iii) optionally performing a second precipitation step to precipitate Factor H from the composition, (iv) optionally performing at least one ion exchange chromatography step, (v) optionally performing at least one heparin affinity chromatography step; (vi) performing at least one viral inactivation or removal step; and (vii) optionally lyophilizing the Factor H composition, thereby preparing a composition of Factor H suitable for use in treating a disease or disorder associated with a Factor H dysfunction or abnormal alternative pathway complement activity.

In a preferred embodiment, a method is provided for treating a disease or disorder associated with a Factor H dysfunction or abnormal alternative pathway complement activity in a subject in need thereof by administering to the subject a therapeutically effective dose of a Factor H composition prepared by a method comprising the steps of: (a) precipitating proteins from a cryo-poor plasma fraction, in a first precipitation step, with between about 6% and about 10% alcohol at a pH of between about 7.0 and about 7.5 to obtain a first precipitate and a first supernatant; (b) extracting Factor H from the precipitate with a Factor H extraction buffer, (c) performing at least one viral inactivation or removal step; and (d) optionally lyophilizing the composition, thereby preparing a composition of Factor H suitable for use in treating a disease or disorder associated with a Factor H dysfunction or abnormal alternative pathway complement activity.

In one embodiment, the present invention provides a therapeutically effective dose of a Factor H composition prepared by a method disclosed herein for use in a method for treating a disease associated with Factor H dysfunction in a subject in need thereof. In one embodiment, the Factor H composition is prepared by extracting Factor H from a Fraction I precipitate. In another embodiment, the Factor H composition is prepared by extracting Factor H from a Fraction II+III filter cake. In certain embodiments, a method is provided for treating a disease or disorder associated with a Factor H dysfunction in a subject in need thereof by administering to the subject a therapeutically effective dose of a Factor H composition provided herein. In certain embodiments, the disease or disorder associated with a Factor H dysfunction is selected from atypical haemolytic uremic syndrome (aHUS), age-related macular degeneration (AMD), membranoproliferative glomulonephritis type II (MPGNII), myocardial infarction, coronary heart disease/coronary artery disease (CAD/CHD), and Alzheimer's disease. In one particular embodiment, the disease is atypical haemolytic uremic syndrome (aHUS). In another particular embodiment, the disease is age-related macular degeneration (AMD). In yet another particular embodiment, the disease is membranoproliferative glomulonephritis type II (MPGNII).

In one embodiment, the present invention provides a therapeutically effective dose of a Factor H composition prepared by a method disclosed herein for use in a method for treating a disease associated with abnormal alternative pathway complement activity in a subject in need thereof. In one embodiment, the Factor H composition is prepared by extracting Factor H from a Fraction I precipitate. In another embodiment, the Factor H composition is prepared by extracting Factor H from a Fraction II+III filter cake. In certain embodiments, a method is provided for treating a disease or disorder associated with a abnormal alternative pathway complement activity in a subject in need thereof by administering to the subject a therapeutically effective dose of a Factor H composition provided herein. In certain embodiments, the disease or disorder associated with abnormal alternative pathway complement activity is selected from an autoimmune disease (such as rheumatoid arthritis, IgA nephropathy, asthma, systemic lupus erythematosus, multiple sclerosis, Anti-Phospholipid syndrome, ANCA-associated vasculitis, pemphigus, uveitis, myathemia gravis, Hashimoto's thyroiditis), a renal disease (such as IgA nephropathy, hemolytic uremic syndrome, membranoproliferative glomerulonephritis) asthma, Alzheimer disease, adult macular degeneration, proximal nocturnal hemoglobinuria, abdominal aortic aneurism, ischemia reperfusion injury, and sepsis.

The pharmaceutical compositions provided by the invention may be administered alone or in conjunction with other therapeutic agents. These agents may be incorporated as part of the same pharmaceutical.

A. Administration

In accordance with the present invention, the time needed to complete a course of the treatment can be determined by a physician and may range from as short as one day to more than a month. In certain embodiments, a course of treatment can be from 1 to 6 months.

An effective amount of a Factor H preparation is administered to the subject by any suitable means to treat the disease or disorder. For example, in certain embodiments, Factor H may be administered by intravenous, intraocular, subcutaneous, and/or intramuscular means. In a preferred embodiment, a method for treating age-related macular degeneration in a subject in need thereof is provided comprising the intraocular administration of a Factor H composition to the patient.

In certain embodiments, the Factor H compositions provided herein can be administered either systemically or locally. Systemic administration includes: oral, transdermal, subdermal, intraperitioneal, subcutaneous, transnasal, sublingual, or rectal. The most preferred systemic route of administration is oral. Local administration for ocular administration includes: topical, intravitreal, periocular, transcleral, retrobulbar, juxtascleral, sub-tenon, or via an intraocular device. Preferred methods for local delivery include transscleral delivery to the macula by posterior juxtascleral administration; via intravitreal injection; or via cannula, such as that described in U.S. Pat. No. 6,413,245, the disclosure of which is incorporated by reference herein in its entirety for all purposes. Alternatively, the inhibitors may be delivered via a sustained delivery device implanted intravitreally or transsclerally, or by other known means of local ocular delivery.

In certain embodiments, the term "effective amount" refers to an amount of a Factor H preparation that results in an improvement or remediation of disease or condition in the subject. An effective amount to be administered to the subject can be determined by a physician with consideration of individual differences in age, weight, the disease or condition being treated, disease severity and response to the therapy. In certain embodiments, an Factor H preparation can be administered to a subject at dose of at or about between 5 mg/kilogram and 2000 mg/kilogram per administration. In certain embodiments, the dose may be at least at or about 5 mg/kg, or at least at or about 10 mg/kg, or at least at or about 20 mg/kg, 30 mg/kg, 40 mg/kg, 50 mg/kg, 60 mg/kg, 70 mg/kg, 80 mg/kg, 90 mg/kg, 100 mg/kg, 125 mg/kg, 150 mg/kg, 175 mg/kg, 200 mg/kg, 250 mg/kg, 300 mg/kg, 350 mg/kg, 400 mg/kg, 450 mg/kg, 500 mg/kg, 550 mg/kg, 600 mg/kg, 650 mg/kg, 700 mg/kg, 750 mg/kg, 800 mg/kg, 850 mg/kg, 900 mg/kg, 950 mg/kg, 1000 mg/kg, 1100 mg/kg, 1200 mg/kg, 1300 mg/kg, 1400 mg/kg, 1500 mg/kg, 1600 mg/kg, 1700 mg/kg, 1800 mg/kg, 1900 mg/kg, or 2000 mg/kg. The dosage and frequency of Factor H treatment will depend upon, among other factors, the disease or condition being treated and the severity of the disease or condition in the patient.

B. Age-Related Macular Degeneration (AMD)

In a preferred embodiment, the present invention provides a method of treating age-related macular degeneration in a subject in need thereof by administering to the subject a therapeutically effective dose of a Factor H composition provided herein.

Age-related macular degeneration (AMD) is the number one cause of blindness for the elderly population over 60 years of age. Today, it is estimated that 35-40% of those over 75 years of age have some degree of AMD. It has been estimated that approximately 50 million people are affected world-wide, with 10 million in the US alone. Currently, about 155,000 new diagnoses of AMD are made every year. As the worldwide population continues to age, the number of annual diagnoses are expected to triple by the year 2020. It is a devastating disease that destroys central vision in the affected individuals, robbing them of their ability to perform activities necessary for everyday life such as reading and driving.

AMD is a slow, progressive disease that involves cells of the outer retinal layers (including photoreceptors and the retinal pigment epithelial (RPE) cells that support the photoreceptors), as well as cells in the adjacent vascular layer of the eye known as the choroid. Macular degeneration is characterized by the breakdown of the macula, a small portion of the central retina (about 2 mm in diameter) responsible for high-acuity vision. Late-onset macular degeneration (i.e., AMD) is generally defined as either "dry" or "wet." The wet ("exudative") neovascular form of AMD affects approximately 10% of those with the disease, and is characterized by abnormal blood vessels growing from the choriocapillaris through the RPE, typically resulting in hemorrhage, exudation, scarring, and/or serous retinal detachment. Approximately 90% of patients with AMD have the non-neovascular, or dry form of the disease, which is characterized by atrophy of the RPE and loss of macular photoreceptors.

AMD is characterized by the presence of deposits of debris-like material, termed "drusen," that accumulate on Bruch's membrane, a multilayered composite of extracellular matrix components separating the RPE (the outermost layer of the retina) from the underlying choroid. Drusen can be observed by funduscopic eye examination. These deposits have been extensively characterized in microscopic studies of donor eyes from patients with AMD. The deposits observed in the living eye upon clinical examination are classified as either soft drusen or hard drusen, according to several criteria including relative size, abundance, and shape of the deposits. Histochemical and immunocytochemical studies have shown that drusen contain a variety of lipids, polysaccharides, glycosaminoglycans and proteins.

Presently, there no known cure for AMD, although several types of treatments has been shown to be effective at managing the disease. Laser photocoagulation of abnormal vessels in the wet form of the disease is the standard treatment. This treatment is limited by the fact that only well-delineated neovascular lesions can be treated in this way and that 50% of patients will suffer recurrence of the leakage from the vessels (Fine et al., 2000). Because of the energy of the laser required for this treatment, the photoreceptors in the treated area will also die, and the patient will also often suffer central blindness immediately after the treatment. New neovascular lesions will eventually develop, requiring repeated treatments. Other interventions include changing lifestyles by cessation of smoking and beginning therapy with antioxidants. Antiangiogenic treatments using VEGF inhibitors e.g., intravitrial injection of ranibizumab or bevacizumab also have been suggested.

Recently it was discovered that about 35% of individuals carry at an at-risk single nucleotide polymorphism (SNP) in one or both copies of their Factor H gene. Homozygous individuals have an approximately sevenfold increased chance of developing age-related macular degeneration, while heterozygotes have a two-to-threefold increased likelihood of developing the disease. This SNP, located in CCP module 7 of Factor H, has been shown to affect the interactions between Factor H and both C-reactive protein and heparin indicating a causal relationship between the SNP and disease. The polymorphism is a Y420H polymorphism.

In one aspect, the present invention provides a method for limiting complement activation resulting in delayed progression or onset of the development of age related macular degeneration (AMD) in a subject, comprising administering a therapeutically effective amount of Factor H preparation provided herein. In one embodiment, the Factor H preparation is prepared by a method comprising (a) performing Cohn fractionation to obtain Fraction II+III precipitates and preparing a suspension of the combined precipitates, (b) filtering the re-suspended Fraction II+III precipitates to obtain the filter cake discard left behind after filtration of the Fraction II+III suspension; (c) extracting the filter cake according to a method comprising the steps of: (i) dissolving the filter cake in a suitable buffer of appropriate ionic strength for a time sufficient to dissolve the protein caked on said filter cake; (ii) diluting said dissolved protein with additional buffer, (iii) removing debris from the diluted protein, (iv) purifying Factor H protein from said diluted protein preparation by subjecting the diluted protein to ultrafiltration on a 0.45 μm filter to produce a filtrate containing Factor H; (v) subjecting the filtrate containing Factor H to anion exchange chromatography using a NaCl gradient (50-500 mM) in the running buffer to produce a pooled crude Factor H fraction; and (vi) purifying Factor H from said crude Factor H preparation by Heparin Sepharose™ chromatography using a gradient of NaCl (50-500 mM).

In one embodiment of a method for limiting complement activation resulting in delayed progression or onset of the development of age related macular degeneration (AMD) in a subject, the subject does not have any symptoms of AMD.

In another embodiment of a method for limiting complement activation resulting in delayed progression or onset of the development of age related macular degeneration (AMD) in a subject, the subject has drusen.

In another embodiment of a method for limiting complement activation resulting in delayed progression or onset of the development of age related macular degeneration (AMD) in a subject, the subject is at increased risk of developing AMD.

In another embodiment of a method for limiting complement activation resulting in delayed progression or onset of the development of age related macular degeneration (AMD) in a subject, the administration is intravenous.

In another embodiment of a method for limiting complement activation resulting in delayed progression or onset of the development of age related macular degeneration (AMD) in a subject, the method further comprises treating a subject having signs and/or symptoms of AMD.

In another embodiment of a method for limiting complement activation resulting in delayed progression or onset of the development of age related macular degeneration (AMD) in a subject, the subject has been diagnosed with AMD.

In another aspect, the present invention provides a method of treating a human subject judged to be at risk for the development of age related macular degeneration, comprising the step of administering to the subject a prophylactically or therapeutically effective amount of a Factor H preparation provided herein, and periodically repeating said administration. In one embodiment, the Factor H preparation is prepared by a method comprising (a) performing Cohn fractionation to obtain Fraction II+III precipitates and preparing a suspension of the combined precipitates, (b) filtering the re-suspended Fraction II+III precipitates to obtain the filter cake discard left behind after filtration of the Fraction II+III suspension; (c) extracting the filter cake according to a method comprising the steps of: (i) dissolving the filter cake in a suitable buffer of appropriate ionic strength for a time sufficient to dissolve the protein caked on said filter cake; (ii) diluting said dissolved protein with additional buffer, (iii) removing debris from the diluted protein, (iv) purifying Factor H protein from said diluted protein preparation by subjecting the diluted protein to ultrafiltration on a 0.45 μm filter to produce a filtrate containing Factor H; (v) subjecting the filtrate containing Factor H to anion exchange chromatography using a NaCl gradient (50-500 mM) in the running buffer to produce a pooled crude Factor H fraction; and (vi) purifying Factor H from said crude Factor H preparation by Heparin Sepharose™ chromatography using a gradient of NaCl (50-500 mM).

In one embodiment of a method of treating a human subject judged to be at risk for the development of age related macular degeneration, the administration is repeated for a time effective to delay the progression or onset of the development of macular degeneration in said subject.

In another embodiment of a method of treating a human subject judged to be at risk for the development of age related macular degeneration, the human subject is judged to be at risk for the development of age-related macular degeneration as identified based on the presence of one or more genetic markers associated with development of age-related macular degeneration.

In another embodiment of a method of treating a human subject judged to be at risk for the development of age related macular degeneration, the genetic marker is a polymorphism.

In another embodiment of a method for limiting complement activation resulting in delayed progression or onset of the development of age related macular degeneration (AMD) in a subject, the subject is not diagnosed with AMD.

VI. Examples

The following examples are provided by way of illustration only and not by way of limitation. Those of skill in the art will readily recognize a variety of non-critical parameters that could be changed or modified to yield essentially the same or similar results.

Example 1

Figure 4:
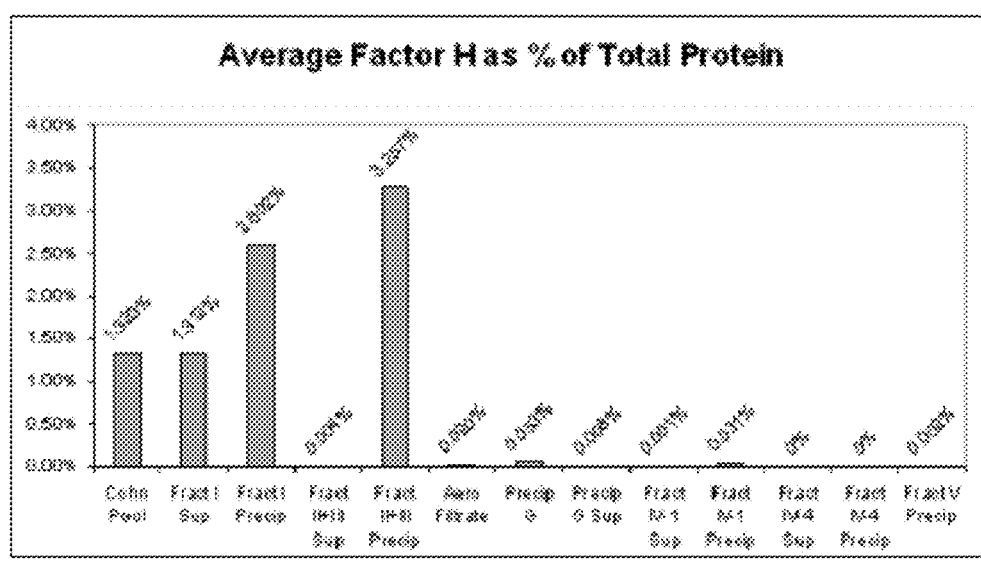
FIG. 4. Amount of Factor H, expressed as a percentage of total protein, found in various fractions of an exemplary plasma fractionation scheme.

To determine an economically beneficial scheme for the manufacture of Factor H from a plasma sample, which allows for the recovery of additional blood factors from the same plasma sample, a 3000 L lot of pooled human plasma was subjected to industrial fractionation according to the scheme outlined in the flow-diagram shown in FIG. 1. The fate of Factor H in the industrial fractionation process was followed by ELISA using an antibody specific for the full-length variant of Factor H. The amount of Factor H determined to be in each fraction is provided in Table 1 and is summarized graphically in FIG. 4.

As seen in Table 1, the 3210 L Cohn pool of pooled human plasma used contained about 2.13 kg of Factor H, as determined by an ELISA assay. The majority of Factor H is present in the Fraction II+III precipitate (1.74 kg), however, insignificant amount are found in the clarified Fraction II+III filtrate, i.e., post precipitate dissolution and Aerosil® treatment. This result suggests that a large portion of the Factor H present in the Cohn pool starting material is captured in the Fraction II+III filter cake. A second significant fraction of Factor H (180 g) is also captured in the Fraction I precipitate, as seen in Table 1.

Example 2

The present example describes experiments performed to determine the feasibility of extracting Factor H from a Fraction II+III filter cake. Briefly, the Fraction II+III filter cake from the plasma fractionation performed in Example 1 was dissolved in a Factor H extraction buffer (25 mM Tris (pH 8.0); 5 mM EDTA; 200 mM NaCl) at a ratio of 25:1 (mL buffer per g filter cake). The conductivity of the resulting suspension was then adjusted by diluting the solution 3:1 with low salt extraction buffer (25 mM Tris (pH 8.0); 5 mM EDTA). Un-dissolved material was cleared from the suspension by centrifugation followed by filtration through a 0.45 μm filter.

Figure 2A:
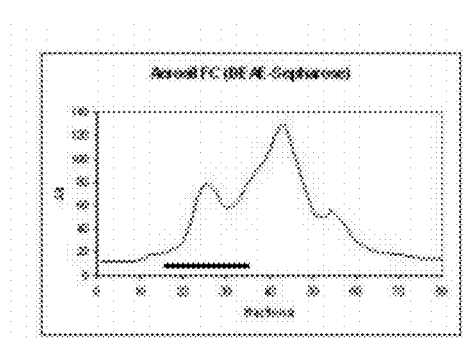
FIG. 2. Chromatographs of (A) DEAE Sepharose™ and (B) Heparin Sepharose™ enrichment steps of a Factor H manufacturing process utilizing a Fraction II+III filter cake as the starting material. SDS-PAGE and Western blot analysis of the (C) DEAE Sepharose™ and (D) Heparin Sepharose™ chromatography.

The clarified filter cake suspension was then loaded onto a DEAE Sepharose™ chromatograph column equilibrated with a low salt buffer (25 mM Tris (pH 8.0); 5 mM EDTA; 50 mM NaCl). A linear gradient from 50 mM NaCl to 500 mM NaCl (25 mM Tris (pH 8.0); 5 mM EDTA; NaCl) was then used to elute the Factor H from the DEAE Sepharose™ column, the eluate of which was collected fractionally as shown by the chromatograph in FIG. 2A. Samples of the eluate fractions were analyzed by SDS-PAGE and Western blot analysis (FIG. 2C) to determine that Factor H eluted off of the anion exchange column in the first of three major peaks.

The first elution peak from the DEAE Sepharose™ chromatography elution, containing primarily Factor H, was pooled based on the chromatograph and gel analysis performed, concentrated, and the conductivity was reduced. The Factor H solution was then loaded onto a Heparin Sepharose™ chromatography column equilibrated with a low salt buffer (25 mM Tris (pH 8.0); 5 mM EDTA; 50 mM NaCl). A linear gradient from 50 mM NaCl to 500 mM NaCl

TABLE 1

Relative amounts of Factor H found in each of the major fractions of an industrial scale plasma fractionation.

| Fraction | Liquid L | Solid kg | Protein mg/mL | Factor H μg/mL | % of Total | Ppt % Protein wt/wt Correction* | Total Factor H kg |
|---|---|---|---|---|---|---|---|
| Cohn Pool | 3210 | | 50.1 | 663.3 | 1.323 | | 2.13 |
| Fraction I Sup | 3480 | | 45.2 | 592.9 | 1.312 | | 2.06 |
| Fraction I Ppt | | 41.1 | 4.1 | 107.7 | 2.602 | 0.17 | 0.18 |
| Fraction II + III Sup | 3880 | | | | 0.004 | | |
| Fraction II + III Ppt | | 124.5 | 21.2 | 689 | 3.257 | 0.43 | 1.74 |
| Filtrate (post Aerosil ®) | 2340 | | | | 0.02 | | |
| Ppt G | | 58.6 | | | 0.053 | | |
| Ppt G Sup | 3140 | | | | 0.008 | | |
| Fraction IV-1 Sup | 3800 | | | | 0.001 | | |
| Fraction IV-1 Ppt | | 76.8 | | | 0.031 | | |
| Fraction IV-4 Sup | 5990 | | | | 0 | | |
| Fraction IV-4 Ppt | | | | | 0 | | |
| Crude V Ppt | | 229.4 | | | 0.002 | | |

Figure 2B:
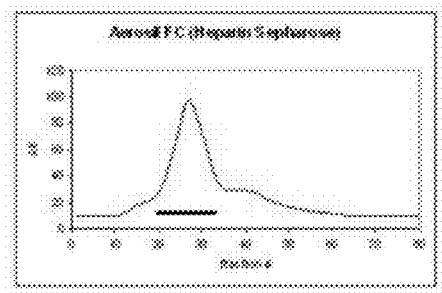
Figure 2C:
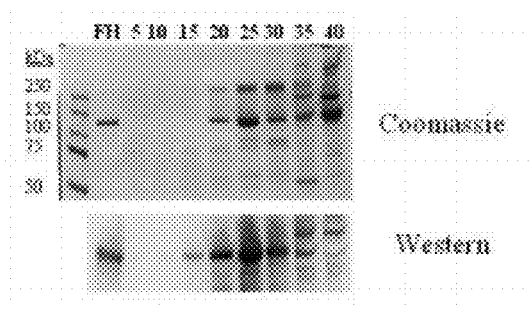
Figure 2D:
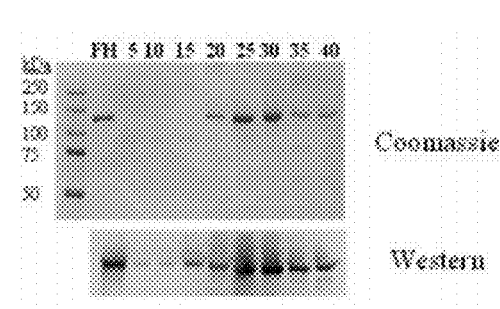

*Determined by freeze drying (25 mM Tris (pH 8.0); 5 mM EDTA; NaCl) was then used to elute the Factor H from the DEAE Sepharose™ column, the eluate of which was collected fractionally as shown by the chromatograph in FIG. 2B. Samples of the eluate fractions were analyzed by SDS-PAGE and Western blot analysis. As can be seen in FIG. 2B, Factor H eluted from the Heparin Sepharose™ column in a single peak, which provides a pure Factor H composition (FIG. 2D).

Example 3

The present example describes experiments performed to determine the feasibility of extracting Factor H from a Fraction I precipitate. Briefly, the Fraction I precipitate from the plasma fractionation performed in Example 1 was dissolved in a Factor H extraction buffer (25 mM Tris; 5 mM EDTA; 200 mM NaCl; pH 8.0) at a ratio of 25:1 (mL buffer per g filter cake). The conductivity of the resulting suspension was then adjusted by diluting the solution 3:1 with low salt extraction buffer (25 mM Tris (pH 8.0); 5 mM EDTA). Un-dissolved material was cleared from the suspension by centrifugation followed by filtration through a 0.45 μm filter.

The clarified Fraction I precipitate suspension was then loaded onto a DEAE Sepharose™ chromatograph column equilibrated with a low salt buffer (25 mM Tris (pH 8.0); 5 mM EDTA; 50 mM NaCl). A linear gradient from 50 mM NaCl to 500 mM NaCl (25 mM Tris (pH 8.0); 5 mM EDTA; NaCl) was then used to elute the Factor H from the DEAE Sepharose™ column, the eluate of which was collected fractionally.

Figure 3:
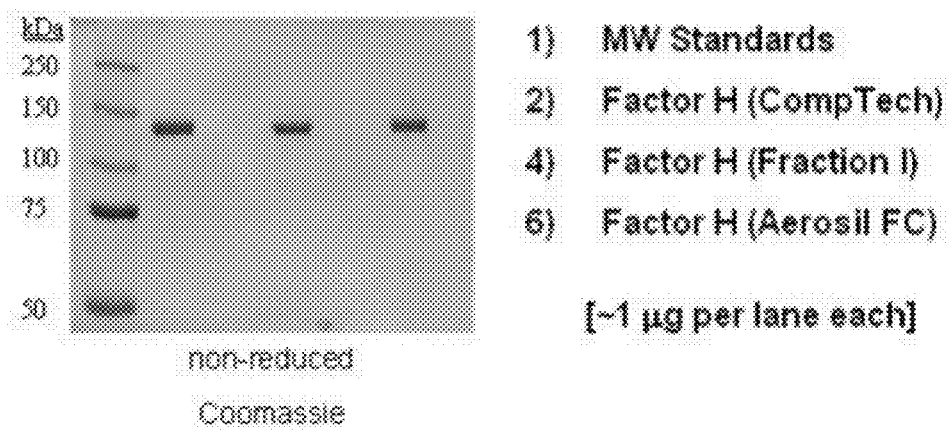
FIG. 3. SDS-PAGE analysis comparing a commercial preparation of Factor H (CompTech; lane 2) to Factor H compositions prepared from Fraction I precipitate (lane 4) and Fraction II+III filter cake (lane 6).

The Factor H peak from the DEAE Sepharose™ chromatography elution was pooled, concentrated, and the conductivity was reduced by buffer exchange. The Factor H solution was then loaded onto a Heparin Sepharose™ chromatography column equilibrated with a low salt buffer (25 mM Tris (pH 8.0); 5 mM EDTA; 50 mM NaCl). A linear gradient from 50 mM NaCl to 500 mM NaCl (25 mM Tris (pH 8.0); 5 mM EDTA; NaCl) was then used to elute the Factor H from the Heparin Sepharose™ column, the eluate of which was collected fractionally. Factor H containing fractions were then pooled and the final composition was analyzed by SDS-PAGE analysis (FIG. 3).

Example 4

The purity and activity of Factor H prepared from the Fraction I precipitate (Example 3) and Fraction II+III filter cake (Example 2) fractions from the plasma fractionation performed in example 1 was investigated. As can be seen from FIG. 3, Factor H prepared from the Fraction I precipitate (lane 4) and Fraction II+III filter cake (lane 6) was at least as pure as a commercial preparation of Factor H (CompTech; lane 2).

Figure 6:
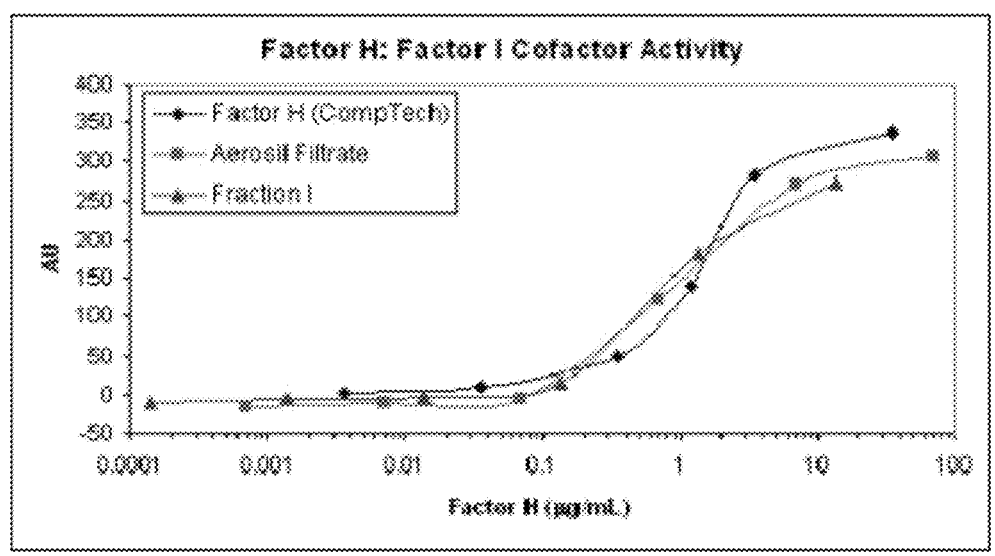
FIG. 6. Comparison of the Factor I cofactor activity of a commercial preparation of Factor H (CompTech; ♦) to Factor H compositions prepared from Fraction I precipitate (▲) and Fraction II+III filter cake (■).

The activity of the purified Factor H compositions was assessed via two methods. First, a Factor I cofactor activity was examined. C3b and Factor I used in the assay were obtained commercially from CompTech. Briefly, C3b was combined with Factor I and various concentrations of Factor H derived from either a commercial source (CompTech; ♦), purified from Fraction I precipitate (Example 3; ▲) or purified from Fraction II+III filter cake (Example 2; ■). The reactions were incubated at 37° C., denatured in Laemmli sample buffer and resolved via SDS-PAGE. The intensities of the α40 fragment of C3b were quantified via densitometry and the resulting activity curves are shown in FIG. 6. As shown, the activity of the purified Factor H, both derived from Fraction I precipitate and from Fraction II+III filter cake, is comparable to a commercial preparation of Factor H. In this regard, the Factor H preparations from Example 2 and 3 appear to have similar specific activities as the commercial Factor H preparation.

Figure 5:
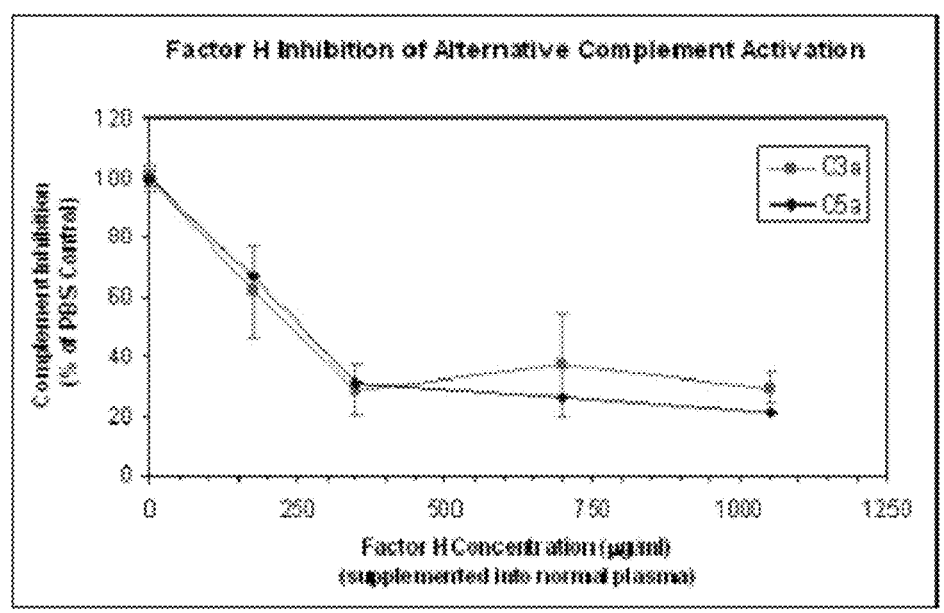
FIG. 5. Factor H inhibition of alternative complement activation using Factor H recovered from a Fraction II+III filter cake.

To further characterize the activity of the purified Factor H compositions, a second activity assay was employed to determine the C3 (■) and C5 (♦) convertase inhibition activity of the preparation. Briefly, an alternative pathway stimulator (Sepharose 4B) was incubated with heparnized plasma spiked with increasing amounts of the Factor H composition purified from Fraction II+III filter cake (Example 2). After incubation, complement was quenched with EDTA and the levels of C3a and C5a were determined via ELISA. As shown in FIG. 5, the Fraction II+III filter cake Factor H preparation demonstrates inhibitory activity against C3a and C5a conversion.

The experimental results provided above in examples 1 to 4 demonstrate that Factor H can be purified from both Fraction I precipitate and Fraction II+III filter cake to yield Factor H compositions having purity and enzymatic activities comparable to currently available commercial preparations (CompTech).

Example 5

Since the Factor H was purified from a large plasma pool, this preparation contains many variants (isoforms) that contribute to the overall activity. An unanticipated finding relates to the percent of His-402 variant in the final preparation of Factor H purified from a Fraction II+III filter cake, which was determined to be approximately 50% via LC-MS (Table 2). The incidence of the His-402 FH isoform in the general population has been reported to range from 7% to 34% (Grassi et al. Human Mutation (2006) 27:921-925), suggesting that the method used above in examples 1 to 3, for preparing Factor H compositions, yields a distinct population of Factor H variants. It was also observed that Factor H, purified in the manner described above, eluted as two sequential peaks (FIG. 2). These two peaks appeared to have differences in their affinity for heparin (due to the difference in their elution time in the linear salt gradient) but a somewhat similar distribution of H403 versus Y402 variants (as shown in Table 2).

TABLE 2

Relative amounts of H402 and Y402 Factor H variants found in a commercial preparation (CompTech) and the Fraction II + III filter cake purification of example 2.

|      | Commercial Preparation | Factor-H (peak 1) | Factor-H (peak 2) |
| ---- | ---------------------- | ----------------- | ----------------- |
| H402 | 50.0%                  | 49.9%             | 52.3%             |
| Y402 | 50.0%                  | 50.1%             | 47.7%             |

Example 6

In order to further explore conditions under which Factor H may be extracted from a Factor II+III filter cake, pooled human plasma samples were fractionated as described in Example 1. After suspension and silicon dioxide ($SiO_2$) treatment of the Fraction II+III precipitate, the Fraction II+III filter cake was collected in a filter press, effectively separating it from the corresponding clarified Fraction II+III suspension. The filter cake, still located within the filter press, was first pre-rinsed with a Factor H extraction buffer outlined below until the pH of the rinsed solution reached 7.0 to displace residual filtrate and to fill the filter press with the appropriate extraction buffer. This is an optional operation to fully recover the filtrate which does not affect Factor H yield in the extract. Factor H was extracted from the filter cake by continuous recirculation of one of two Factor H extraction buffers, extraction buffer A (20 mM Tris (pH 8.0); 5 mM EDTA; 200 mM NaCl) or extraction buffer B (100 mM sodium phosphate (pH 7.5); 150 mM sodium chloride) through the filter press for one hour.

Figure 7:
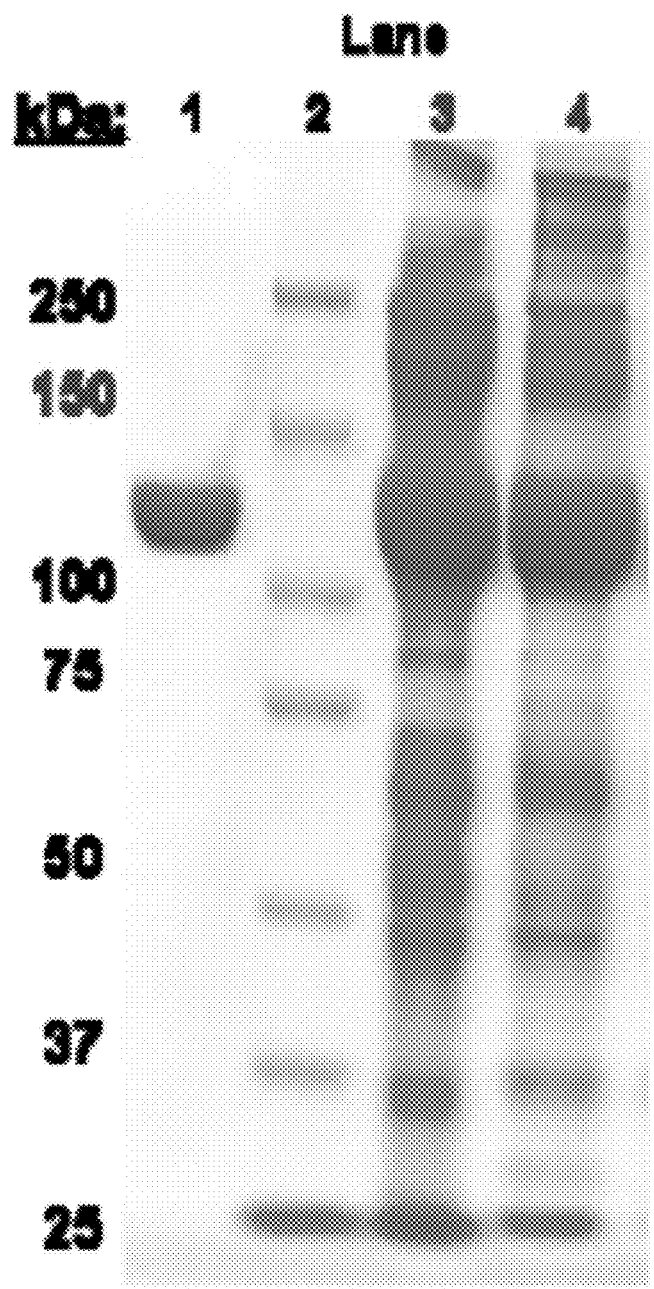
FIG. 7. SDS-PAGE analysis of Factor H extracted from a Fraction II+III filter cake using an EDTA extraction buffer (lane 3; 20 mM Tris (pH 8.0), 5 mM EDTA, 200 mM sodium chloride) or a phosphate extraction buffer (lane 4; 100 mM Sodium phosphate (pH 7.5), 150 mM sodium chloride). Samples were normalized through dilution to 500 µg/ml Factor H content (measured by Enzyme-linked Immunosorbent Assay (ELISA)) before loading to the gel (7.5% Mini-Protean® TGX™ Gel, Bio-Rad®). Lane 1 contains a Factor H standard (1.05 mg/ml, 97% purity, Calbiochem®; total load of 5 µg) and lane 2 contains standard protein molecular weight marker (Precision Plus Protein™ Standards, Bio-Rad®). Both buffer systems extracted the Factor H efficiently.

Analysis of the resulting Fraction II+III filter cake extracts revealed that extraction with buffer A resulted in recovery of 0.39 g Factor H/L plasma and examination of the filter cake revealed that 0.04 g Factor H/L plasma was retained in the filter cake after a one hour extraction. Similarly, extraction with buffer B resulted in recovery of 0.44 g Factor H/L plasma and examination of the filter cake revealed that 0.03 g Factor H/L plasma was retained in the filter cake after a one hour extraction. Consistent with this, SDS-PAGE analysis of the extracted fraction shows that the distribution of proteins and relative amounts of Factor H in both extractions was similar (FIG. 7; lane 1=Factor H standard (CompTech); lane 2=standard protein MW markers; lane 3=buffer A extract; lane 4=buffer B extract). These results suggest that a wide range of buffers may be effective for the extraction of Factor H from a Fraction II+III filter cake.

Example 7

Figure 8:
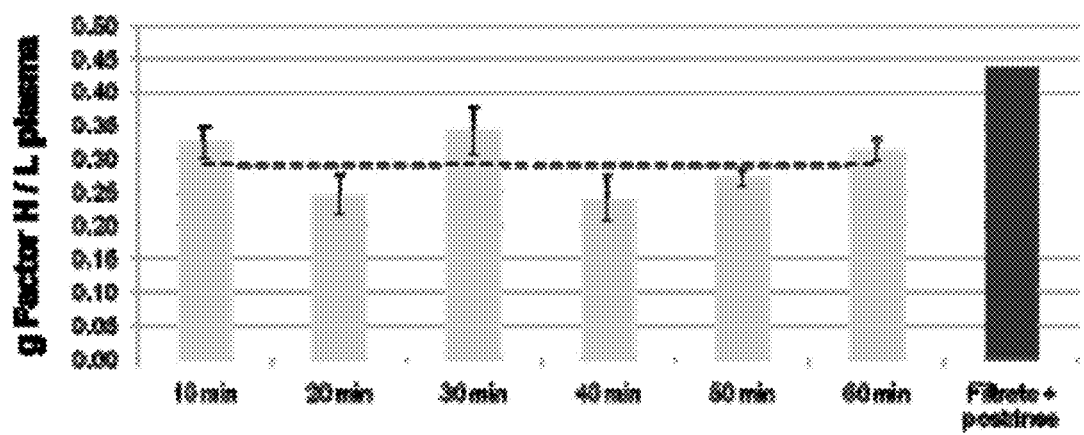
FIG. 8. Quantitation of the amount of Factor H (g FH/L plasma, as measured by ELISA) extracted from a Fraction II+III filter cake by continuous recirculation of an extraction buffer (phosphate/sodium chloride) through the filter for between 10 and 60 minutes. Total average yield for combined filtrate and post-rinse fractions is shown as the last bar.

To investigate the extraction time required for efficient recovery of Factor H from the Fraction II+III filter cake, pooled human plasma samples were fractionated as described in Example 1. After suspension and silicon dioxide (SiO$_2$) treatment of the Fraction II+III precipitate, the Fraction II+III filter cake was collected in a filter press, effectively separating it from the corresponding clarified Fraction II+III suspension. The filter cake, still located within the filter press, was first pre-rinsed with a Factor H extraction buffer (100 mM sodium phosphate (pH 7.5); 150 mM sodium chloride) until the pH of the rinsed solution reached 7.0. Factor H was then extracted from the filter cake by continuous recirculation of the Factor H extraction buffer for between 10 and 60 minutes. The Factor H content was then determined for each of the extractions by ELISA analysis. As seen in FIG. 8, no significant difference in the amount of Factor H extracted from the filter cakes could be seen for extraction times ranging from 10 to 60 minutes. However, post-washing the filter press with one void volume of extraction buffer resulted in an increase in the final Factor H recovery from the filter cake.

Example 8

In order to reduce the volume and potentially remove impurities from the Factor H extract recovered from Fraction II+III filter cake, precipitation experiments were performed to investigate conditions that may be used. Briefly, polyethylene glycol 4000 (PEG 4K) or ethanol was added at varying concentrations to samples of a Factor H filter cake extract, prepared as described in Example 7, and the pH of the solution was adjusted to either 6.0 or 8.0 for the ethanol samples and 7.0 for the PEG samples. The samples containing ethanol were then stirred overnight at −10° C. and the samples containing PEG were stirred overnight at 4° C. The resulting precipitates and supernatants were then separated and the precipitates dissolved in extraction buffer. As seen in Table 3, more protein remained in the supernatant of the 25% ethanol precipitation than in the 12.5%, 17.5%, and 20% PEG precipitations. Consistent with this, the dissolved PEG precipitates contained more protein than did the ethanol precipitate, resulting in cloudier suspensions that may require additional treatment prior to further purification of Factor H by chromatographic methods.

TABLE 3

Factor H contents of precipitates and supernatants resulting from overnight ethanol and PEG precipitation experiments.

| Precipitant | Protein in the Supernatant (mg/ml) | Appearance of the Supernatant | Protein in the Precipitate (mg/ml) | Amount of Precipitate (g/g filtrate) | Appearance of the Dissolved Precipitate |
|---|---|---|---|---|---|
| 12.5% PEG | 1.11 mg/ml | Clear | 10.0 mg/ml | 0.034 g/g filtrate | Very Cloudy |
| 17.5% PEG | 0.5 mg/ml | Clear | 9.3 mg/ml | 0.045 g/g filtrate | Very Cloudy |
| 20% PEG | 0.5 mg/ml | Clear | 9.0 mg/ml | 0.048 g/g filtrate | Very Cloudy |
| 25% Ethanol (pH 7.0) | 1.5 mg/ml | Cloudy | 5.3 mg/ml | 0.070 g/g filtrate | Slightly Cloudy |

Figure 9:
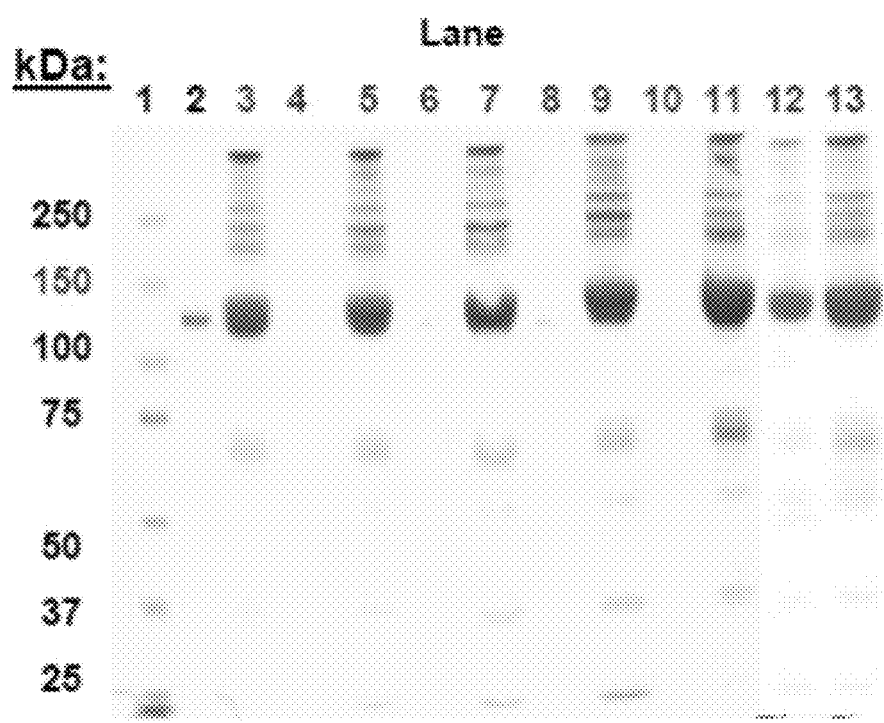
FIG. 9. SDS-PAGE analysis of the resulting protein contents from precipitations performed on Factor H solutions extracted from a Fraction II+III filter cake. Lane 1 contains standard protein molecular weight marker (Precision Plus Protein™ Standards, Bio-Rad®); lane 2 contains a Factor H standard (1.05 mg/ml, 97% purity, Calbiochem®; total load of 1 µg); lanes 3, 5, 7, 9, and 11 contain dissolved precipitates from PEG precipitations (10%, 12.5%, 17.5%, 20%, and 12.5%+0.2% Tween, respectively); lanes 4, 6, 8, and 10 contain supernatants from PEG precipitations (10%, 12.5%, 17.5%, and 20%, respectively); lane 12 contains a supernatant from a 15% ethanol precipitation performed at pH 8.0; and lane 13 contains a dissolved precipitate from a 25% ethanol precipitation performed at pH 6.0. Precipitation with ethanol as well as with PEG are efficient. Only very small amounts of Factor H remained in the supernatants.

The Factor H content of each sample was then determined by ELISA analysis, values for which are given in Table 4. To further analyze the resulting fractions, samples of each supernatant and dissolved precipitate were subjected to SDS-PAGE analysis (FIG. 9). As seen in Table 5, the majority of Factor H is present in the supernatant of the 15% ethanol precipitation performed at pH 8.0, while Factor H is precipitated with 25% ethanol at a pH of 6.0. In one embodiment, a fractional precipitation scheme may be used wherein some impurities are first removed by precipitating the Factor H extract using 15% ethanol and then recovering the Factor H in a second precipitation using 25% ethanol.

TABLE 4

Factor H contents of precipitates and supernatants resulting from overnight ethanol and PEG precipitation experiments.

| Lane # (FIG. 9) | Sample | g Factor H/ L Plasma |
|---|---|---|
| Lane 1 | size marker | |
| Lane 2 | Factor H Standard | |
| Lane 3 | PEG 10% precipitate dissolved | 0.38 |
| Lane 4 | PEG 10% supernatant | |
| Lane 5 | PEG 12.5% precipitate dissolved | 0.43 |
| Lane 6 | PEG 12.5% supernatant | |
| Lane 7 | PEG 17.5% precipitate dissolved | 0.41 |
| Lane 8 | PEG 17.5% supernatant | |
| Lane 9 | PEG 20% precipitate dissolved | 0.42 |
| Lane 10 | PEG 20% supernatant | |
| Lane 11 | PEG 12.5% + 0.2% Tween, precipitate dissolved | 0.4 |

TABLE 4-continued

Factor H contents of precipitates and supernatants resulting from overnight ethanol and PEG precipitation experiments.

| Lane # (FIG. 9) | Sample | g Factor H/ L Plasma |
|---|---|---|
| Lane 12 | 15% EtOH, pH = 8, supernatant | 0.39 |
| Lane 13 | 25% EtOH, pH = 6, precipitate dissolved | 0.43 |

TABLE 5

Fate of Factor H in ethanol precipitations performed at 15% ethanol/pH 8.0 and 25% ethanol/pH 6.0.

| | Yield % of Factor H in filter cake |
|---|---|
| Recycled filter cake (filter press) | 100 |
| EtOH Precipitation 15% pH = 8.0 | |
| EtOH Supernatant | 89 |
| EtOH Precipitate dissolved | 7 |
| EtOH Precipitation 25% pH = 6.0 | |
| EtOH Supernatant | 2 |
| EtOH Precipitate dissolved | 98 |

Example 9

In order to aid with the industrial scale-up for the Factor H purification after extraction, an alternate purification scheme was devised that replaces the salt gradient elution of the chromatography columns with a series of step elutions that are more amenable to a large scale manufacturing process. Briefly, a Factor H extraction was then loaded onto a DEAE Sepharose™ chromatography column equilibrated with a low salt buffer (25 mM Tris; 5 mM EDTA; 65 mM NaCl; pH 8.0). The conductivity of the load was similar to that of the equilibration buffer (about 9 mS/cm). After the load, the column was washed with buffer containing 65 mM NaCl for 5 column volumes (CV) to remove the unbound protein impurities. The flow-through fractions contain very little Factor H as shown by the Western blot results in FIG. 10C.

Figure 10A:
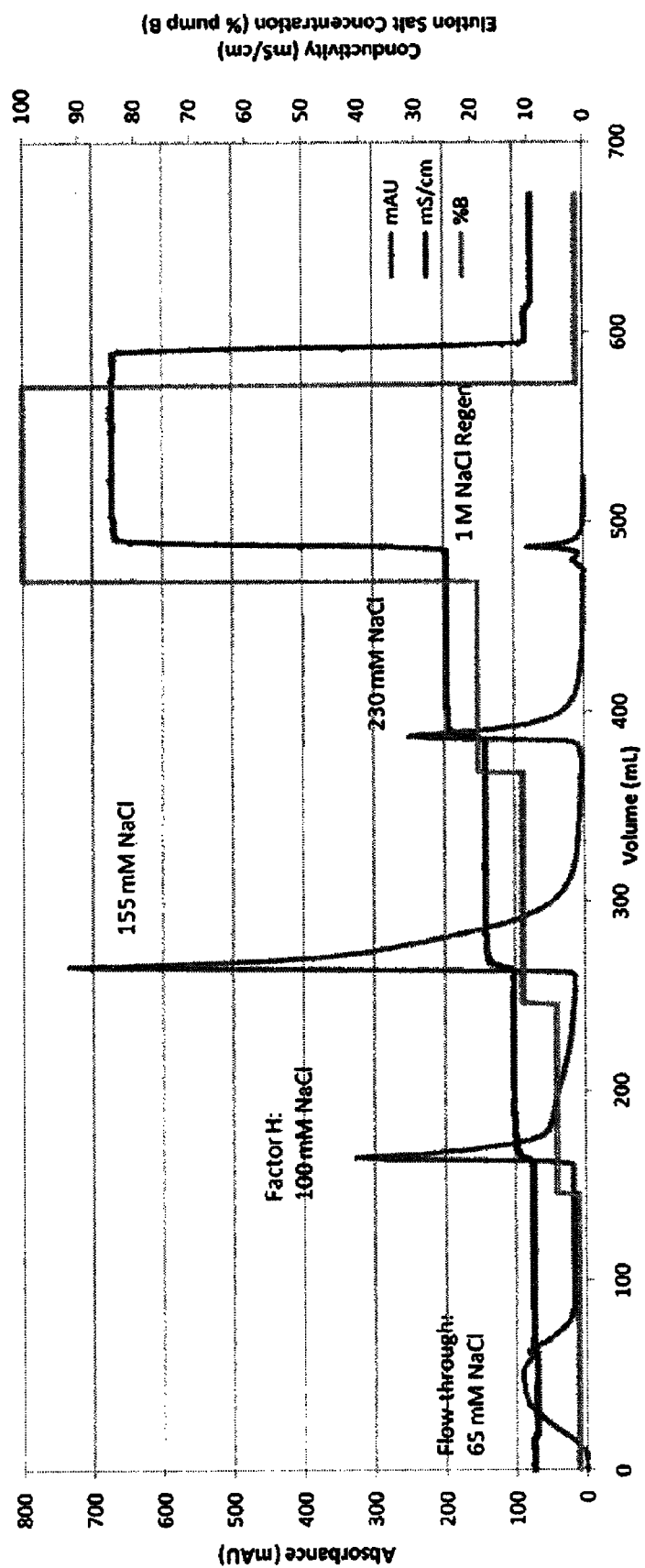
FIG. 10. (A) Chromatograph, (B) SDS-Page Analysis, and (C) Western blot analysis of DEAE chromatography performed with step-wise elution of a Factor H solution extracted from a Fraction II+III filter cake. Lane 1 contains standard protein molecular weight markers; lane 2 contains a sample of the Factor H solution loaded onto the DEAE resin; lanes 3 and 4 contain samples of the flow through from the DEAE load; lane 5 contains a sample of the 100 mM elution peak; lane 6 contains a sample of the 100 mM elution shoulder; lane 7 contains a sample of the 155 mM elution peak; lane 8 contains a sample of the 230 mM elution peak; and lane 9 contains a commercial Factor H standard.
Figure 10B:
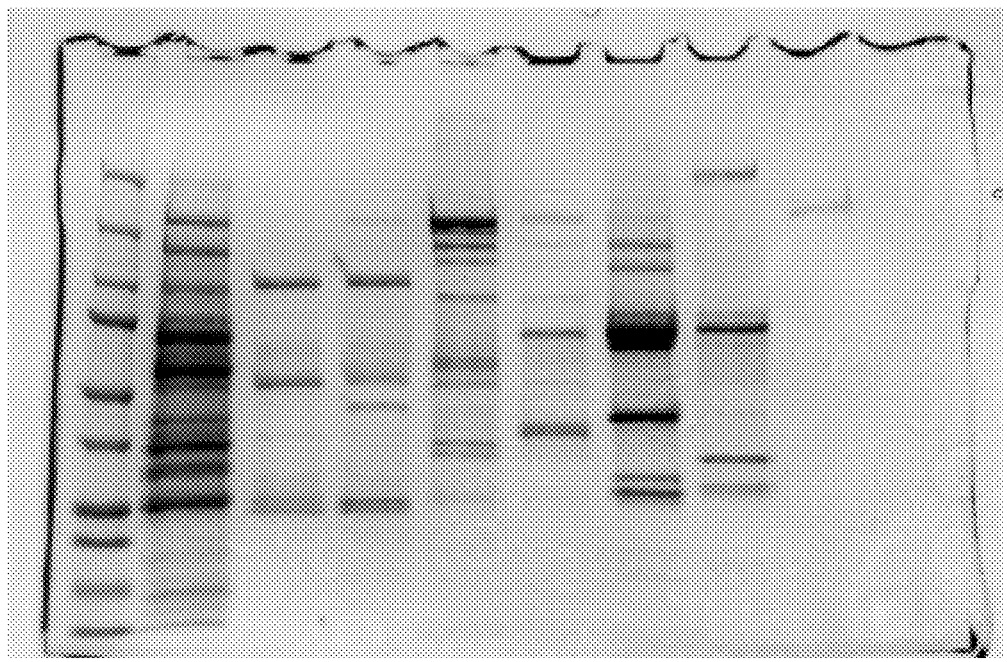
Figure 10C:
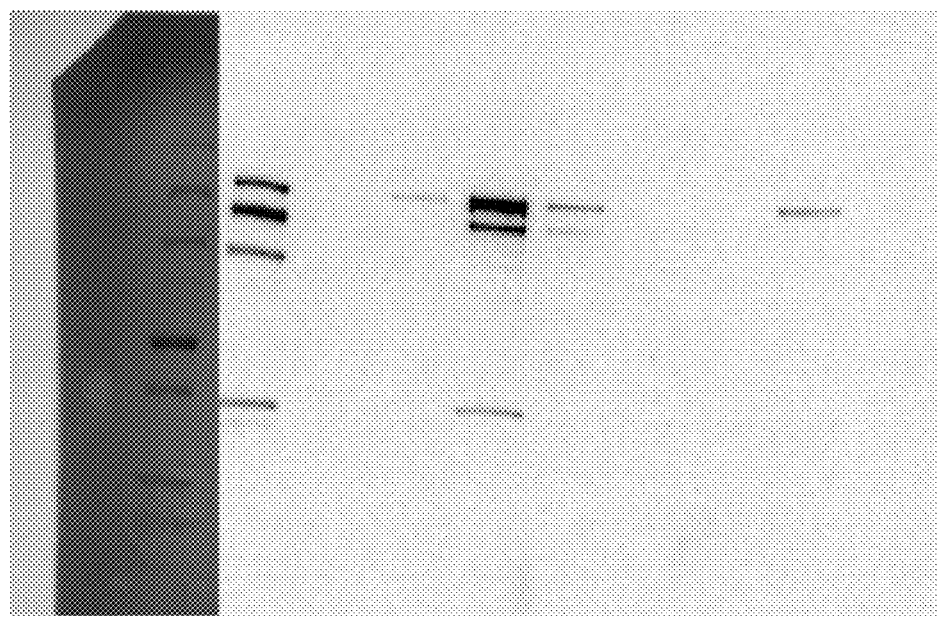

In a first step elution, the salt concentration of the buffer (25 mM Tris (pH 8.0); 5 mM EDTA; 65 mM NaCl) was increased to 100 mM NaCl (conductivity 12.6 mS/cm) for 5 CV to elute Factor H bound to the column. The Factor H came off the column in a sharp peak followed by a shoulder, as seen in the chromatograph provided in FIG. 10A. The corresponding Coomassie stained SDS-PAGE gel (FIG. 10B) and Western blot (FIG. 10C) show the majority of the Factor H in the peak. Analysis of further step elutions performed with buffers containing 155 mM NaCl, 230 mM NaCl, and 1 M NaCl demonstrate that very little Factor H remains bound to the DEAE Sepharose™ resin after the 100 mM NaCl elution (FIG. 10). The major Factor H fractions from the 100 mM NaCl elution were pooled together.

Figure 11A:
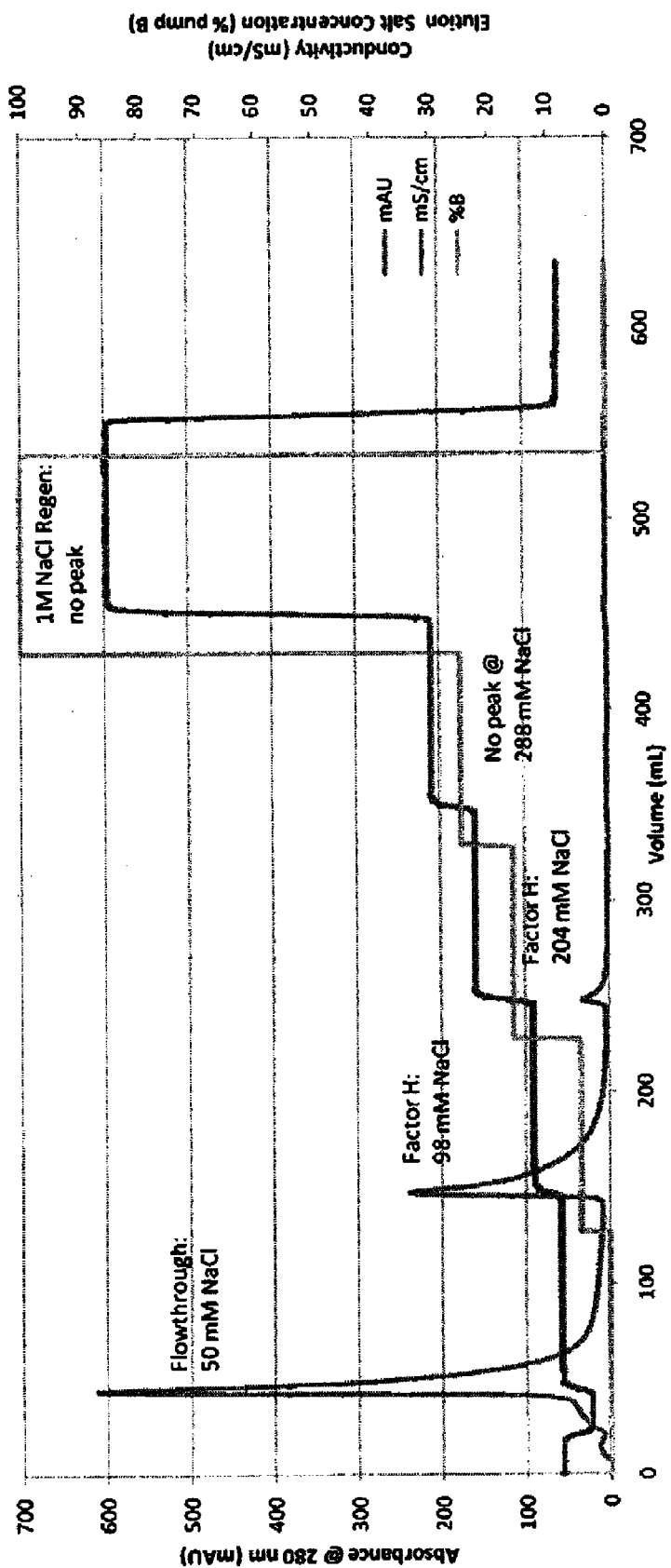
FIG. 11. (A) Chromatograph, (B) SDS-Page Analysis, and (C) Western blot analysis of Heparin Sepharose™ chromatography performed with step-wise elution of a peak Factor H fraction enriched by DEAE chromatography. Lane 1 contains standard protein molecular weight markers; lane 2 contains a sample of the Factor H solution loaded onto the heparin resin; lanes 3, 4, and 5 contain samples of the flow through from the heparin load; lane 6 contains a sample of the 98 mM elution peak; lane 7 contains a sample of the 98 mM elution shoulder; lane 8 contains a sample of the 204 mM elution peak; and lane 9 contains a commercial Factor H standard.
Figure 11B:
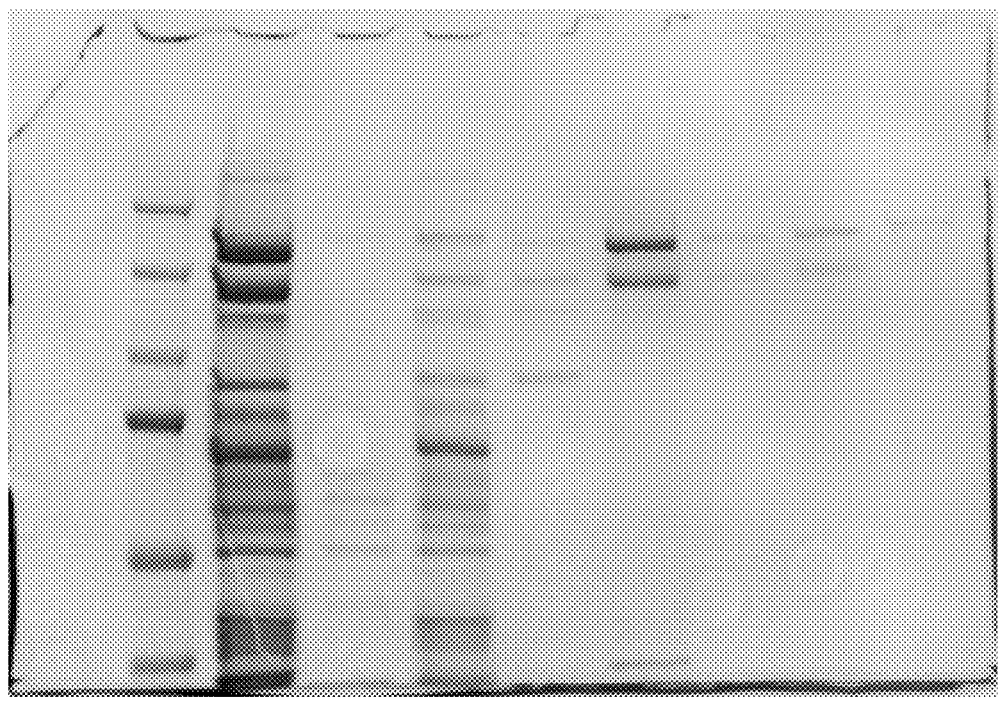
Figure 11C:
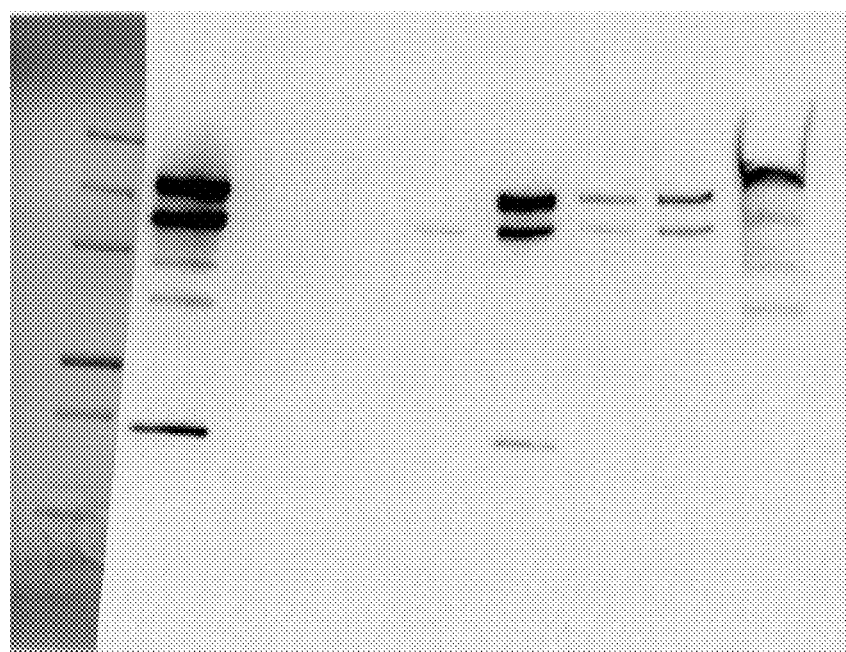

To reduce the salt concentration of the pooled Factor H fractions, the sample was dialyzed against low salt buffer to reduce the conductivity to about 8 mS/cm (around 50 mM NaCl). The sample was then passed through a 0.45 μm filter to remove any particulates. The filtered sample was then loaded onto a Heparin Sepharose™ chromatography column equilibrated with a low salt buffer (25 mM Tris (pH 8.0); 5 mM EDTA; 50 mM NaCl). After the load, the column was washed with buffer containing 50 mM NaCl for 5 column volumes (CV) to remove the unbound protein impurities. The flow-through fractions contain very little Factor H as shown by the Western blot results in FIG. 11C.

In a first step elution, the salt concentration of the buffer (25 mM Tris (pH 8.0); 5 mM EDTA; NaCl) was increased to 98 mM NaCl to elute Factor H from the column. SDS-PAGE (FIG. 11B) and Western blot (FIG. 11C) analysis shows that the resulting Factor H pool is quite pure. There are some low molecular weight impurities that may be removed by a size exclusion polishing or equivalent step. A second elution step was performed with buffer containing 204 mM NaCl and another Factor H peak was eluted off the column. This fraction did not have any detected impurities. Subsequent elution steps at 288 mM and 1 M NaCl did not show any additional protein peaks (FIG. 10A), indicating all Factor H eluted from the column at the elution steps containing 98 mM and 204 mM NaCl. This method can be modified to optimize the process. In one embodiment, all of the Factor H may be eluted in a single step, for example with a single elution with buffer containing greater than 98 mM NaCl. The load and wash may still be performed at 50 mM NaCl, and Factor H elution may be done, for example, with buffer containing 204 mM NaCl. An extended wash at 50 mM NaCl or at a salt concentration of below 98 mM NaCl may be added after loading in an attempt to remove more weakly bound impurities from the Factor H pool.

The above chromatography steps can be modified to use buffer systems other than Tris/EDTA at pH 8. These processes can be adapted for buffers and solutions commonly used in manufacturing of biopharmaceuticals. An example is a purification scheme using phosphate buffer at about pH 7.5. The key parameter to successful purification is manipulation of conductivity or ionic strength to achieve separation of the desired compound. If the pH of the buffer system is changed, some adjustment of the ionic strength will be needed which can be done with standard techniques used in optimization of chromatographic processes.

Example 10

In order to demonstrate that plasma-derived Factor H is efficacious in vivo, an experiment was performed using the Choriodial Neovascularization (CNV) model in mice (a model of AMD in humans). Human FH was isolated to homogeneity as described above (Example 2) and shown to have low endotoxin levels. CNV was induced by laser photocoagulation in C57/B1 male mice with an argon laser (50 um size spots, 0.05 s duration, 250 mW) as described (N. S. Bora, S. Kaliappan, P. Jha, Q. Xu, B. Sivasankar, C. L. Harris, B. P. Morgan and P. S. Bora. J. Immunol. 178:1783-1790 (2007)).

Two groups of 8 animals were treated, Group 1 (controls) received 2 μl intravitreal injection of PBS within 1 hour of the laser treatment while Group 2 (test) received 2 μl intravitreal injection of human FH within 1 hour of the laser treatment. Animals were sacrificed 7 days after laser treatment. Before sacrifice, the mice were perfused through the heart with 0.5 mL of FITC-dextran (Sigma, molecular weight approx. $2 \times 10^6$). The eyes were fixed in normal buffered formalin for 2 hours at 25° C., and the posterior part of the eyes (with the spots) were dissected and additionally stained for elastin using immunohistochemistry. Primary goat polyclonal Abs against elastin (C-21, SC-1751, Lot#J0505, Santa Cruz) in working dilution 1:200 and secondary donkey anti goat Alexa Fluor 594 conjugated Abs (Invitrogen) in working dilution 1:400 were used.

Samples were flat mounted in ProLong antifade reagent (Invitrogen). Laser confocal microscopy was performed using LSM 510 Zeiss microscope. Single image of CNV in each laser injured area were captured and spots with hemorrhagic changes were excluded from the investigation. The area of CNV in μm² was measured using ImageJ program (NIH). Area of laser spots (area of interest, AOI) was manually determined and area of green fluorescence (threshold values 33-255) in area of interest was measured. Mean value of CNV area and standard error for each group was calculated using EXEL program.

The results of this analysis are show below in Table 6. Treatment of the mice with Factor H, following laser ablation of the back of the eye, significantly reduced the level of neovascular response measured on day 7 post treatment (p=0.04).

TABLE 6

Effect of Factor H on the Size of FITC-Dextran Perfused Vessels in Murine CNV Model

| Group | Number of Spots | Area of CNV | Percent of Control |
|---|---|---|---|
| 1 (PBS) | 47 | 3618 ± 561 | — |
| 2 (Factor H) | 43 | 2298 ± 316 | 63.5 |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for preparing an enriched Factor H composition from plasma, the method comprising the steps of:
   (a) precipitating proteins from a cryo-poor plasma fraction, in a first precipitation step, with between about 6% and about 10% alcohol at a pH of between about 7.0 and about 7.5 to obtain a first precipitate and a first supernatant;
   (b) precipitating Factor H from the first supernatant, in a second precipitation, step, with between about 20% and about 30% alcohol at a pH of between about 6.7 and about to form a second precipitate;
   (c) re-suspending the second precipitate to form a suspension;
   (d) mixing finely divided silicon dioxide ($SiO_2$) with the suspension from step (c);
   (e) separating the suspension to form a filter cake and a supernatant; and
   (f) extracting Factor H from the filter cake with a Factor H extraction buffer having a pH of about 4.0-5.5 or about 6.0-9.0,
thereby preparing an enriched Factor 1-1 composition.

2. The method of claim 1, wherein at least one of the first precipitation step or second precipitation step comprises spray addition of alcohol.

3. The method of claim 1, wherein the pH of the solution is modified after the addition of alcohol in at least one of the first precipitation step or second precipitation step by the addition of a pH modifying agent.

4. The method of claim 3, wherein the pH of a precipitation step is modified before and after the addition of alcohol, during and after the addition of alcohol, or before, during, and after the addition of alcohol.

5. The method according to claim 1, wherein the filter cake is separated from the supernatant by filtering the suspension through a filter press.

6. The method of claim 5, wherein the step of extracting Factor H from the filter cake comprises recirculation of a Factor H extraction buffer through the filter press containing the Factor H filter cake.

7. The method of claim 1, wherein the Factor H extraction buffer has a pH of at least 0.3 units different from the isoelectric point of Factor H.

8. The method of claim 1, wherein the enriched Factor H composition is subjected to at least one viral inactivation step.

9. The method of claim 1, further comprising the steps of:
   (g) precipitating impurities from the enriched Factor H composition formed in step (f) to form a supernatant containing Factor H, thereby preparing a further enriched Factor H composition.

10. The method of claim 9, wherein the further enriched Factor H composition is subjected to at least one viral inactivation step.

11. The method of claim 9, wherein the method further comprises the steps of:
   (h) binding Factor H to an anion exchange resin; and
   (i) eluting Factor H from the anion exchange resin with an elution buffer,
thereby forming a first eluate containing Factor H.

12. The method of claim 11, further comprising the steps of:
   (j) binding Factor H from the first eluate to a heparin affinity resin; and
   (k) eluting the Factor H from the heparin affinity resin with an elution buffer,
thereby forming a second eluate containing Factor H.

13. The method of claim 9, further comprising the steps of:
   (l) binding impurities to an anion exchange resin under conditions such that Factor H does not bind to the resin and is collected in the flow through fraction;
   (m) binding Factor H from the flow through fraction to a heparin affinity resin;
   (n) eluting Factor H from the heparin affinity resin to form an eluate;
   (o) binding Factor H from the eluate to an anion exchange resin; and
   (p) eluting Factor H from the anion exchange resin, thereby further purifying Factor H.

14. The method of claim 9, wherein the method further comprises:
   (q) precipitating Factor H from the further enriched Factor H composition.

15. The method of claim 14, wherein the method further comprises the steps of
   (r) binding Factor H to an anion exchange resin; and
   (s) eluting Factor H from the anion exchange resin with an elution buffer,
thereby forming a first eluate containing Factor H.

16. The method of claim 15, further comprising the steps of:
- (t) binding Factor H from the first eluate to a heparin affinity resin; and
- (u) eluting the Factor H from the heparin affinity resin with, an elution buffer, thereby forming a second eluate containing Factor H.

17. The method of claim 9, further comprising the steps of:
- (v) binding impurities to an anion exchange resin under conditions such that Factor H does bind to the resin and is collected in the flow through fraction;
- (w) binding Factor H from the flow through fraction to a heparin affinity resin;
- (x) eluting Factor H from the heparin affinity resin to form an eluate;
- (y) binding Factor H from the eluate to an anion exchange resin; and
- (z) eluting Factor H from the anion exchange resin, thereby further purifying Factor H.

* * * * *

UNITED STATES PATENT AND TRADEMARK OFFICE
CERTIFICATE OF CORRECTION

PATENT NO. : 8,304,524 B2
APPLICATION NO. : 12/842944
DATED : November 6, 2012
INVENTOR(S) : Shawn F. Bairstow et al.

It is certified that error appears in the above-identified patent and that said Letters Patent is hereby corrected as shown below:

In the Claims:

Claim 1, Line 47, Column 61: please insert -- 7.3 -- after about

Claim 1, Line 58, Column 61: please delete "1-1", and insert -- H --

Signed and Sealed this
Second Day of April, 2013

Teresa Stanek Rea
*Acting Director of the United States Patent and Trademark Office*